United States Patent
Van Maris et al.

(10) Patent No.: US 11,198,847 B2
(45) Date of Patent: Dec. 14, 2021

(54) YEAST CELL CAPABLE OF SIMULTANEOUSLY FERMENTING HEXOSE AND PENTOSE SUGARS

(71) Applicant: DSM IP ASSETS B.V., Heerlen (NL)

(72) Inventors: Antonius Jeroen Adriaan Van Maris, Stockholm (SE); Jacobus Thomas Pronk, Delft (NL); Maarten Dirk Verhoeven, Delft (NL); Ioannis Papapetridis, Delft (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/966,741

(22) PCT Filed: Jan. 31, 2019

(86) PCT No.: PCT/EP2019/052307
§ 371 (c)(1),
(2) Date: Jul. 31, 2020

(87) PCT Pub. No.: WO2019/149789
PCT Pub. Date: Aug. 8, 2019

(65) Prior Publication Data
US 2020/0377846 A1    Dec. 3, 2020

(30) Foreign Application Priority Data

Feb. 1, 2018 (EP) .................................. 18154587
Apr. 12, 2018 (EP) .................................. 18166976

(51) Int. Cl.
| | | |
|---|---|---|
| *C12N 15/52* | (2006.01) | |
| *C12N 1/18* | (2006.01) | |
| *C12N 1/22* | (2006.01) | |
| *C12N 9/04* | (2006.01) | |
| *C12N 9/12* | (2006.01) | |
| *C12N 9/90* | (2006.01) | |
| *C12N 9/92* | (2006.01) | |
| *C12P 1/02* | (2006.01) | |

(52) U.S. Cl.
CPC ................. *C12N 1/18* (2013.01); *C12N 1/22* (2013.01); *C12N 9/0006* (2013.01); *C12N 9/1205* (2013.01); *C12N 9/90* (2013.01); *C12N 9/92* (2013.01); *C12N 15/52* (2013.01); *C12P 1/02* (2013.01); *C12Y 101/01* (2013.01); *C12Y 101/01307* (2013.01); *C12Y 207/01016* (2013.01); *C12Y 207/01017* (2013.01); *C12Y 501/03001* (2013.01); *C12Y 501/03004* (2013.01); *C12Y 503/01004* (2013.01); *C12Y 503/01005* (2013.01); *C12Y 503/01009* (2013.01)

(58) Field of Classification Search
CPC ................. C12Y 207/01017; C12N 15/52
See application file for complete search history.

(56) References Cited

U.S. PATENT DOCUMENTS

| | | |
|---|---|---|
| 9,034,608 B2 | 5/2015 | Wisselink et al. |
| 9,353,376 B2 | 5/2016 | Wisselink et al. |
| 2014/0141473 A1 | 5/2014 | Klaassen et al. |
| 2018/0291404 A1 | 10/2018 | Papapetridis et al. |

FOREIGN PATENT DOCUMENTS

| | | |
|---|---|---|
| WO | 2012049170 A2 | 4/2012 |
| WO | 2012138942 A1 | 10/2012 |
| WO | 2017060195 A1 | 4/2017 |

OTHER PUBLICATIONS

PCT International Search Report for PCT/EP2019/052307, dated May 29, 2019.
Soo Rin Kim et al: "Simultaneous Co-Fermentaition of Mixed Sugars: a Promising Strategy for Producing Cellulosic Ethanol" Trends in Biotechnology. vol. 30, No. 5, (May 1, 2012), pp. 274-282.
Boles et al: "The Role of the Nao-Dependent Glutamate Gehydrogenase in Restoring Growth on Glucose of a *Saccharomyces cerevisiae* Phosphoglucose Isomerase Mutant", European Journal of Biochemistry, Wiley-Blackwell Publishing Ltd, GB, vol. 217, No. 1, (Oct. 1, 1993), pp. 469-477.
Milica Momcilovic et al: "Roles of the Glycogen-binding Domain and Snf4 in Glucose Inhibition of SNFI Protein Kinase", Journal of Biological Chemistry, vol. 283, No. 28, (Jul. 11, 2008), pp. 19521-19529.
Omur Kayikci et al: "Glucose repression in *Saccharomyces cerevisiae*", FEMS Yeast Research Jun. 10, vol. 15, No. 6, (Jul. 22, 2015), pp. 1-8.
Wiatrowski et al: "Mutations int he Gal83 Glycogen-Binding Domain Acitivate the Snfl/Gal83 Kinase Pathway by a Glycogen-Independent Mechanism" Molecular and Cellular Biology, vol. 24, No. 1, (Jan. 1, 2004) pp. 352-361.

*Primary Examiner* — Tekchand Saidha
(74) *Attorney, Agent, or Firm* — McBee Moore & Vanik IP, LLC; Susan McBee; Chester Moore

(57) ABSTRACT

The invention relates to a method for preparing a yeast which is capable of simultaneously fermenting a pentose and a hexose sugar, the method comprising providing a yeast which comprises: one or more heterologous genes encoding an enzyme of a pentose metabolic pathway, a disruption of a gene encoding a ribulose-phosphate 3-epimerase and a disruption of a gene encoding a glucose-6-phosphate isomerase, and one or more overexpressed endogenous genes encoding an enzyme of the pentose phosphate pathway; and subjecting the yeast to evolutionary engineering on a medium comprising a hexose sugar and at least one pentose sugar, selecting for a yeast with improved growth rate when grown on a media comprising a hexose and at least one pentose sugar, so as to obtain an evolved yeast.

16 Claims, 15 Drawing Sheets

Figure 1:
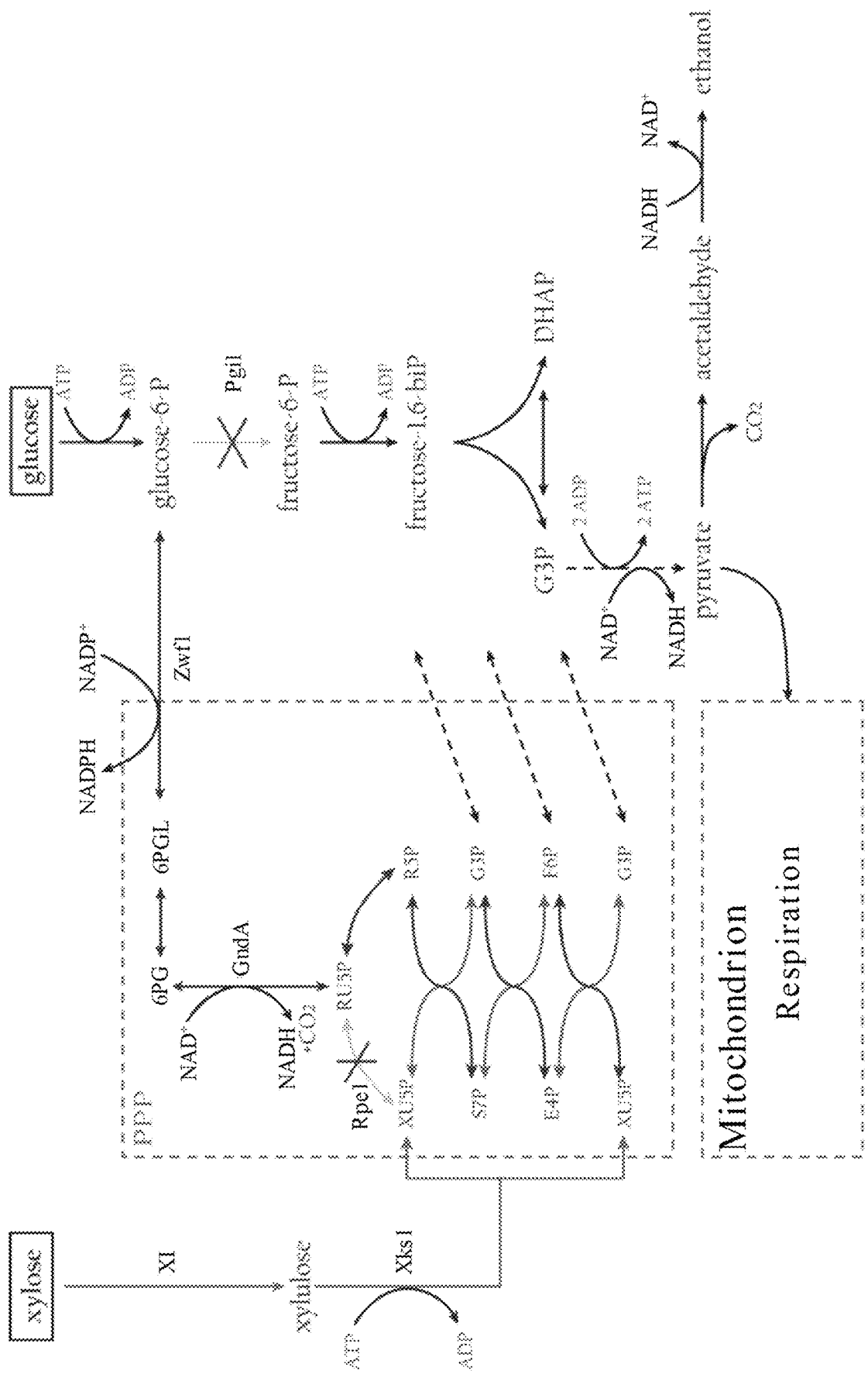

Specification includes a Sequence Listing.

YEAST CELL CAPABLE OF SIMULTANEOUSLY FERMENTING HEXOSE AND PENTOSE SUGARS

CROSS-REFERENCE TO RELATED APPLICATIONS

This application is the National Stage entry of International Application No. PCT/EP2019/052307, filed 31 Jan. 2019, which claims priority to European Patent Application No. EP18154587.2, filed 1 Feb. 2018 and European Patent Application No. EP18166976.3, filed 12 Apr. 2018.

REFERENCE TO SEQUENCE LISTING SUBMITTED AS A COMPLIANT ASCII TEXT FILE (.txt)

Pursuant to the EFS-Web legal framework and 37 C.F.R. § 1.821-825 (see M.P.E.P. § 2442.03(a)), a Sequence Listing in the form of an ASCII-compliant text file (entitled "Sequence_Listing_2919208-534000_ST25.txt" created on 28 Jul. 2020, and 79,113 bytes in size) is submitted concurrently with the instant application, and the entire contents of the Sequence Listing are incorporated herein by reference.

FIELD

The invention relates to a yeast which is capable of simultaneously fermenting a pentose and a hexose sugar, to a method for preparing said yeast, and to a process for the production of an organic compound using said yeast.

DESCRIPTION OF RELATED ART

Most of the ethanol produced as alternative for fossil fuels is currently from fermentation of corn starch and sugar cane based sucrose. In order to reach the ambitious goals for producing renewable fuels, new technologies are being developed for converting non-food biomass into fermentation products such as ethanol. *Saccharomyces cerevisiae* is the organism of choice in the ethanol industry, but it cannot utilize five-carbon sugars contained in the hemicellulose component of biomass feedstocks. Hemicellulose can make up to 20-30% of biomass, with xylose and arabinose being the most abundant C5 sugars. Heterologous expression of a xylose isomerase (XI) is an option for enabling yeast cells to metabolize and ferment xylose. Likewise, expression of bacterial genes araA, araB, and araD in *S. cerevisiae* strains results in utilization and efficient alcoholic fermentation of arabinose. Fermentation of pentose to ethanol by natural pentose-fermenting yeast species known in the art occurs slowly and results in low yields relative to fermentation rates and ethanol yields that are obtained with conventional yeasts in glucose fermentations. In order to improve the cost effectiveness of the pentose fermentation, it is necessary to increase the rate of fermentation and the ethanol yields obtained. *S. cerevisiae* has an inherent preference for glucose. As a consequence, all current pentose fermenting strains demonstrate sequential utilisation of mixtures of glucose and pentoses or at best the pentose fermentation starts at low glucose concentrations.

It would be desirable to provide a yeast strain that can anaerobically ferment pentose either simultaneous with glucose (co-fermentation of pentose and glucose) and/or faster than is is known in the art.

SUMMARY

In connection with the present invention there is provided a method for preparing a yeast which is capable of simultaneously fermenting a pentose and a hexose sugar, said method comprising:
(a) providing a yeast which comprises:
  one or more heterologous genes encoding an enzyme of a pentose metabolic pathway;
  a disruption of a gene encoding a ribulose-phosphate 3-epimerase and a disruption of a gene encoding a glucose-6-phosphate isomerase; and
  one or more overexpressed endogenous genes encoding an enzyme of the pentose phosphate pathway; and optionally:
  a heterologous gene encoding an NADH-dependent 6-phosphogluconate dehydrogenase; and
  a disruption of one or more genes encoding an NADPH dependent 6-phosphogluconate dehydrogenase,
(b) subjecting said yeast to evolutionary engineering on a medium comprising a hexose sugar and at least one pentose sugar, selecting for a yeast with improved growth rate when grown on a media comprising a hexose and at least one pentose sugar, so as to obtain an evolved yeast; and optionally
(c) isolating a single cell isolate from said evolved yeast; which method subsequently comprises either:
(d) restoring, in the (optionally isolated) evolved yeast, one or more of the disrupted genes, or:
(d') identifying genetic permutations in at least part of the genome of the optionally isolated evolved yeast by genome sequencing; and
(e) constructing an improved pentose and hexose-fermenting yeast comprising one or more of said genetic permutations.

FIG. 1: Schematic representation of central carbon metabolism in yeast strain engineered for forced co-consumption of glucose and xylose. In a pgi1Δ rpe1Δ *Saccharomyces cerevisiae* strain expressing a heterologous xylose isomerase (XylA, Kuyper et al. 2003), the native 6-phosphogluconate dehydrogenases (Gnd1 and Gnd2) were replaced by a bacterial NAD+-dependent enzyme (GndA, Papapetridis et al. 2016). Additionally, xylulokinase (Xks1) and enzymes of the pentose phosphate pathway (PPP) were overexpressed. F6P fructose-6-phosphate; G3P glyceraldehyde-3-phosphate; DHAP dihydroxyacetone phosphate; 6PGL 6-phosphogluconolactone; 6PG 6-phosphogluconate; RU5P ribulose-5-phosphate; XU5P xylulose-5-phosphate; R5P ribose-5-phosphate; S7P sedoheptulose-7-phosphate; E4P erythrose-4-phosphate.

Figure 2:
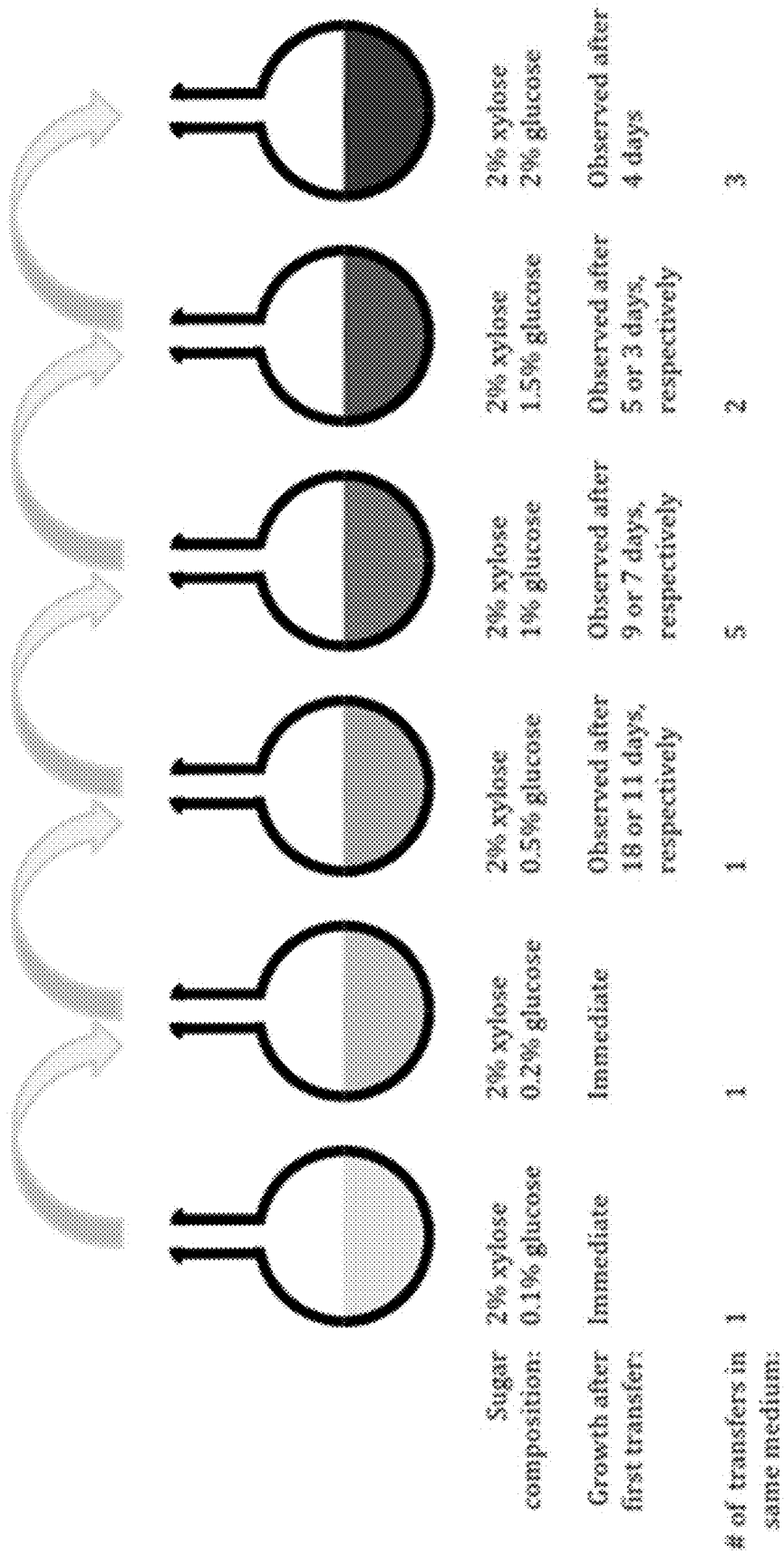

FIG. 2: Laboratory evolution of *S. cerevisiae* IMX1046 (pgi1Δ rpe1Δ gnd1Δ gnd2Δ gndΔ XylA XKS1↑ PPP↑) for improved co-consumption of xylose at high glucose concentrations. Cultures were grown in shake flasks containing 100 mL SM (pH 6) supplemented with 20 g L−1 xylose and progressively increasing glucose concentrations. In every transfer, 0.05 mL of an exponentially growing culture was used to inoculate the next shake flask.

Figure 3:
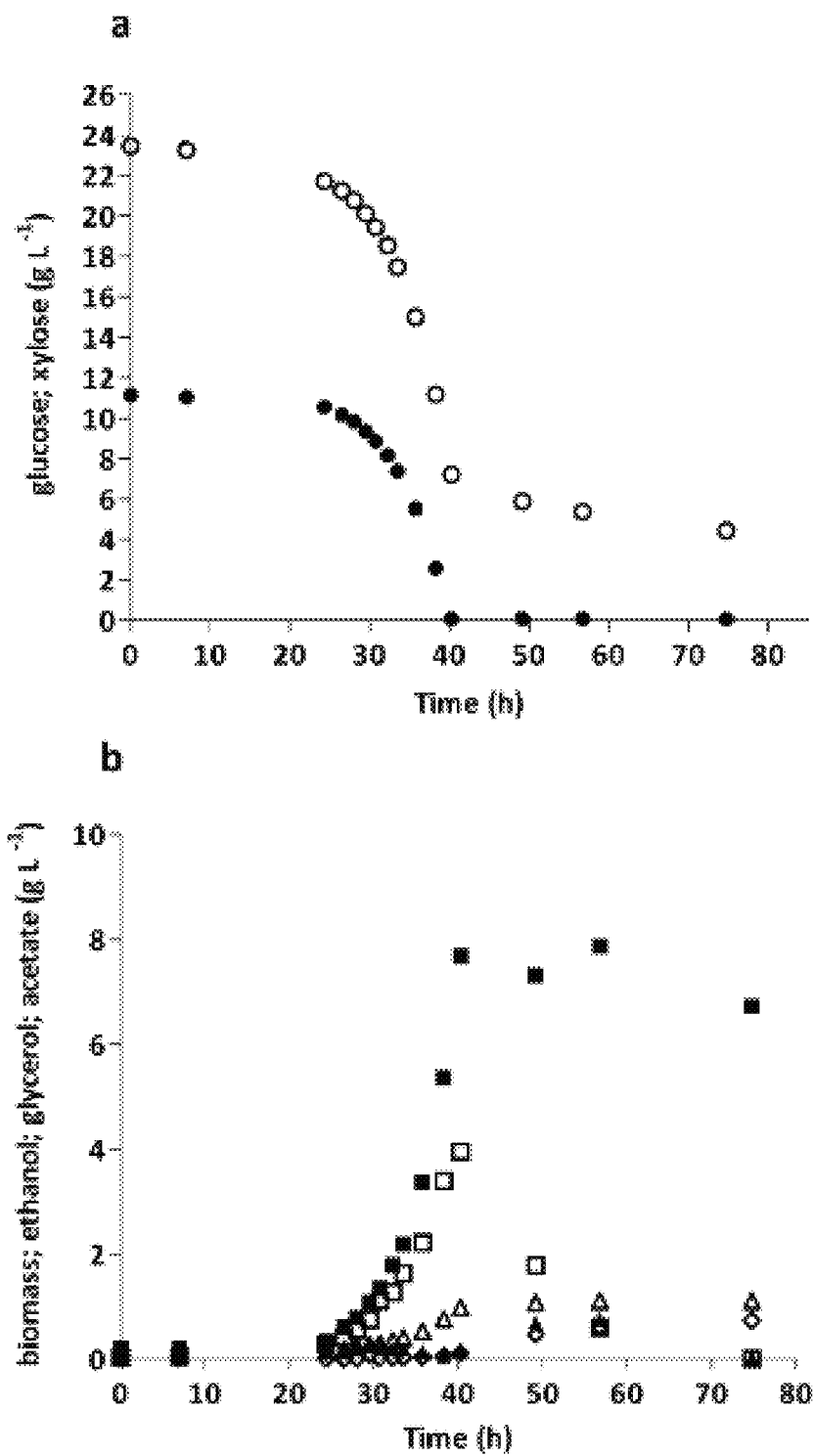
Figure 3:
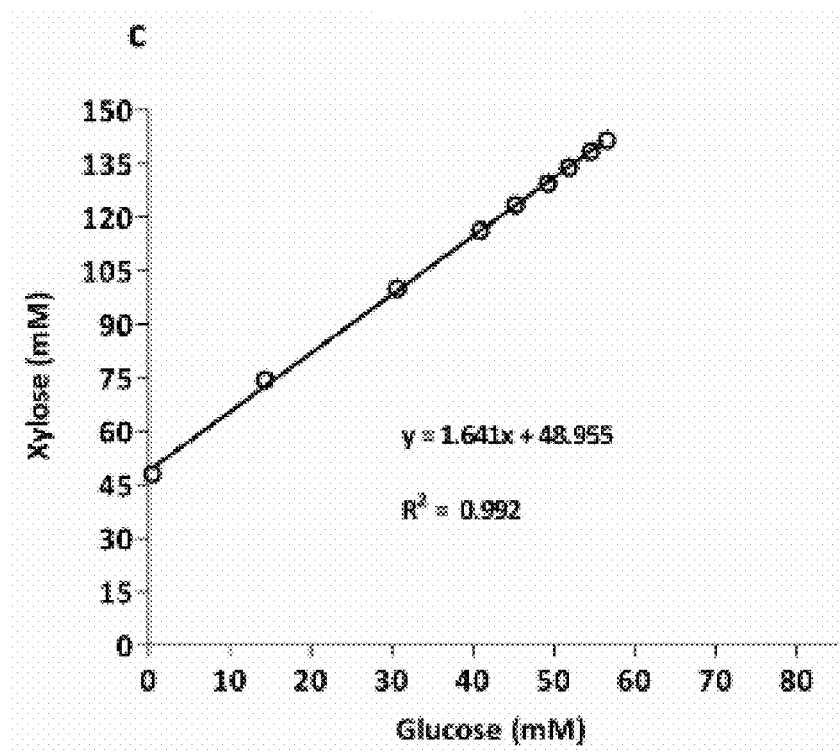

FIG. 3. Sugar consumption, biomass and metabolite production profiles of the evolved *S. cerevisiae* strain IMS0629 (pgi1Δ rpe1Δ gnd1Δ gnd2Δ gndΔ XylA XKS1↑ PPP↑), grown on SM with 10 g L$^{-1}$ glucose and 20 g L$^{-1}$ xylose in aerobic bioreactor batch cultures (pH 5, 30° C.). Cultures were grown in duplicate, the data shown are from a single representative culture. a: ● glucose, ○ xylose; b: ■ biomass □ ethanol ▲ acetate △ glycerol ◇ xylitol; c: ratio of xylose and glucose consumption during exponential growth phase.

Figure 4:
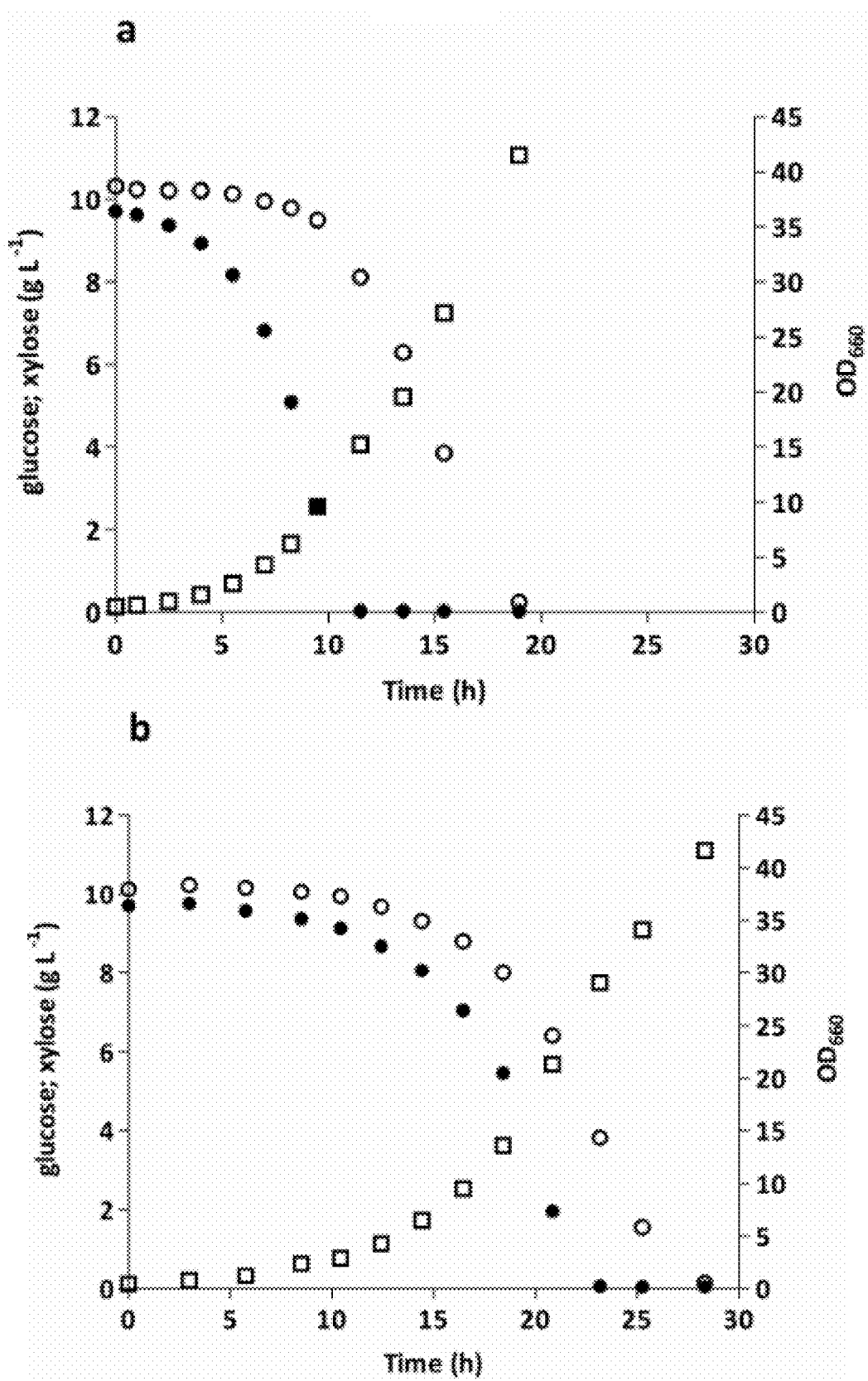
Figure 4:
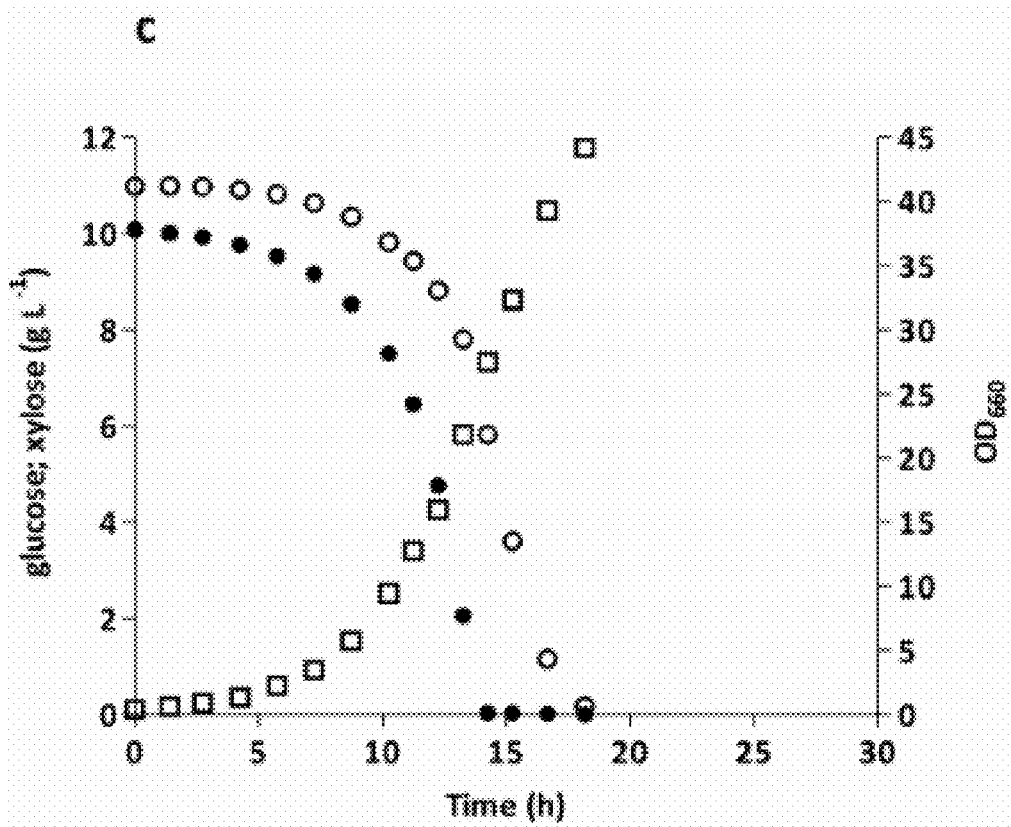
Figure 4:
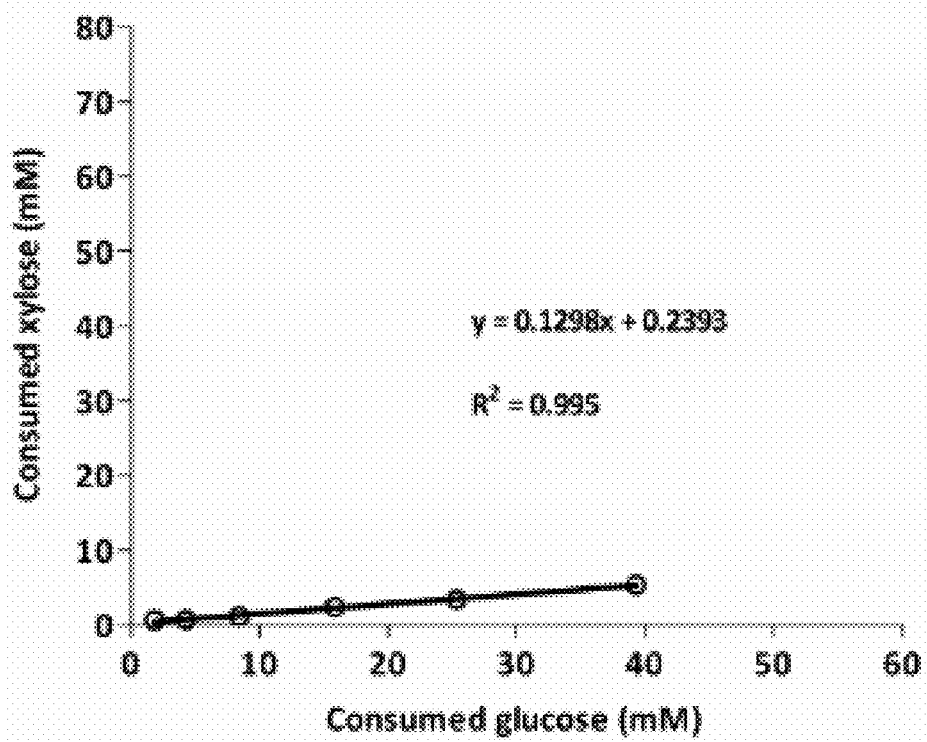
Figure 4:
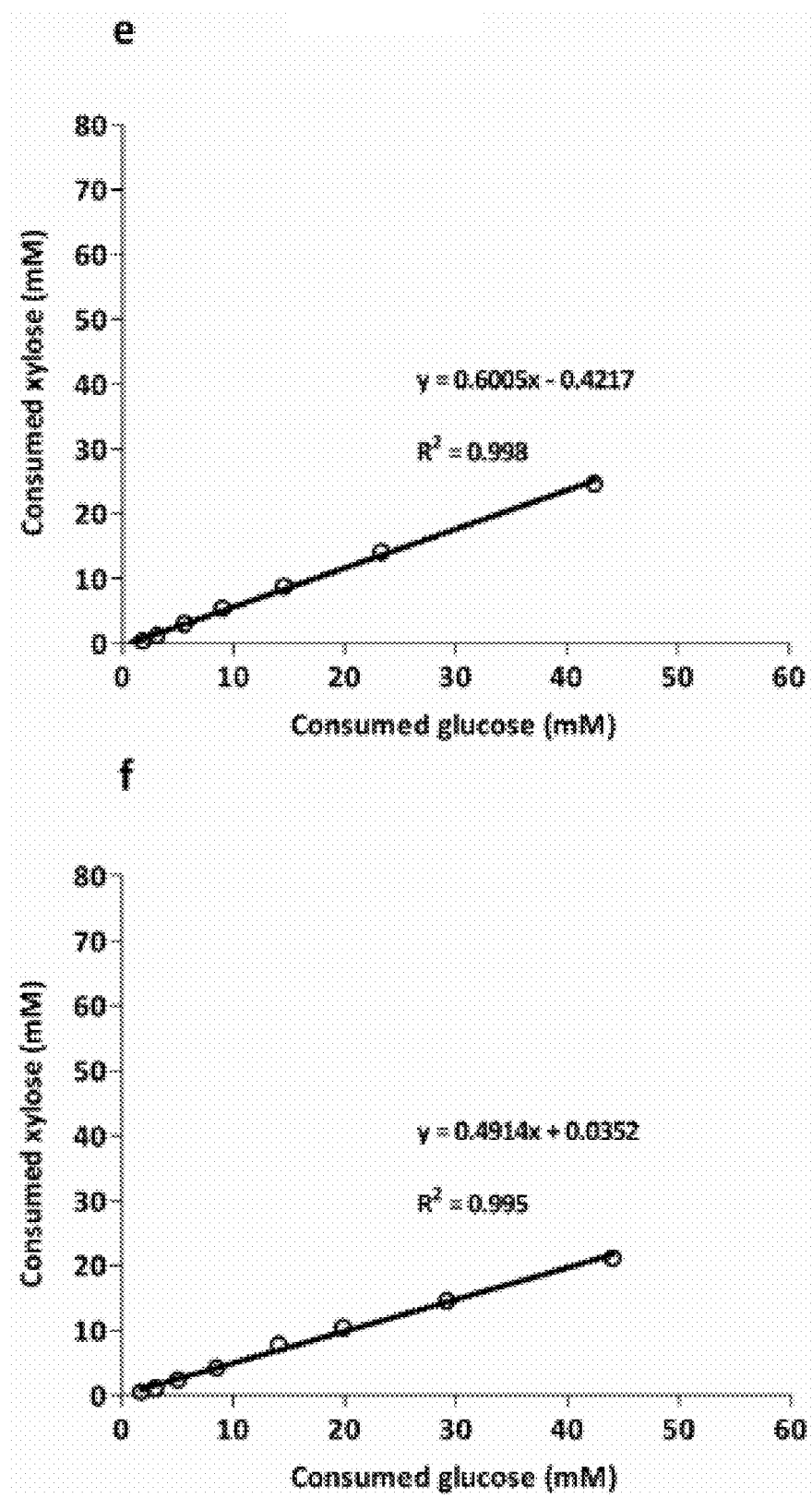

FIG. 4. Consumption of glucose and xylose and growth of strains IMU079 (XKS1↑ PPP↑ pAKX002; a, d), IMX1515 (hxk2Δ rsp5Δ XKS1↑ PPP↑ pAKX002; b, e) and IMX1583 (hxk2Δ gal83::GAL83G$^{673T}$ XKS1↑ PPP↑ pAKX002; c, f) in batch cultures. The three strains were grown on SM (urea as nitrogen source) with 10 g L$^{-1}$ glucose and 10 g L$^{-1}$ xylose in aerobic shake-flask cultures (pH 6, 30° C.). a, b, c: glucose, ○ xylose, □ OD$_{660}$; d, e, f: ratio of xylose and glucose consumption during exponential growth phase.

Figure 5:
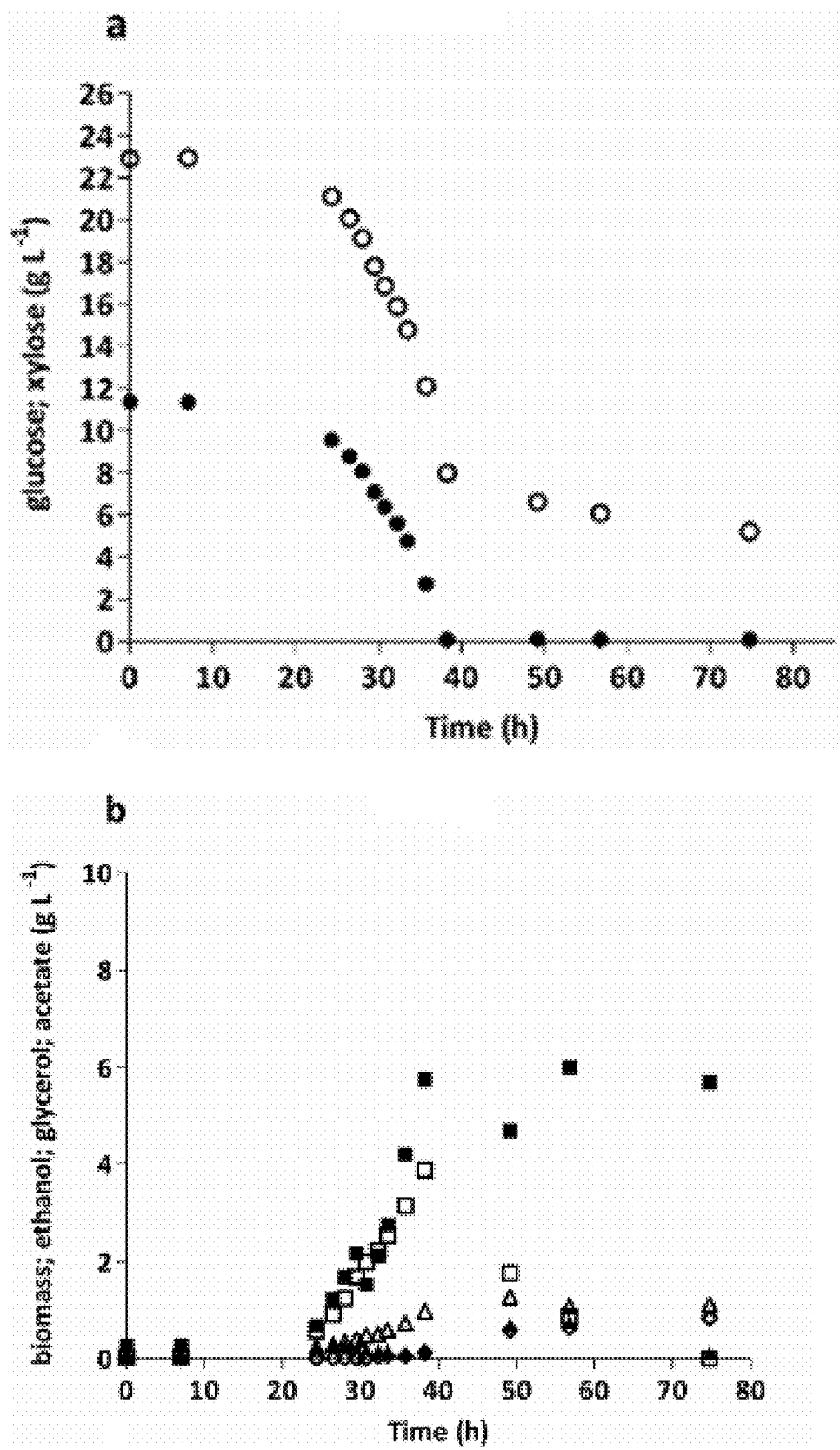
Figure 5:
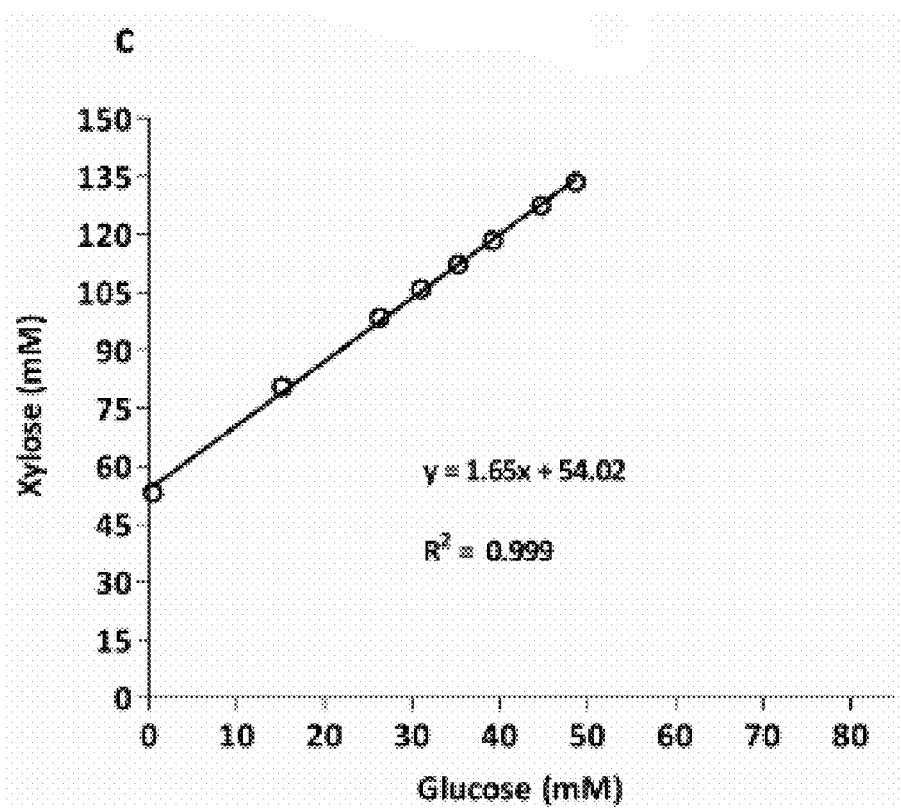

FIG. 5. Sugar consumption, biomass and metabolite production profiles of the evolved S. cerevisiae strain IMS0629 (pgi1Δ rpe1Δ gnd1Δ gnd2Δ gndA XylA XKS1↑ PPP↑), grown on SM with 10 g L-1 glucose and 20 g L-1 xylose in aerobic bioreactor batch cultures (pH 5, 30° C.). Cultures were grown in duplicate, the data shown are from a single representative culture. a: ● glucose, ○ xylose; b: ■ biomass □ ethanol ▲ acetate Δ glycerol ◇ xylitol; c: ratio of xylose and glucose consumption during exponential growth phase. This is a replicate of the experiment of FIG. 3.

Figure 6:
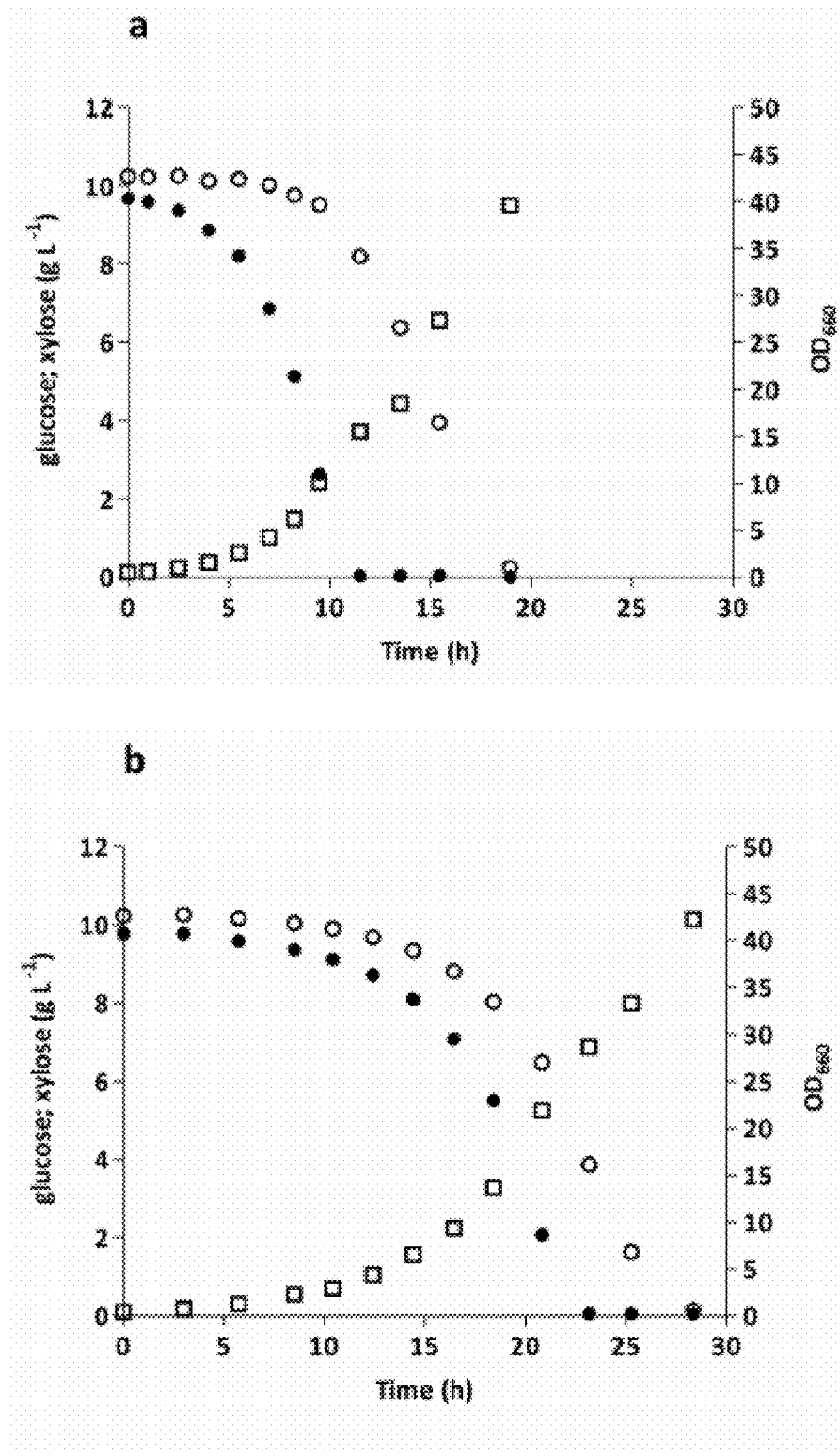
Figure 6:
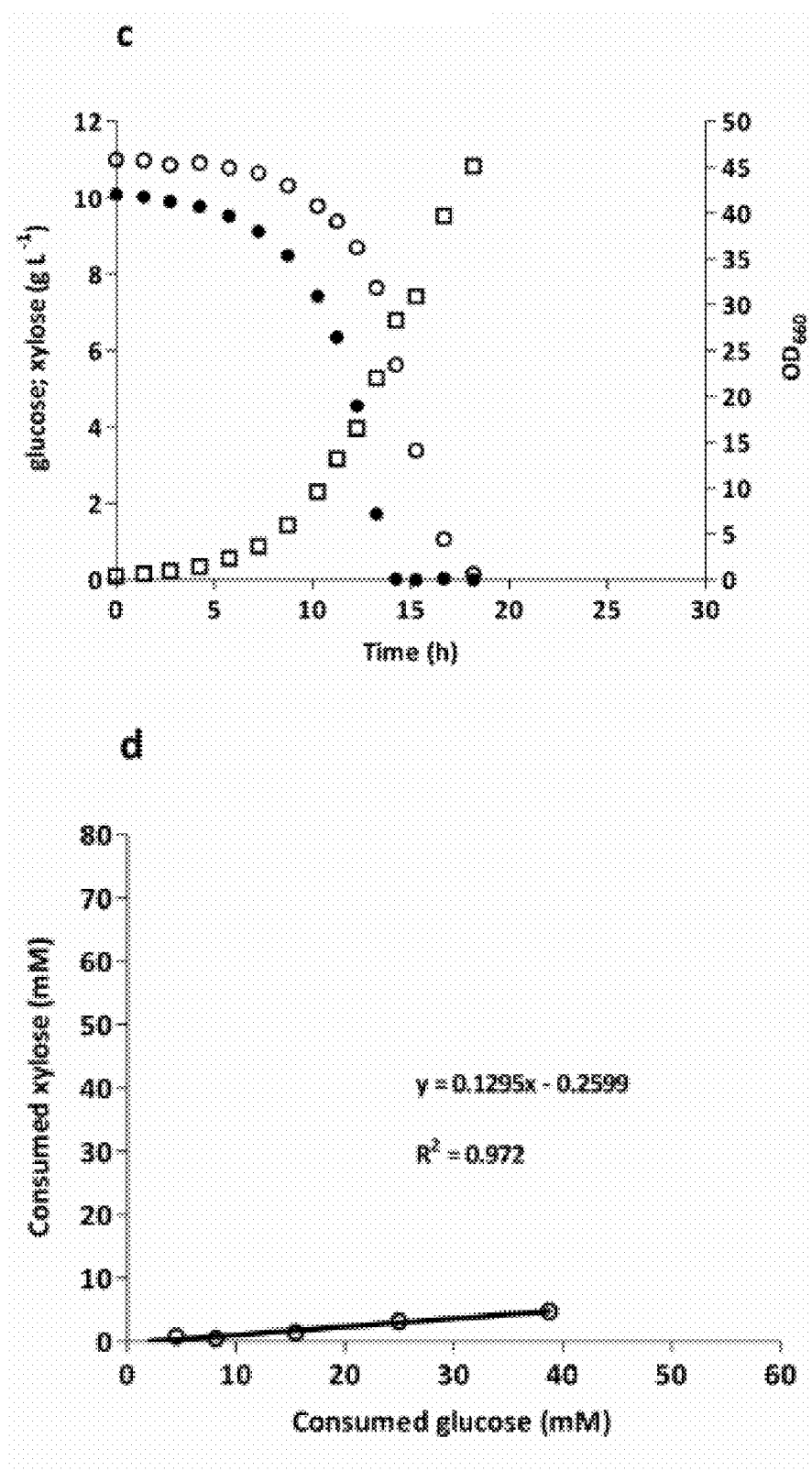
Figure 6:
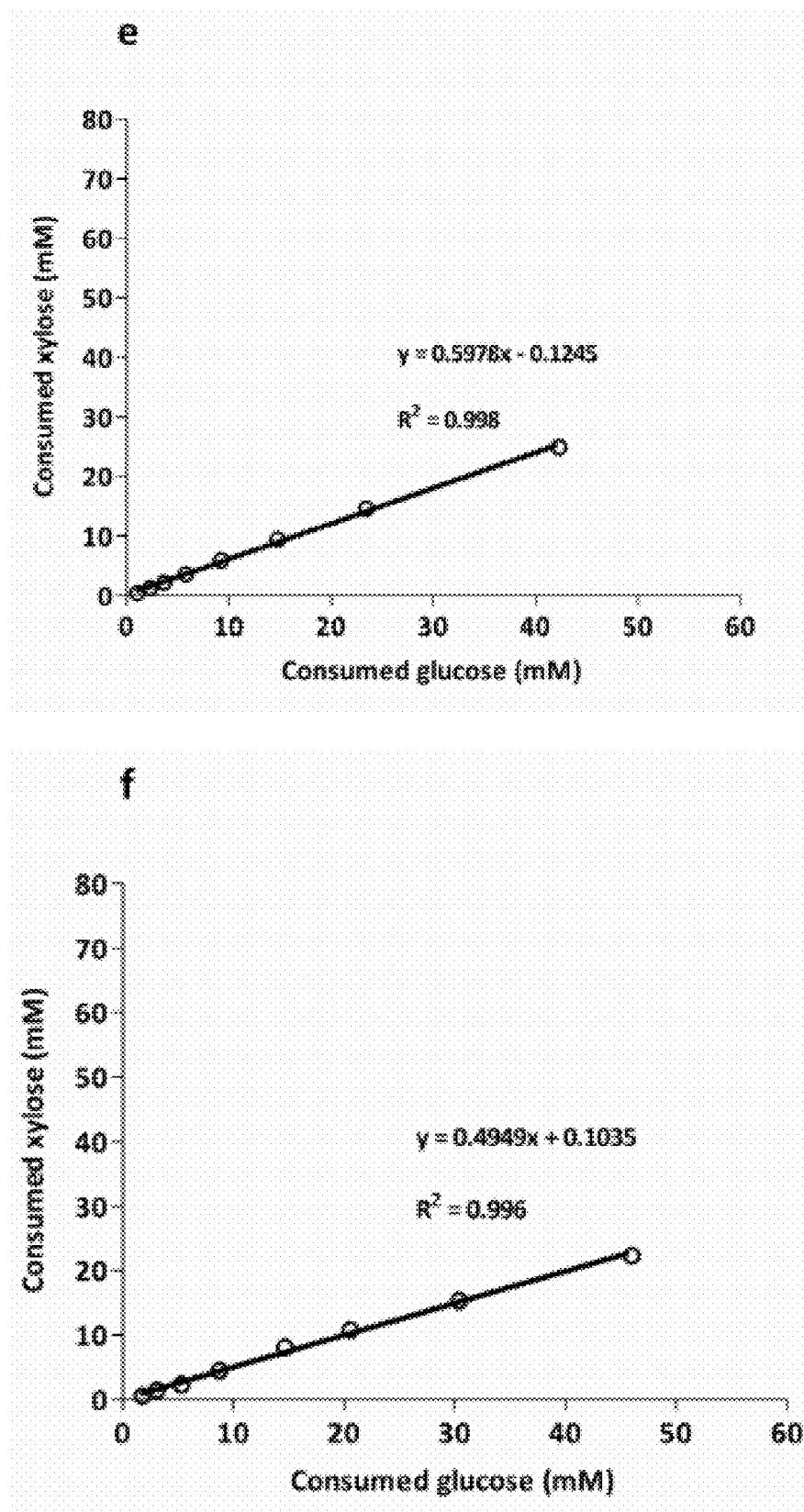

FIG. 6. Consumption of glucose and xylose and growth of strains IMU079 (XKS1↑ PPP↑ pAKX002; a, d), IMX1515 (hxk2Δ rsp5Δ XKS1↑ PPP↑ pAKX002; b, e) and IMX1583 (hxk2Δ gal83::GAL83G673T XKS1β PPP↑ pAKX002; c, f) in batch cultures. The three strains were grown on SM (urea as nitrogen source) with 10 g L-1 glucose and 10 g L-1 xylose in aerobic shake-flask cultures (pH 6, 30° C.). a, b, c: ● glucose, ○ xylose, □ OD660; d, e, f: ratio of xylose and glucose consumption during exponential growth phase. This is a replicate of the experiment of FIG. 4.

Figure 7:
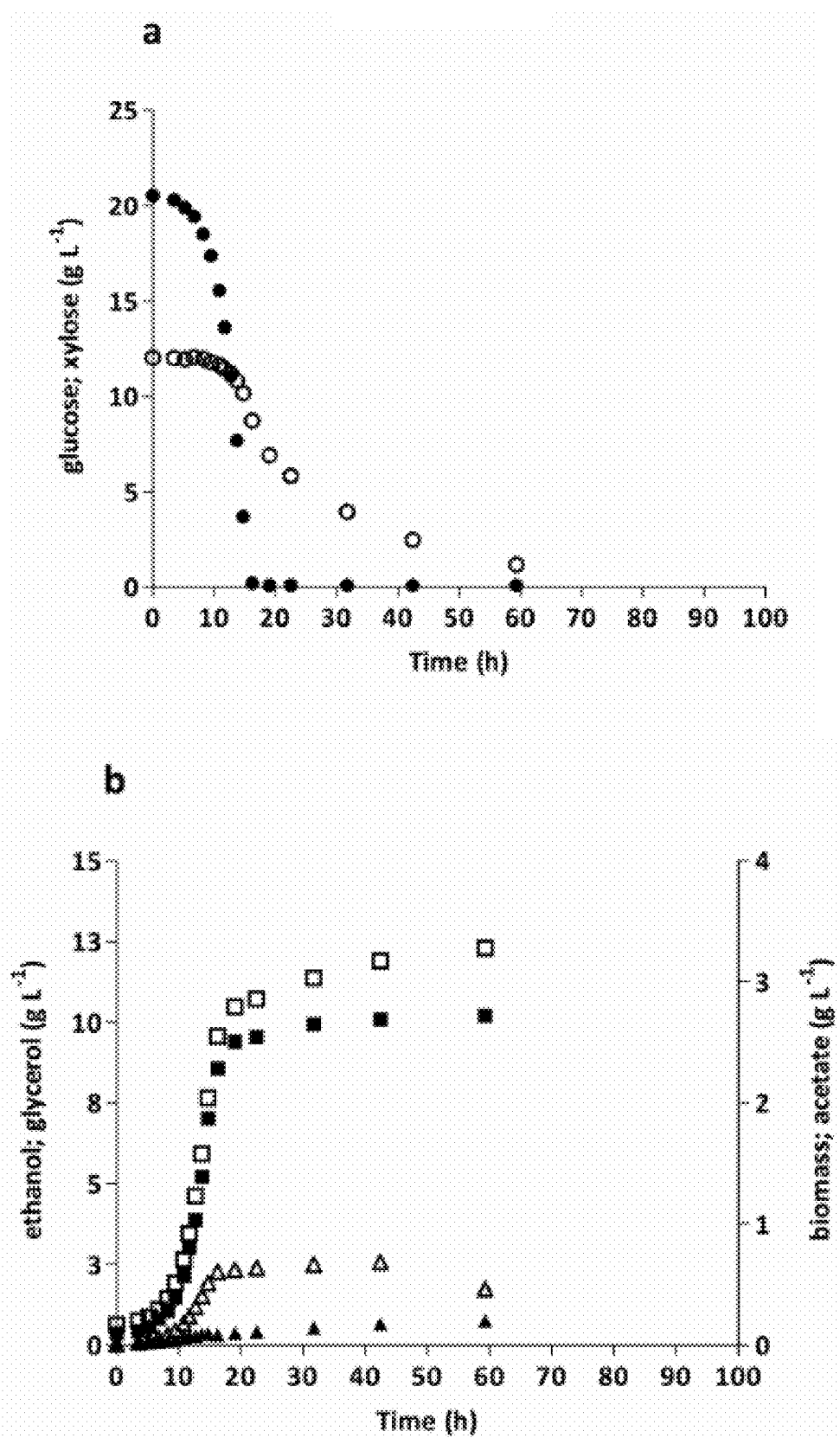
Figure 7:
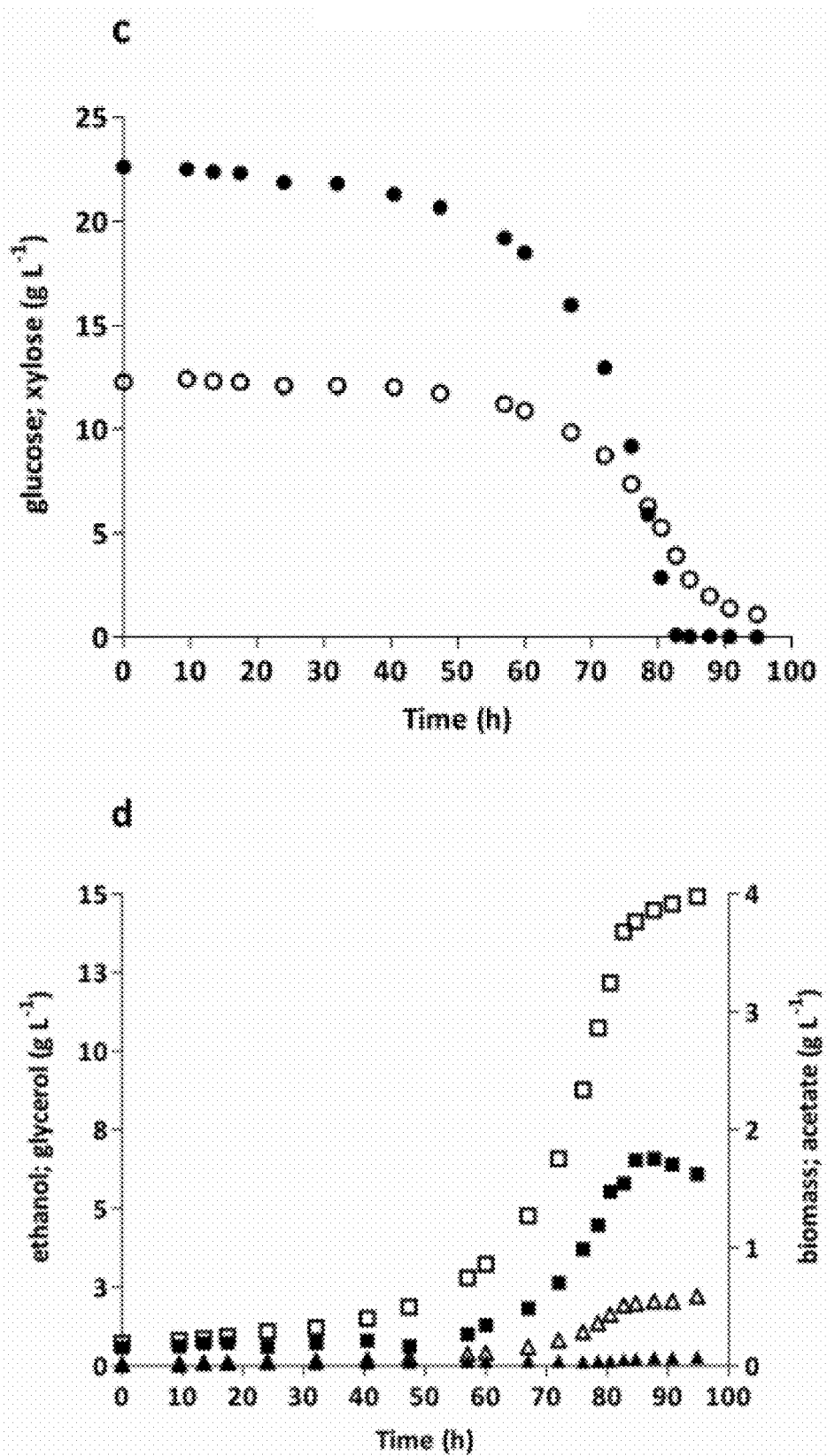
Figure 7:
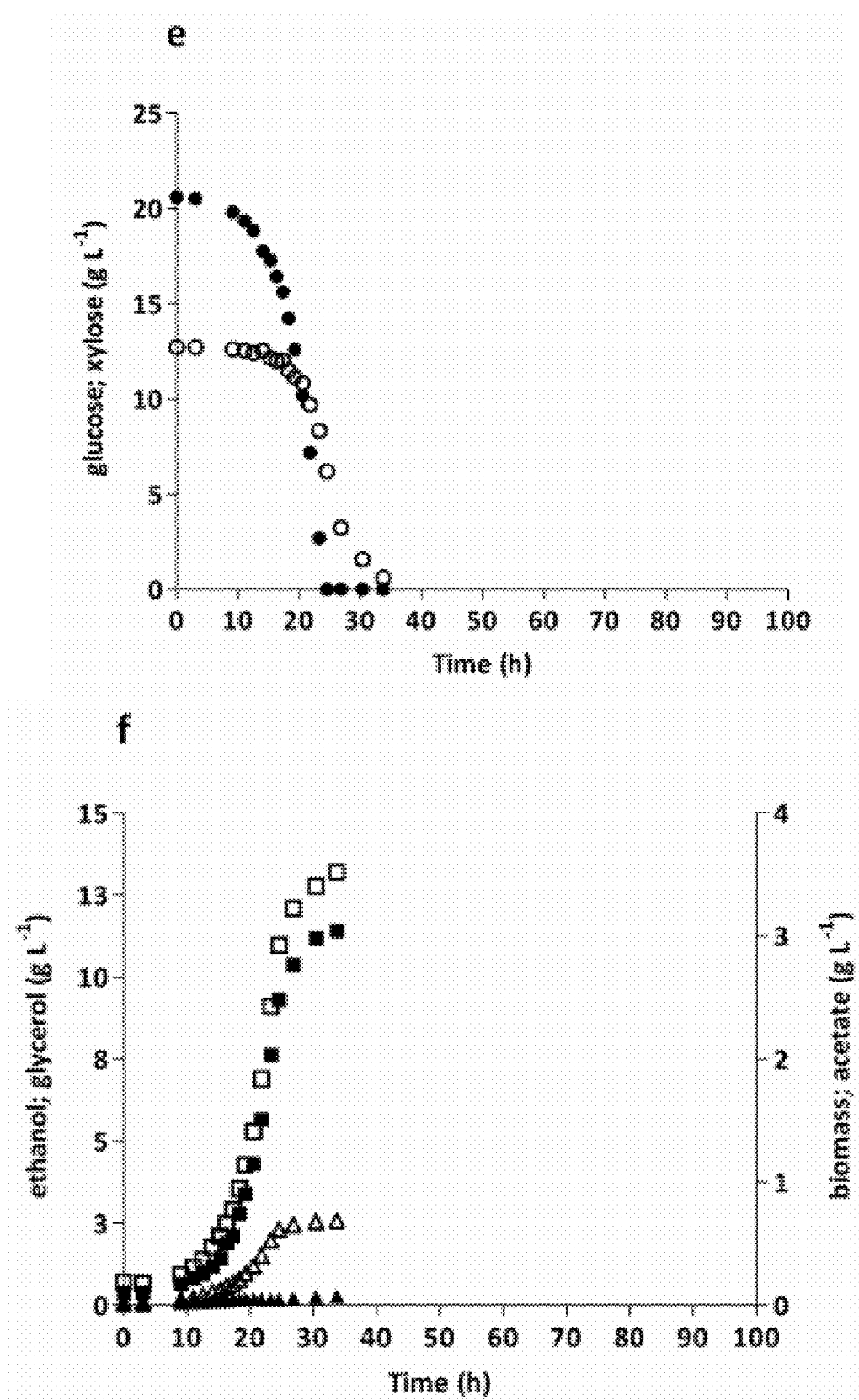

FIG. 7. Sugar consumption, biomass and metabolite production profiles of S. cerevisiae strains IMU079 (XKS1↑ PPP↑ pAKX002; a, b), IMX1515 (hxk2Δ rsp5Δ XKS1↑ PPP↑ pAKX002; c, d) and IMX1583 (hxk2Δ gal83:: GAL83G673T XKS1↑ PPP↑ pAKX002; e, f), grown on SM with 20 g L-1 glucose and 10 g L-1 xylose in anaerobic bioreactor batch cultures (pH 5, 30° C.). Cultures were grown in duplicate, the data shown are from a single representative culture. a: ● glucose, ○ xylose; b: ■ biomass □ ethanol ▲ acetate Δ glycerol. Data on ethanol corrected for evaporation.

DETAILED DESCRIPTION OF A PREFERRED EMBODIMENT

TABLE 1

Brief description of the sequence listing

| SEQ ID NO | Description |
|---|---|
| 1 | Amino acid sequence of S cerevisiae ribulose-phosphate 3-epimerase Rpe1 |
| 2 | Amino acid sequence of S cerevisiae glucose-6-phosphate isomerase Pgi1 |
| 3 | Amino acid sequence of S cerevisiae NADPH dependent 6-phosphogluconate dehydrogenase (Gnd1) |
| 4 | Amino acid sequence of S cerevisiae NADPH dependent 6-phosphogluconate dehydrogenase (Gnd2) |
| 5 | Amino acid sequence of NADH-dependent 6-phosphogluconate dehydrogenase (gndA) |
| 6 | Amino acid sequence of S cerevisiae Gal83 |
| 7 | Amino acid sequence of S cerevisiae 6-phosphogluconolactonase (Sol3) |
| 8 | Amino acid sequence of S cerevisiae Glucose-6-phosphate 1-dehydrogenase (Zwf1) |
| 9 | Amino acid sequence of Piromyces xylose isomerase (xyIA) |
| 10 | Amino acid sequence of Xks |
| 11 | Amino acid sequence of XR |
| 12 | Amino acid sequence of XDH |
| 13 | Amino acid sequence of Lactobacillus plantarum L-arabinose isomerase (araA) |
| 14 | Amino acid sequence of Lactobacillus plantarum L-ribulokinase (araB) |
| 15 | Amino acid sequence of Lactobacillus plantarum L-ribulose-5P-4-epimerase (araD) |
| | Primers |
| 16 | 5980 |
| 17 | 5792 |
| 18 | 5979 |
| 19 | 5978 |
| 20 | 5941 |
| 21 | 6005 |
| 22 | 9269 |
| 23 | 9401 |
| 24 | 11270 |
| 25 | 11373 |
| 26 | 8956 |
| 27 | 8960 |
| 28 | 8958 |
| 29 | 8961 |
| 30 | 8953 |
| 31 | 8964 |
| 32 | 8984 |
| 33 | 8986 |
| 34 | 4870 |
| 35 | 7369 |
| 36 | 3290 |
| 37 | 3291 |
| 38 | 4068 |
| 39 | 3274 |
| 40 | 3275 |
| 41 | 3847 |
| 42 | 3276 |

TABLE 1-continued

Brief description of the sequence listing

| SEQ ID NO | Description |
|---|---|
| 43 | 4691 |
| 44 | 3277 |
| 45 | 3283 |
| 46 | 3288 |
| 47 | 7133 |
| 48 | 10460 |
| 49 | 10461 |
| 50 | 6285 |
| 51 | 7548 |
| 52 | 6280 |
| 53 | 6273 |
| 54 | 6281 |
| 55 | 6270 |
| 56 | 6282 |
| 57 | 6271 |
| 58 | 6284 |
| 59 | 6272 |
| 60 | 6283 |
| 61 | 6275 |
| 62 | 6287 |
| 63 | 6276 |
| 64 | 6288 |
| 65 | 6277 |
| 66 | 6289 |
| 67 | 6274 |
| 68 | 5920 |
| 69 | 9029 |
| 70 | 7135 |
| 71 | 7222 |
| 72 | 11273 |
| 73 | 11274 |
| 74 | 3275 |
| 75 | 3276 |
| 76 | 5971 |
| 77 | 6637 |
| 78 | 6640 |
| 79 | 7869 |
| 80 | 7870 |
| 81 | 7871 |
| 82 | 7872 |
| 83 | 7873 |
| 84 | 7874 |
| 85 | 7875 |
| 86 | 7877 |
| 87 | 7923 |
| 88 | 8969 |
| 89 | 8987 |
| 90 | 8988 |
| 91 | 533 |
| 92 | 3354 |
| 93 | 3837 |
| 94 | 3843 |
| 95 | 4173 |
| 96 | 4184 |
| 97 | 4692 |
| 98 | 5231 |
| 99 | 6632 |
| 100 | 6633 |
| 101 | 7056 |
| 102 | 7298 |
| 103 | 7479 |
| 104 | 9010 |
| 105 | 1814 |
| 106 | 1815 |
| 107 | 5004 |
| 108 | 5007 |
| 109 | 7868 |
| 110 | 7922 |
| 111 | 9271 |
| 112 | 9272 |
| 113 | 9275 |
| 114 | 9276 |
| 115 | 4930 |
| 116 | 4931 |
| 117 | 11273 |
| 118 | 11274 |

TABLE 1-continued

Brief description of the sequence listing

| SEQ ID NO | Description |
|---|---|
| 119 | 11376 |
| 120 | 11377 |
| 121 | 9279 |
| 122 | 9280 |
| 123 | 9281 |
| 124 | 9282 |
| 125 | 5888 |
| 126 | 5889 |
| 127 | 11271 |
| 128 | 11272 |
| 129 | 11374 |
| 130 | 11375 |

The invention provides a method for preparing a yeast which is capable of simultaneously fermenting a pentose and a hexose sugar. A yeast which is dependent on the simultaneous consumption of both a hexose and pentose sugar for its cell growth and which is not able to grow on only one of hexose or pentose sugar is subjected to evolutionary engineering on a medium comprising a hexose sugar and at least one pentose sugar, selecting for a yeast with improved growth rate when grown on a media comprising a hexose and at least one pentose sugar. The yeast at the start of the evolutionary engineering comprises one or more pentose sugar metabolic pathways, such as an arabinose metabolic pathway or a xylose metabolic pathway. Moreover, one or more endogenous genes of said yeast are disrupted, namely a gene encoding a ribulose-phosphate 3-epimerase and a gene encoding a glucose-6-phosphate isomerase. Optionally, one or more genes encoding an NADPH dependent 6-phosphogluconate dehydrogenase are also disrupted. In the latter case, that is, if one or more genes encoding an NADPH dependent 6-phosphogluconate dehydrogenase are disrupted, one or more copies of a heterologous gene encoding an NADH-dependent 6-phosphogluconate dehydrogenase (gndA) are introduced into the yeast. One or more endogenous genes of the pentose phosphate pathway are overexpressed. These modifications make the yeast dependent on the simultaneous consumption of both a hexose and pentose sugar for its cell growth, and the yeast is not able to grow on only one of hexose or pentose sugar. This property makes it suitable to undergo evolutionary engineering in order to prepare a yeast which is able to simultaneously consume pentose and hexose sugars. The yeast is then subjected to evolutionary engineering, selecting for a yeast with improved growth rate when grown on media comprising a hexose and at least one pentose sugar, so as to obtain an evolved yeast. The evolved yeast is optionally isolated. The method can proceed in at least two ways. Firstly, one or more of the disrupted genes can be restored, so as to restore its ability to ferment hexose or pentose sugar as sole carbon source. Alternatively, the genomic DNA of the evolved yeast can be isolated, sequenced and mutations therein are identified. This information can then be used to construct a yeast which is able to ferment (consume) pentoses and hexoses simultaneously and which is useful in the production of e.g. ethanol from lignocellulosic biomass hydrolysates, allowing for shorter fermentation time. The invention also provides a recombinant yeast comprising one or more heterologous genes of a pentose metabolic pathway, which yeast further comprises a gene encoding a variant of a parent (endogenous) polypeptide, wherein the variant comprises an amino acid sequence which, when aligned with the amino acid sequence set out in SEQ ID NO: 6, comprises at least one mutation, and a process for the production of an organic compound comprising using said yeast.

With regard to the present invention, it is understood that organisms also include synonyms or basonyms of such species having the same physiological properties, as defined by the International Code of Nomenclature of Prokaryotes or the International Code of Nomenclature for algae, fungi, and plants (Melbourne Code). A cell may be a cell found in nature or a cell derived from a parent cell after genetic manipulation or classical mutagenesis.

The term "expression" includes any step involved in the production of (a) polypeptide(s) including, but not limited to, transcription, post transcriptional modification, translation, post-translational modification, and secretion. A reduction or abolishment of production of B means a limitation to x % or less B produced via enzymatic conversion of A. This can be achieved with an enzyme/protein/cell/gene as described herein. An increase in production of B means an increase of at least x % B produced via enzymatic conversion of A compared to the amount B obtained in a process using a non-modified cell/wild type protein/enzyme/gene. Reduction or increase of gene expression can be measured by various methods, such as e.g. Northern, Southern or Western blot technology, and transcriptomics as known in the art. The terms "increase of activity" or "overexpression" are used interchangeably herein.

The term "gene" as used herein refers to a segment of a nucleic acid molecule coding for a polypeptide and including gene regulatory sequences preceding and following the coding sequence, as well as intervening sequences (introns) between individual coding segments (exons). It will further be appreciated that the definition of gene can include nucleic acids that do not encode a polypeptide, but instead provide templates for transcription of functional RNA molecules.

The term "recombinant" when used in reference to a nucleic acid, or protein indicates that the nucleic acid, or protein has been modified in its sequence if compared to its native form by human intervention. The term "recombinant" when referring to a cell indicates that the genome of the cell has been modified in its sequence if compared to its native form by human intervention. The term "recombinant" is synonymous with "genetically modified".

The term "overexpression" refers to a strain which is genetically identical except for the genetic modification causing the overexpression. Thus, by way of example: "a yeast comprising one or more overexpressed endogenous genes encoding an enzyme of the pentose phosphate pathway" means "a yeast comprising one or more overexpressed endogenous genes encoding an enzyme of the pentose phosphate pathway as compared to a yeast which is genetically identical except for the genetic modification causing the overexpression".

For the purpose of this disclosure, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this disclosure the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, emboss.bioinformatics.nl). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the disclosure is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labeled in the output of the program as "longest-identity".

The nucleic acid and protein sequences as disclosed herein can further be used as a "query sequence" to perform a search against public databases to, for example, identify other family members or related sequences. Such searches can be performed using the BLASTN and BLASTX programs (version 2.0) of Altschul, et al. (1990) J. Mol. Biol. 215:403-10. BLAST nucleotide searches can be performed with the BLASTN program, score=100, wordlength=12 to obtain nucleotide sequences homologous to nucleic acid molecules of the disclosure. BLAST protein searches can be performed with the BLASTX program, score=50, wordlength=3 to obtain amino acid sequences homologous to protein molecules of the disclosure. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTX and BLASTN) can be used. See the homepage of the National Center for Biotechnology Information at ncbi.nlm.nih.gov. The terms "yeast" and "yeast cell" have the same meaning and may be used intermittently.

DETAILED DESCRIPTION

In one aspect the invention provides a method for preparing a yeast which is capable of simultaneously fermenting a pentose and a hexose sugar, said method comprising:
(a) providing a yeast which comprises:
one or more heterologous genes encoding an enzyme of a pentose metabolic pathway;
a disruption of a gene encoding a ribulose-phosphate 3-epimerase (EC 5.1.3.1) and a disruption of a gene encoding a glucose-6-phosphate isomerase (E.C. 5.3.1.9); and
one or more overexpressed endogenous genes encoding an enzyme of the pentose phosphate pathway; and optionally:
a heterologous gene encoding an NADH-dependent 6-phosphogluconate dehydrogenase and
a disruption of one or more genes encoding an NADPH-dependent 6-phosphogluconate dehydrogenase, which yeast is dependent on the simultaneous consumption of both a hexose and pentose sugar for its cell growth and which is not able to grow on only one of hexose or pentose sugar; which method subsequently comprises:
(b) subjecting said yeast to evolutionary engineering on media comprising a hexose sugar and at least one pentose sugar, selecting for a yeast with improved growth rate when grown on media comprising a hexose and at least one pentose sugar, so as to obtain an evolved yeast; and optionally
(c) isolating a single cell isolate from said evolved yeast;
and which method subsequently comprises either:
(d) restoring, in the (optionally isolated) evolved yeast, one or more of the disrupted genes, so as to restore its ability to ferment hexose or pentose sugar as sole carbon source,
or:
(d') identifying genetic permutations in at least part of the genome of the optionally isolated evolved yeast by genome sequencing; and
(e) constructing an improved pentose and hexose-fermenting yeast comprising one or more of said genetic permutations.

S. cerevisiae has an inherent preference for glucose. As a consequence, all current pentose fermenting strains demonstrate sequential utilisation of mixtures of glucose and pentoses or at best the pentose fermentation starts at low glucose concentrations. This results in long fermentation times which is economically unfavourable. The claimed method makes it possible to obtain a yeast which is able to simultaneously consume both a pentose and a hexose, resulting in shorter fermentation times.

In the context of this disclosure "simultaneous" or simultaneously" is understood to mean that, at least during part of a fermentation process comprising such yeast, a pentose and a hexose are consumed concomitantly. The yeast produced in the method of the invention is typically able to consume pentoses and hexoses at least in the initial phase of a fermentation. However, it is also possible, i.e. within the scope of the invention, that hexose consumption stops (e.g. because when it is depleted or when the concentration is too low) whilst pentose consumption continues.

The terms "pentose" and "pentose sugar", and, likewise "hexose" and "hexose sugar" have the same meaning and may be used intermittently. The pentose may be for example includes xylose, ribose, and arabinose, or derivatives thereof. Preferred pentose sugars are L-arabinose and D-xylose. The hexose may for example include glucose, galactose, and mannose, preferably glucose and galactose, more preferably glucose. In one embodiment the pentose is L-arabinose and the hexose is glucose. In another embodiment the pentose is D-xylose and the hexose is glucose. In yet another embodiment the pentose include D-xylose and L-arabinose and the hexose is glucose.

A yeast which is not able to grow on only one of hexose or pentose sugar may also be referred to as a yeast which is not able to grow on only a hexose sugar or only a pentose sugar.

Pentose Metabolic Pathway Enzymes

The yeast subjected to evolutionary engineering comprises one or more heterologous genes encoding an enzyme of a pentose metabolic pathway.

In an embodiment the pentose metabolic pathway is the non-oxidative phase of the pentose phosphate pathway, from ribulose-5-phosphate to fructose-6-phosphate and glyceraldehyde-3-phosphate, In an embodiment, the one or more heterologous genes encoding an enzyme of a pentose metabolic pathway comprises a gene encoding a xylose isomerase (XI, EC 5.3.1.5) and a gene encoding a xylulose kinase (XKS, EC 2.7.1.17).

In another embodiment the one or more heterologous genes encoding an enzyme of a pentose metabolic pathway comprises a gene encoding a xylose reductase (XR, EC 1.1.1.307) and a gene encoding a xylitol dehydrogenase (EC 1.1.1.B19).

In another embodiment the one or more heterologous genes encoding an enzyme of a pentose metabolic pathway comprises a gene encoding an arabinose isomerase (araA, EC 5.3.1.4), a gene encoding a ribulokinase (araB, EC 2.7.1.16), and a gene encoding a ribulose-5-P-4-epimerase (araD, EC 5.1.3.4).

The skilled person knows how to prepare a yeast comprising one or more heterologous genes encoding an enzyme of a pentose metabolic pathway. For example, WO2008/041840 describes how to prepare a yeast which expresses araA, araB and araD genes whereby the expression of these nucleotide sequences confers on the cell the ability to use L-arabinose and/or convert L-arabinose into L-ribulose, and/or xylulose 5-phosphate and/or into a desired fermentation product such as ethanol. WO2003/062430 describes how to prepare a yeast which expresses nucleotide sequences encoding xylose isomerase and D-xylukinase, whereby the expression of these nucleotide sequences confers on the cell the ability to consume and convert D-xylose. WO2012/138942 describes how to prepare a yeast which expresses nucleotide sequences encoding D-xylose reductase and xilitol reductase, whereby the expression of these nucleotide sequences confers on the cell the ability to consumed and convert D-xylose.

A "xylose isomerase" is herein defined as an enzyme that catalyses the direct isomerisation of D-xylose into D-xylulose and/or vice versa. The enzyme is also known as a D-xylose ketoisomerase. A xylose isomerase herein may also be capable of catalysing the conversion between D-glucose and D-fructose (and accordingly may therefore be referred to as a glucose isomerase). A xylose isomerase herein may require a bivalent cation, such as magnesium, manganese or cobalt as a cofactor.

The enzyme "xylulose kinase" is herein defined as an enzyme that catalyses the reaction ATP+D-xylulose=ADP+D-xylulose 5-phosphate. The enzyme is also known as a phosphorylating xylulokinase, D-xylulokinase or ATP:D-xylulose 5-phosphotransferase.

A "xylose reductase" (XR) is herein defined as an enzyme that catalyses the reduction of xylose to xylitol.

A "xylitol dehydrogenase" (XDH) is herein defined as an enzyme that catalyses the oxidation of xylitol to xylulose.

An "arabinose isomerase" is herein defined as an enzyme that catalyses at least the conversion of arabinose to ribulose.

A "ribulokinase" is herein defined as an enzyme that catalyses at least the conversion of ribulose to ribulose-5-phosphate.

A "ribulose-5-P-4-epimerase" is herein defined as an enzyme that catalyses at least the conversion of L-ribulose-5-phosphate to D-xylulose-5-phosphate. In an embodiment the araA, araB, and araB genes originate from *Lactobacillus*, preferably from *L. plantarum*.

In an embodiment the xylose isomerase has an amino acid sequence according to SEQ ID NO: 9, or it is a functional homogue thereof having an amino acid sequence having at least 50%, at least 60%, at least 70% sequence identity with SEQ ID NO: 9; preferably at least 80%, at least 85%, 90%, at least 95%, at least 98%, at least 99% sequence identity with SEQ ID NO: 9, or it is a functional homologue which is derived, by way of one or more amino acid substitutions, deletions or insertions, from the amino acid sequence of SEQ ID NO: 9.

In an embodiment the xylulose kinase has an amino acid sequence according to SEQ ID NO: 10, or it is a functional homogue thereof having an amino acid sequence having at least 50%, at least 60%, at least 70% sequence identity with SEQ ID NO: 10; preferably at least 80%, at least 85%, 90%, at least 95%, at least 98%, at least 99% sequence identity with SEQ ID NO: 10, or it is a functional homologue which is derived, by way of one or more amino acid substitutions, deletions or insertions, from the amino acid sequence of SEQ ID NO: 10.

In an embodiment the xylose reductase has an amino acid sequence according to SEQ ID NO: 11, or it is a functional homogue thereof having an amino acid sequence having at least 50%, at least 60%, at least 70% sequence identity with SEQ ID NO: 11 preferably at least 80%, at least 85%, 90%, at least 95%, at least 98%, at least 99% sequence identity with SEQ ID NO: 11, or it is a functional homologue which is derived, by way of one or more amino acid substitutions, deletions or insertions, from the amino acid sequence of SEQ ID NO: 11.

In an embodiment the xylitol dehydrogenase has an amino acid sequence according to SEQ ID NO: 12, or it is a functional homogue thereof having an amino acid sequence having at least 50%, at least 60%, at least 70% sequence identity with SEQ ID NO: 12; preferably at least 80%, at least 85%, 90%, at least 95%, at least 98%, at least 99% sequence identity with SEQ ID NO: 12, or it is a functional homologue which is derived, by way of one or more amino acid substitutions, deletions or insertions, from the amino acid sequence of SEQ ID NO: 12.

In an embodiment the arabinose isomerase has an amino acid sequence according to SEQ ID NO: 13, or it is a functional homogue thereof having an amino acid sequence having at least 50%, at least 60%, at least 70% sequence identity with SEQ ID NO: 13; preferably at least 80%, at least 85%, 90%, at least 95%, at least 98%, at least 99% sequence identity with SEQ ID NO: 13, or it is a functional homologue which is derived, by way of one or more amino acid substitutions, deletions or insertions, from the amino acid sequence of SEQ ID NO: 13.

In an embodiment the ribulokinase has an amino acid sequence according to SEQ ID NO: 14, or it is a functional homogue thereof having an amino acid sequence having at least 50%, at least 60%, at least 70% sequence identity with SEQ ID NO: 14; preferably at least 80%, at least 85%, 90%, at least 95%, at least 98%, at least 99% sequence identity with SEQ ID NO: 14, or it is a functional homologue which is derived, by way of one or more amino acid substitutions, deletions or insertions, from the amino acid sequence of SEQ ID NO: 14.

In an embodiment the ribulose-5-P-4-epimerase has an amino acid sequence according to SEQ ID NO: 15, or it is a functional homogue thereof having an amino acid sequence having at least 50%, at least 60%, at least 70% sequence identity with SEQ ID NO: 15; preferably at least 80%, at least 85%, 90%, at least 95%, at least 98%, at least 99% sequence identity with SEQ ID NO: 15, or it is a functional homologue which is derived, by way of one or more amino acid substitutions, deletions or insertions, from the amino acid sequence of SEQ ID NO: 15.

Disruption of a Gene Encoding a Ribulose-Phosphate 3-Epimerase and Glucose-6-Phosphate Isomerase The yeast subjected to evolutionary engineering comprises a disruption of a gene (i.e. one or more genes) encoding a ribulose-phosphate 3-epimerase and a gene (i.e. one or more genes) encoding a glucose-6-phosphate isomerase.

"Disruption" is herein understood to mean any disruption of activity, and includes, but is not limited to deletion, mutation, reduction of the affinity of the disrupted gene and expression of antisense RNA complementary to corresponding mRNA, and silencing with a 'dead' Cas9 or other non-catalytic endonuclease.

In the context of the invention a ribulose-phosphate 3-epimerase (EC 5.1.3.1) is able to convert D-ribulose-5-phosphate to D-xylulose-5-phosphate. In an embodiment the gene encoding a ribulose-phosphate 3-epimerase encodes a polypeptide having an amino acid sequence according to SEQ ID NO: 1 or it is a functional homogue thereof having an amino acid sequence having at least 50%, at least 60%, at least 70% sequence identity with SEQ ID NO: 1; preferably at least 80%, at least 85%, 90%, at least 95%, at least 98%, at least 99% sequence identity with SEQ ID NO: 1. Preferably the disrupted gene encoding a ribulose-phosphate 3-epimerase is RPE1.

In the context of the invention a glucose-6-phosphate isomerase (E.C. 5.3.1.9) is capable of converting D-glucose-6-phosphate to D-fructose-6-phosphate. In one embodiment the gene encoding a glucose-6-phosphate isomerase encodes a polypeptide having an amino acid sequence according to SEQ ID NO: 2 or it is a functional homogue thereof having an amino acid sequence having at least 50%, at least 60%, at least 70% sequence identity with SEQ ID NO: 2; preferably at least 80%, at least 85%, 90%, at least 95%, at least 98%, at least 99% sequence identity with SEQ ID NO: 2, or it is a functional homologue which is derived, by way of one or more amino acid substitutions, deletions or insertions, from the amino acid sequence of SEQ ID NO: 2. Preferably, the disrupted gene encoding a glucose-6-phosphate isomerase is PGI1.

Since deletion of glucose-6-phosphate isomerase blocks glycolysis, strains with a disrupted glucose-6-phosphate isomerase cannot grow on glucose as the sole carbon source unless all glucose-6-phosphate is rerouted through the pentose-phosphate pathway.

Pentose Phosphate Pathway Enzymes

In the yeast subjected to evolutionary engineering one or more endogenous genes encoding an enzyme of the pentose phosphate pathway are overexpressed. Preferred genes to be overexpressed include a gene encoding 6-phosphogluconolactonase, an enzyme capable to convert 6-phospho-D-glucono-1,5-lactone+$H_2O$ to 6-phospho-D-gluconate (EC 3.1.1.31, e.g. SOL3,) and a gene encoding glucose-6-phosphate 1-dehydrogenase, an enzyme capable to convert D-glucose 6-phosphate+$NADP^+$ to 6-phospho-D-glucono-1,5-lactone+$NADPH+H^+$ (EC 1.1.1.49 e.g. ZWF1).

In an embodiment the one or more endogenous genes encoding an enzyme of the pentose phosphate pathway encodes a polypeptide having an amino acid sequence according to SEQ ID NO: 7, or it is a functional homogue thereof having an amino acid sequence having at least 50%, at least 60%, at least 70% sequence identity with SEQ ID NO: 7; preferably at least 80%, at least 85%, 90%, at least 95%, at least 98%, at least 99% sequence identity with SEQ ID NO: 7, or it is a functional homologue which is derived, by way of one or more amino acid substitutions, deletions or insertions, from the amino acid sequence of SEQ ID NO: 7.

In an embodiment the one or more endogenous genes encoding an enzyme of the pentose phosphate pathway encodes a polypeptide having an amino acid sequence according to SEQ ID NO: 8, or it is a functional homogue thereof having an amino acid sequence having at least 50%, at least 60%, at least 70% sequence identity with SEQ ID NO: 8; preferably at least 80%, at least 85%, 90%, at least 95%, at least 98%, at least 99% sequence identity with SEQ ID NO: 8, or it is a functional homologue which is derived, by way of one or more amino acid substitutions, deletions or insertions, from the amino acid sequence of SEQ ID NO: 8.

Preferably also one or more genes encoding transketolase (e.g. TKL1, TKL2), one or more genes encoding transaldolase (e.g. TAL1, NQM1) and/or one or more genes encoding a ribulose-5-phosphate isomerase (e.g. RKI1) are overexpressed.

In a preferred embodiment, the following endogenous pentose phosphate pathway genes are overexpressed: ZWF1, SOL3, TKL1, TKL2, TAL1, NQM1 and RKI1.

Optional Disruption of NADPH Dependent 6-Phosphogluconate Dehydrogenase

Disruption of the ribulose-phosphate 3-epimerase and glucose-6-phosphate isomerase genes and the introduction of the pentose metabolic pathway enzyme genes may have a negative impact on $NADP^+$/NADPH redox cofactor balancing. This impact may be reduced by replacing native $NADP^+$ dependent 6-phosphogluconate dehydrogenases (EC 1.1.1.44), an enzyme capable to convert 6-phospho-D-gluconate+$NADP^+$ to D-ribulose 5-phosphate+$CO_2$+$NADPH+H^+$ by a heterologous $NAD^+$-dependent enzyme.

Thus, the yeast which is subjected to evolutionary engineering optionally comprises a disruption of one or more genes encoding an NADPH dependent 6-phosphogluconate dehydrogenase.

In one embodiment the gene encoding an NADPH dependent 6-phosphogluconate dehydrogenase encodes a polypeptide having an amino acid sequence according to SEQ ID NO: 3 or 4 or it is a functional homogue thereof having an amino acid sequence having at least 50%, at least 60%, at least 70% sequence identity with SEQ ID NO: 3 or 4; preferably at least 80%, at least 85%, 90%, at least 95%, at least 98%, at least 99% sequence identity with SEQ ID NO: 3 or 4, or it is a functional homologue which is derived, by way of one or more amino acid substitutions, deletions or insertions, from the amino acid sequence of SEQ ID NO: 3 or 4. The to be disrupted gene encoding an NADPH dependent 6-phosphogluconate dehydrogenase may be GND1 or GND2, or both.

If the yeast comprises a disruption of one or more genes encoding an NADPH dependent 6-phosphogluconate dehydrogenase, the yeast comprises one, preferably multiple more copies of a heterologous gene encoding an NADH-dependent 6-phosphogluconate dehydrogenase.

An example of a heterologous gene encoding an NADH-dependent 6-phosphogluconate dehydrogenase is gndA. In an embodiment such heterologous gene encoding an NADH-dependent 6-phosphogluconate dehydrogenase encodes a polypeptide having an amino acid sequence according to SEQ ID NO: 5 or it is a functional homogue thereof having an amino acid sequence having at least 50%, at least 60%, at least 70% sequence identity with SEQ ID NO: 5; preferably at least 80%, at least 85%, 90%, at least 95%, at least 98%, at least 99% sequence identity with SEQ ID NO: 5, or it is a functional homologue which is derived, by way of one or more amino acid substitutions, deletions or insertions, from the amino acid sequence of SEQ ID NO: 5.

The modifications of the yeast provided in step (a) provides a yeast which is dependent on the simultaneous consumption of both hexose and pentose sugar for its cell growth, and which modified yeast is not able to grow on only one of hexose or pentose sugar. This property makes it suitable to undergo evolutionary engineering in order to prepare a yeast which is able to simultaneously consume pentose and hexose sugars (see next section).

In an embodiment the yeast comprises a NADH dependent glucose-6-phosphate 1-dehydrogenase (in contrast to the NADPH dependent glucose-6-phosphate 1-dehydrogenase ZWF1 which is preferably disrupted).

Step (b)—Evolutionary Engineering

In step (b) the yeast is subjected to evolutionary engineering. In this evolutionary engineering step the yeast is grown on a media comprising a hexose sugar and at least one pentose sugar, selecting for a yeast with improved growth rate when grown on a media comprising a hexose and at least one pentose sugar. In fact, the starting yeast in the evolutionary engineering is not able to grown in a single sugar, so any growth must be the result of co consumption of both pentose and hexose. The evolutionary engineering is preferably carried out aerobically.

The media comprising a hexose sugar and at least one pentose sugar on which the yeast is grown during the evolutionary engineering is not necessarily the same media as the media comprising a hexose and at least one pentose sugar which is used to select for yeast with improved growth rate. In an embodiment, they are the same, or similar media.

Over the course of the evolutionary engineering the pentose and hexose concentrations are preferably incrementally increased as this may enhance the selective pressure.

The skilled person knows how to select for improved growth rate. For example, the evolutionary engineering may be done in a batch fermentor such as a shakeflask, and the growth rate can be monitored visually. Improved growth rate may be measured qualitatively or quantitatively (for example by measuring at the time it requires to obtain a certain cell density). Cell density may be judged qualitatively by eye, or quantitatively by using a spectrophotometer. Yeast having a measurable improved growth rate, as compared to the yeast at the start of the evolutionary engineering, is defined herein as "evolved yeast". For example, one may conduct the evolutionary engineering until a growth rate is obtained which is at least 0.01 $h^{-1}$, or at least 0.02 $h^{-1}$, or at least 0.05 $h^{-1}$, or at least 0.1 $h^{-1}$, or at least 0.15 $h^{-1}$, or at least 0.2 $h^{-1}$.

Growth rate may be determined by growing the yeast in a bioreactor (1 L working volume) on synthetic media (S M, Verduyn et al. 1992), supplemented with a 20 g/L glucose and 10 g/L xylose, stirred at 800 rpm, pH maintained at 6, at 30° C., whereby the reactor is sparged at 0.5 L $min^{-1}$ with nitrogen gas.

Step c—Isolation

Optionally, the evolved yeast is isolated to obtain a single cell isolate. This can be done by methods known in the art, for by streaking on an SM agar plate which contains hexose (e.g. glucose at 10 $gL^{-1}$) and a pentose (such as xylose or arabinose at 20 $gL^{-1}$)

Step (d)—Restoring Disrupted Genes

The method can now proceed in at least two alternative ways. In one embodiment the method comprises step (d), in which the disrupted genes encoding a ribulose-phosphate 3-epimerase and encoding a glucose-6-phosphate isomerase are at least partially restored.

In an embodiment the optionally disrupted gene GND1 is also restored, preferably GND1 and GND2, preferably all disrupted genes are restored, This restores the ability of the yeast to ferment both a hexose sugar or a pentose sugar as sole carbon source. As defined herein, "disruption" includes any disruption of activity, and includes, but is not limited to deletion, mutation, reduction of the affinity of the disrupted gene and expression of antisense RNA complementary to corresponding mRNA. Thus, in the context of step (d) "restoring" means any activity which at least partially reverses the effect of the disruption, preferably to the situation of the yeast before the disruption. The skilled person knows how to restore the genes, for example by expression of the corresponding native S. cerevisiae genes from episomal or centromeric vectors or by their integration into the nuclear genome of the yeast.

Steps (d')-(e)

There is at least one other way to proceed after step (c) to obtain a yeast which is capable of simultaneously fermenting a pentose and a hexose sugar, namely by analysing the genome of the evolved yeast and using this information to introduce, into a "fresh" yeast, the modifications that have been the result of the evolutionary engineering. In this alternative route, instead of proceeding with step (d), the method proceeds with step (d') and further comprises step (e).

Thus, in another embodiment the method proceeds with step (d') and further comprises steps (e).

According to step (d') genetic permutations in at least part of the genome of the optionally isolated evolved yeast are identified by genome sequencing. Such genetic permutations can be identified by comparing the genome of the yeast before and after the step of evolutionary engineering. Genome sequencing may be done with short-read or long-read sequencing technologies. Alternatively, genetic permutations can be identified by amplifying specific genes or coding regions by PCR and subjecting them to Sanger sequencing or other sequencing technologies. Genetic permutations may include but are not limited to point mutations, deletions, insertions and/or chromosomal copy number variations and segmental aneuploidies. Preferably such genetic permutations result in a change of at least one amino acid.

Step (e) provides construction of an improved pentose and hexose-fermenting yeast comprising one or more of said genetic permutations (i.e. genetic permutations which have been identified in step (d')). The yeast used in step (e) is not necessarily the same yeast as provided in step (a). For example, the yeast used in step (e) may be a commercial ethanol yeast such as Ethanol Red which is a *Saccharomyces* yeast commercially available from Lesaffre. One or more single nucleotide polymorphisms which have been identified in step (d') and which are the result of the evolutionary engineering can be introduced into a yeast. Furthermore, one or more heterologous genes encoding an enzyme of a pentose metabolic pathway can be introduced, such as XI and XKS, or XR and XDH, and/or araA, araB, and araD; one or more endogenous genes encoding an enzyme of the pentose phosphate pathway can be overexpressed, preferably ZWF1 and SOL3, more preferably ZWF1, SOL3, TKL1, TKL2, TAL1, NQM1 and RKI1; and optionally, a heterologous gene encoding an NADH-dependent 6-phosphogluconate dehydrogenase is introduced and one or more genes encoding an NADPH dependent 6-phosphogluconate dehydrogenase (GND1 or GND2, or both) are disrupted. These genetic adaptations can be done in any order.

In a further aspect the invention provides a recombinant yeast comprising one or more heterologous genes of a pentose metabolic pathway, which yeast further comprises a gene encoding a variant of a parent (endogenous) polypeptide, wherein the variant comprises an amino acid sequence which, when aligned with the amino acid sequence set out in SEQ ID NO: 6, comprises at least one mutation. This does not require that the variant itself is necessarily a polypeptide with amino acid sequence of SEQ ID NO: 6, but rather that the variant comprises at least one mutation, when aligned with SEQ ID NO: 6.

In an embodiment one or more endogenous genes encoding an enzyme of the pentose phosphate pathway are overexpressed.

All embodiments relating to the one or more heterologous genes of a pentose metabolic pathway; the one or more endogenous genes encoding an enzyme of the pentose phosphate pathway, to the NADH-dependent 6-phosphogluconate dehydrogenase, and to the NADPH-dependent 6-phosphogluconate dehydrogenase as described above in the method of the invention equally apply to the yeast of the invention.

The term "parent polypeptide" refers to the polypeptide relative to which another polypeptide (in casu: the variant) differs by substituting, adding or deleting one or more amino acids. The parent polypeptide may be the polypeptide with amino acid sequence of SEQ ID NO: 6, but it could also be another polypeptide.

The variant and the polypeptide with the amino acid sequence of SEQ ID NO: 6 are aligned by a suitable method which allows comparison of the sequences with each other and identifications of the positions in the amino acid sequence of the variant wherein either the same amino acid is present (identical position), or another amino acid is present (substitution), or one or more extra amino acids are present (insertion or extension) or no amino acid is present (deletion or truncation) if compared with the amino acid sequence set out in SEQ ID NO: 6.

As used herein, the terms "variant, "derivative", "mutant" or "homologue" can be used interchangeably. They can refer to either polypeptides or nucleic acids. The variant includes substitutions, insertions, deletions, truncations, transversions, and/or inversions, at one or more locations relative to a reference sequence. The variant can be made for example by site-saturation mutagenesis, scanning mutagenesis, insertional mutagenesis, random mutagenesis, site-directed mutagenesis, and directed-evolution, as well as various other recombination approaches. The variant may differ from the polypeptide with the amino acid sequence of SEQ ID NO: 6 by one or more amino acid residues and may be defined by their level of primary amino acid sequence homology/identity with a reference polypeptide. Preferably, the variant has at least 70%, at least 75%, at least 80%, at least 85%, at least 90%, at least 91%, at least 92%, at least 93%, at least 94%, at least 95%, at least 96%, at least 97%, at least 98%, or even at least 99% amino acid sequence identity with the polypeptide with the amino acid sequence of SEQ ID NO: 6. Methods for determining percent identity are known in the art and described herein. Generally, the variant retains the characteristic nature of the reference polypeptide, but have altered properties in some specific aspects.

In an embodiment the at least one mutation is a disruptive mutation in a glycogen binding domain. In another embodiment the mutation is at position Asp 225 (D225) when aligned with SEQ ID NO: 6. The mutation may comprises a substitution at position Asp 225. The mutation may comprises a substitution at position D225 to any one of Y, F, W, M, L, I, V, C, P, A, or G. The mutation may comprises a substitution at position D225 to an aromatic residue such as Y, W, or F, preferably Y. This does not necessarily mean that this mutation is at position 225 of the variant itself, but rather that the mutation is at a position which in the polypeptide of SEQ ID NO: 6 occurs where there is an Asp at position 225. In a variant which does not have an amino acid identical to SEQ ID NO:6 such position may have a different numbering, but still correspond to position 225 of SEQ ID NO: 6. Position 225 for all variants can be identified by comparing 3D crystal structures, or by aligning the amino acid sequences, as explained in the specification.

In an embodiment the yeast further comprises a disruption of the endogenous HXK2 gene. WO2012/049170 describes yeast cells having a disrupted HXK2 gene and how to prepare such disruption.

In an embodiment the yeast is selected from the list consisting of *Saccharomyces, Kluyveromyces, Candida, Scheffersomyces, Pichia, Schizosaccharomyces, Hansenula, Ogataea, Kloeckera, Schwanniomyces, Issatchenkia* (such as *I. orientalis*) and *Yarrowia*, preferably the yeast is *Saccharomyces cerevisiae*.

The invention further provides a process for the production of an organic compound comprising:
   fermenting a composition comprising a fermentable carbohydrate in the presence of a recombinant yeast of the invention, thereby forming the organic compound; and
   recovering the organic compound.

In an embodiment the composition comprising a fermentable carbohydrate is a biomass hydrolysate, such as a corn stover or corn fiber hydrolysate. In another embodiment such biomass hydrolysate comprises, or is derived from corn stover and/or corn fiber.

By a "hydrolysate" is meant a polysaccharide-comprising material (such as corn stover, corn starch, corn fiber, or lignocellulosic material, which polysaccharides have been depolymerized through the addition of water to form mono and oligosaccharide sugars. Hydrolysates may be produced by enzymatic or acid hydrolysis of the polysaccharide-containing material.

A biomass hydrolysate may be a lignocellulosic biomass hydrolysate. Lignocellulose herein includes hemicellulose and hemicellulose parts of biomass. Lignocellulose includes lignocellulosic fractions of biomass. Suitable lignocellulosic materials may be found in the following list: orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, switch grass, miscanthus, sweet sorghum, canola stems, soybean stems, prairie grass, gamagrass, foxtail; sugar beet pulp, citrus fruit pulp, seed hulls, cellulosic animal wastes, lawn clippings, cotton, seaweed, trees, softwood, hardwood, poplar, pine, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat midlings, oat hulls, hard or soft wood, organic waste material generated from an agricultural process, forestry wood waste, or a combination of any two or more thereof. Lignocellulose, which may be considered as a potential renewable feedstock, generally comprises the polysaccharides cellulose (glucans) and hemicelluloses (xylans, heteroxylans and xyloglucans). In addition, some hemicellulose may be present as glucomannans, for example in wood-derived feedstocks. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucuronic acid and other hexoses and pentoses occurs under the action of different enzymes acting in concert. In addition, pectins and other pectic substances such as arabinans may make up considerably proportion of the dry mass of typically cell walls from non-woody plant tissues (about a quarter to half of dry mass may be pectins). Lignocellulosic material may be pretreated. The pretreatment may comprise exposing the lignocellulosic material to an acid, a base, a solvent, heat, a peroxide, ozone, mechanical shredding, grinding, milling or rapid depressurization, or a combination of any two or more thereof. This chemical pretreatment is often combined with heat-pretreatment, e.g. between 150-220° C. for 1 to 30 minutes.

The process of the invention may comprise, prior to step (a) the step of pretreating lignocellulosic material, e.g. pretreating corn fibers of corn stover. Such pretreatment step may comprise exposing the material to an acid, a base, a solvent, heat, a peroxide, ozone, mechanical shredding, grinding, milling or rapid depressurization, or a combination of any two or more thereof. This chemical pretreatment is often combined with heat-pretreatment, e.g. between 150-220° C. for 1 to 30 minutes.

Such pretreated material is commonly subjected to enzymatic hydrolysis to release sugars that may be fermented according to the invention. This may be executed with conventional methods, e.g. contacting with cellulases, for instance cellobiohydrolase(s), endoglucanase(s), beta-glucosidase(s) and optionally other enzymes. The conversion with the cellulases may be executed at ambient temperatures or at higher temperatures, at a reaction time to release sufficient amounts of sugar(s). The result of the enzymatic hydrolysis is hydrolysis product comprising C5/C6 sugars, herein designated as the sugar composition.

The fermentation step (a) is conducted anaerobic or micro-anaerobic. An anaerobic fermentation process is herein defined as a fermentation process run in the absence of oxygen or in which substantially no oxygen is consumed, preferably less than about 5, about 2.5 or about 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating $NAD^+$.

The fermentation process is preferably run at a temperature that is optimal for the yeast. Thus, the fermentation process is performed at a temperature which is less than about 50° C., less than about 42° C., or less than about 38° C., preferably at a temperature which is lower than about 35° C., about 33° C., about 30 or about 28° C. and at a temperature which is higher than about 20° C., about 22° C., or about 25° C.

Step (b) of the process of the invention relates to the recovery of the ethanol. For the recovery existing technologies can be are used. Existing methods of recovering ethanol from aqueous mixtures commonly use fractionation and adsorption techniques. For example, a beer still can be used to process a fermented product, which contains ethanol in an aqueous mixture, to produce an enriched ethanol-containing mixture that is then subjected to fractionation (e.g., fractional distillation or other like techniques). Next, the fractions containing the highest concentrations of ethanol can be passed through an adsorber to remove most, if not all, of the remaining water from the ethanol. In an embodiment in addition to the recovery of fermentation product, the yeast may be recycled.

The following non-limiting examples are intended to be purely illustrative.

EXAMPLES

Maintenance of Strains

The CEN.PK lineage of *S. cerevisiae* laboratory strains (Entian and Kötter 2007) was used to construct and evolve all strains used in this study (Table 2). Depending on strain auxotrophies, cultures were grown in YP (10 g $L^{-1}$ yeast extract, 20 g $L^{-1}$ peptone) (BD, Franklin Lakes, N.J.) or synthetic medium (SM) (Verduyn et al. 1992), supplemented with glucose (20 g $L^{-1}$), xylose (20 g $L^{-1}$), a glucose/xylose mixture (10 g $L^{-1}$ of each sugar) or a xylose/fructose/glucose mixture (20, 10 and 1 g $L^{-1}$ respectively). Propagation of *E. coli* XL-1 Blue cultures was performed in LB medium (5 g $L^{-1}$ Bacto yeast extract, 10 g $L^{-1}$ Bacto tryptone, 5 g $L^{-1}$ NaCl, 100 µg $mL^{-1}$ ampicillin). Frozen stock cultures were stored at −80° C., after addition of glycerol (30% v/v final concentration).

Construction of Plasmids and Cassettes

PCR amplification for construction of plasmid fragments and yeast integration cassettes was performed with Phusion High Fidelity DNA Polymerase (Thermo-Scientific, Waltham, Mass.), according to the manufacturer's guidelines. Plasmid assembly was performed in vitro with a Gibson Assembly Cloning kit (New England Biolabs, Ipswich, Mass.), following the supplier's guidelines, or in vivo by transformation of plasmid fragments into yeast cells (Kuijpers et al. 2013). For all constructs, correct assembly was confirmed by diagnostic PCR with DreamTaq polymerase (Thermo-Scientific), following the manufacturer's protocol. Plasmids used and constructed in this work are described in Table 3. All yeast genetic modifications were performed using CRISPR/Cas9-based genome editing (Mans et al. 2015). Unique guide-RNA (gRNA) sequences targeting GRE3, GAL83 and RSP5 were selected from a publicly available list (DiCarlo et al. 2013) and synthesized (Baseclear, Leiden, The Netherlands).

To construct the GRE3-targeting CRISPR-plasmid pUDR204, the plasmid backbone of pMEL11 was PCR amplified using primer combination 5980/5792. The insert fragment, expressing the GRE3-targeting gRNA, was amplified using primer combination 5979/5978 and pMEL11 as template. To construct the RPE1/PGI1 double-targeting CRISPR-plasmid pUDR202, the plasmid backbone and the insert fragment were PCR amplified using primer combinations 5941/6005 and 9269/9401, respectively, using pROS11 as template. Both plasmids were assembled in vitro in yeast and cloned in $E.\ coli$. To construct CRISPR-plasmids for single deletion of GAL83 and RSP5, the plasmid backbone, the GAL83-gRNA insert and the RSP5-gRNA insert were amplified using primer combination 5792/5980, 5979/11270 and 5979/11373, respectively, using pMEL10 as template and assembled in vivo.

To generate ZWF1 and SOL3 overexpression cassettes, promoter regions of ADH1 and ENO1 and the coding regions of ZWF1 and SOL3 (including their terminator regions) were PCR amplified using primer combinations 8956/8960, 8958/8961, 8953/8964 and 8984/8986, respectively, using CEN.PK113-7D genomic DNA as a template. The resulting products were used as templates for fusion-PCR assembly of the pADH1-ZWF1-tZWF1 and pENO1-SOL3-tSOL3 overexpression cassettes with primer combinations 8956/8964 and 8958/8986 respectively, which yielded plasmids pUD426 and pUD427 after ligation to pJET-blunt vectors (Thermo-Scientific) and cloning in $E.\ coli$.

To generate yeast-integration cassettes for overexpression of the major genes of the complete PPP, pADH1-ZWF1-tZWF1, pENO1-SOL3-tSOL3, pPGK1-TKL1-tTKL1, pTEF1-TAL1-tTAL1, pPGI1-NQM1-tNQM1, pTPI1-RKI1-tRKI1 and pPYK1-TKL2-tTKL2 cassettes were PCR amplified using primer combinations 4870/7369, 8958/3290, 3291/4068, 3274/3275, 3847/3276, 4691/3277, 3283/3288, respectively, using plasmids pUD426, pUD427, pUD348, pUD349, pUD344, pUD345 and pUD346, respectively, as templates. To generate yeast-integration cassettes of the genes of the non-oxidative PPP, the pTDH3-RPE1-tRPE1, pPGK1-TKL1-tTKL1, pTEF1-TAL1-tTAL1, pTPI1-RKI1-tRKI1 overexpression cassettes were PCR-amplified using primer pairs 7133/3290, 3291/4068, 3724/3725, 10460/10461, respectively and plasmids pUD347, pUD348, pUD34 and pUD345 as templates.

Yeast-integration cassettes for overexpression of $Piromyces$ sp. xylose isomerase (pTPI1-xylA-tCYC1) were PCR-amplified using primer combinations 6285/7548, 6280/6273, 6281/6270, 6282/6271, 6284/6272, 6283/6275, 6287/6276, 6288/6277 or 6289/6274, using pUD350 as template. Yeast xylulokinase overexpression cassettes (pTEF1-XKS1-tXKS1) were PCR-amplified from pUD353, using primer combination 5920/9029 or 7135/7222. A yeast-integration cassette of pGAL83-gal83::GAL83G$^{673T}$-tGAL83 was PCR-amplified from genomic DNA of IMS0629, using primer combination 11273/11274.

Strain Construction

Yeast transformation was performed as previously described (Gietz and Woods 2002). Transformation mixtures were plated on SM or YP agar plates (2% Bacto Agar, BD), supplemented with the appropriate carbon sources. For transformations with the amdS marker cassette, agar plates were prepared and counter selection was performed as previously described (Solis-Escalante et al. 2013). For transformations with the URA3 selection marker counter-selection was performed using 5-fluoro-orotic acid (Zymo Research, Irvine, Calif.), following the supplier's protocol. For transformations with the hphNT marker, agar plates were additionally supplemented with 200 mg L$^{-1}$ hygromycin B (Invivogen, San Diego, Calif.) and plasmid loss was induced by cultivation in non-selective medium. After each transformation, correct genotypes were confirmed by diagnostic PCR using DreamTaq polymerase (Thermo-Scientific, see Table 1 for primer sequences).

Co-transformation of pUDR204 along with the pADH1-ZWF1-tZWF1, pENO1-SOL3-tSOL3, pPGK1-TKL1-tTKL1, pTEF1-TAL1-tTAL1, pPGI1-NQM1-tNQM1, pTPI1-RKI1-tRKI1 and pPYK1-TKL2-tTKL2 integration cassettes to IMX705 (Papapetridis et al. 2016) and subsequent plasmid counter-selection, yielded strain IMX963, which overexpresses the major enzymes of the PPP. Co-transformation of pUDR119, 9 copies of the pTPI1-xylA-tCYC1 integration cassette, along with a single copy of the pTEF1-XKS1-tXKS1 cassette, to IMX963, followed by plasmid counterselection yielded the xylose-fermenting strain IMX990. In IMX990, the pTPI1-xylA-tCYC1 cassettes recombined in vivo to form a multi-copy construct of xylose isomerase overexpression (Verhoeven et al. 2017). To construct IMX1046, in which RPE1 and PG/I were deleted, plasmid pUDR202 and the repair oligonucleotides 9279/9280/9281/9282 were co-transformed to IMX990. Transformation mixes of IMX1046 were plated on SM agar supplemented with a xylose/fructose/glucose mixture (20, 10 and 1 g L$^{-1}$ final concentrations respectively), to avoid potential glucose toxicity (Boles et al. 1993).

To construct strain IMX994, plasmid pUDE335 was co-transformed to IMX581, along with the pTDH3-RPE1-tRPE1, pPGK1-TKL1-tTKL1, pTEF1-TAL1-tTAL1, pTPI1-RKI1-tRKI1 and pTEF1-XKS1-tXKS1 integration cassettes, after which the CRISPR plasmid was recycled. Transformation of pAKX002 to IMX994 yielded the xylose-fermenting strain IMU079. Co-transformation of pUDE327 along with the repair oligonucleotides 5888/5889 to IMX994 yielded strain IMX1384, in which HXK2 was deleted. Co-transformation of the pMEL10 backbone fragment, along with the GAL83-gRNA insert or the RSP5-gRNA insert and repair oligonucleotides 11271/11272 or 11374/11375, respectively, yielded strains IMX1385 (GAL83 deletion) and IMX1442 (RSP5 deletion). Counterselection of the CRISPR plasmids from IMX1384, IMX1385 and IMX1442 yielded, respectively, strains IMX1408, IMX1409 and IMX1451. Transformation of pAKX002 to IMX1408, IMX1409 and IMX1451 yielded, respectively, the xylose-fermenting strains IMX1485, IMX1486 and IMX1487. To construct strain IMX1453, in which the mutated GAL83G$^{673T}$ gene replaced the wild-type GAL83 allele, plasmid pUDR105 was co-transformed to IMX1409 with the pGAL83-gal83::GAL83G$^{673T}$-tGAL83 cassette. Transformation of pAKX002 to IMX1453 yielded the xylose-fermenting strain IMX1488. To construct the hxk2Δ rsp5Δ strain IMX1484, plasmid pUDE327 was co-transformed to IMX1451, along with the repair oligonucleotides 5888/5889. Counterselection of pUDE327 from IMX1484 yielded strain IMX1510. Transformation of pAKX002 to IMX1510 yielded the xylose-fermenting strain IMX1515. To construct the hxk2Δ gal83::GAL83$^{G673T}$ strain IMX1563, plasmid pUDE327 along with the repair-oligonucleotides 5888/5889 was co-transformed to IMX1453. Counterselection of pUDE327 from IMX1563 yielded IMX1571. The xylose-fermenting strain IMX1583 was obtained by transformation of pAKX002 to IMX1571.

Cultivation and Media

Shake-flask growth experiments were performed in 500-mL conical shake flasks containing 100 mL of SM with urea as nitrogen source (2.3 g L$^{-1}$ urea, 6.6 g L$^{-1}$ K$_2$SO$_4$, 3 g L$^{-1}$ KH$_2$PO$_4$, 1 mL L$^{-1}$ trace elements solution (Verduyn et al. 1992) and 1 mL L$^{-1}$ vitamin solution (Verduyn et al. 1992) to prevent medium acidification. The initial pH of the medium was set to 6 by addition of 2 mol L$^{-1}$ KOH. Depending on the strains grown, different mixtures of carbon sources (glucose/xylose/fructose) were added and media were filter-sterilized (0.2 μm, Merck, Darmstadt, Germany). The temperature was set to 30° C. and the stirring speed to 200 rpm in an Innova incubator (New Brunswick Scientific, Edison, EJ). In each case, pre-culture shake-flasks were inoculated from frozen stocks. After 8-12 h of growth, exponentially growing cells from the initial shake-flasks were used to inoculate fresh cultures that, after 12-18 h of growth, were used as inoculum for the growth experiments, to a starting OD660 of 0.4-0.5 in the case of shake-flask growth experiments and of 0.2-0.3 in the case of bioreactor cultivation.

Bioreactor cultures were grown on SM (Verduyn et al. 1992), supplemented with a glucose/xylose mixture (10 g L$^{-1}$ each for aerobic cultivation or 20 g L$^{-1}$/10 g L$^{-1}$ for anaerobic cultivation). Sterilization of mineral media was performed by autoclaving at 121° C. for 20 min. Sugar solutions were sterilized separately by autoclaving at 110° C. for 20 min and added to the sterile salt media along with filter-sterilized vitamin solution. In the case of anaerobic cultivation, media were additionally supplemented with ergosterol (10 mg L$^{-1}$) and Tween 80 (420 mg L$^{-1}$). Sterile antifoam C (0.2 g L$^{-1}$; Sigma-Aldrich, St. Louis, Mo.) was added to all media used for bioreactor cultivation. Batch cultures were grown in 2-L bioreactors (Applikon, Delft, The Netherlands) with a 1-L working volume, stirred at 800 rpm. Culture pH was maintained at 6.0 by automatic addition of 2 mol L$^{-1}$ KOH. Temperature was maintained at 30° C. Bioreactors were sparged at 0.5 L min$^{-1}$ with either pressurized air (aerobic cultivation) or nitrogen gas (<10 ppm oxygen, anaerobic cultivation). All reactors were equipped with Viton O-rings and Norprene tubing to minimize oxygen diffusion. Evaporation in bioreactor cultures was minimized by cooling the off gas outlet to 4° C.

Laboratory Evolution

Laboratory evolution of strain IMX1046 was performed via serial shake-flask cultivation on SM (Verduyn et al. 1992). Cultures were grown in 500-mL shake-flasks with 100 mL working volume. Growth conditions were the same as described above. Initially, the cultures were grown on a glucose/xylose concentration ratio of (1.0 g L$^{-1}$/20 g L$^{-1}$). After growth was observed, exponentially growing cells (0.05 mL of culture) were transferred to SM with a glucose/xylose concentration ratio of 2.0 g L$^{-1}$/20 g L$^{-1}$. During subsequent serial transfers, the glucose content was progressively increased as high growth rates were established at each sugar composition, reaching a final glucose/xylose ratio of 20 g L$^{-1}$/20 g V. At that point three single colonies were isolated from two replicate evolution experiments (IMS0628-630 and IMS0634-636, respectively) by plating on SM with 10 g L$^{-1}$ glucose and 20 g L$^{-1}$ xylose.

Analytical Methods

Off-gas analysis, biomass dry weight measurements, HPLC analysis of culture supernatants and correction for ethanol evaporation in bioreactor experiments were performed as previously described (Papapetridis et al. 2016). Determination of optical density was performed at 660 nm using a Jenway 7200 spectrophotometer (Cole-Palmer, Staffordshire, UK). Yields of products and biomass-specific sugar uptake rates in bioreactor batch cultures were determined as previously described (Wisselink et al. 2009; Papapetridis et al. 2016). Statistical significance of differences in ratios, rates and yields between strains was determined with two-tailed Student's t-tests. All values are represented as averages±mean deviation of independent biological duplicate cultures.

Genome Sequencing

Genomic DNA of strains IMS0629 and IMS0634 was isolated from exponentially growing shake-flask cultures on SM (10 g L$^{-1}$ glucose/20 g L$^{-1}$ xylose) with a Qiagen Blood & Cell culture DNA kit (Qiagen, Germantown, Md.), according to the manufacturer's specifications. Whole-genome sequencing was performed on an Illumina HiSeq PE150 sequencer (Novogene Company Limited, Hong Kong), as follows: DNA was isolated from yeast cells harvested from shakeflask cultures of strains IMS0629 and IMS0634 on synthetic medium (10 g L$^{-1}$ glucose 20 g L$^{-1}$ xylose) using a Qiagen Blood & Cell Culture DNA kit (Qiagen, Germantown, Md.), following manufacturer's specifications. Paired-end sequencing (22 min reads) was performed on a 350-bp PCR-free insert library using an Illumina HiSeq PE150 sequencer (Novogene Company Limited, Hong Kong) with a sample size of 3.3 Gb, accounting for a total coverage of 275×. Sequence data was mapped to the CEN.PK113-7D genome to which the sequences of the gndA and xylA cassettes were manually added. Data processing and chromosome copy number analysis were carried out as described previously by Bracher J M, de Hulster E, Koster C C, van den Broek M, Daran J-M G, van Maris A J A, Pronk J T. Laboratory evolution of a biotin-requiring Saccharomyces cerevisiae strain for full biotin prototrophy and identification of causal mutations. Appl Environ Microbiol. 2017; 83:e00892-17; Verhoeven M D, Lee M, Kamoen L, van den Broek M, Janssen D B, Daran J-M G, van Maris A J A, Pronk J T. Mutations in PMR1 stimulate xylose isomerase activity and anaerobic growth on xylose of engineered Saccharomyces cerevisiae by influencing manganese homeostasis. Sci Rep. 2017; 7:46155; Walker B J, Abeel T, Shea T, Priest M, Abouelliel A, Sakthikumar S, Cuomo C A, Zeng Q, Wortman J, Young S K, Earl A M. Pilon: an integrated tool for comprehensive microbial variant detection and genome assembly improvement. PLoS ONE. 2014; 9:e112963; Li H, Durbin R. Fast and accurate long-read alignment with Burrows-Wheeler transform. Bioinformatics. 2010; 26:589-95; Li H, Handsaker B, Wysoker A, Fennell T, Ruan J, Homer N, Marth G, Abecasis G, Durbin R, Genome Project Data Processing Subgroup. The sequence alignment/map format and SAMtools. Bioinformatics. 2009; 25:2078-9.

Sequence data were mapped to the reference CEN.PK113-7D genome (Nijkamp et al. 2012), to which the sequences of the pTPI1-gndA-tCYC1 and pTPI1-xylA-tCYC1 cassettes were manually added.

Design of an *S. cerevisiae* Strain with a Forced, High Stoichiometry of Xylose and Glucose Co-Consumption Design of an *S. cerevisiae* strain whose growth depended on extensive co-consumption of xylose and glucose was based on the observation that inactivation of PG/1 blocks entry of glucose-6-phosphate into glycolysis, while inactivation of RPE1 prevents entry of ribulose-5-phosphate into the non-oxidative PPP (FIG. 1). As a consequence, a pgi1Δ rpe1Δ strain is unable to grow on glucose. If conversion of xylose into xylulose-5-phosphate in such a strain is enabled by expression of a heterologous xylose isomerase and overexpression of the native xylulose kinase Xks1, co-consumption of xylose and glucose should enable growth (FIG. 1). Overexpression of native genes encoding the enzymes of the non-oxidative PPP has previously been shown to stimulate the required conversion of xylulose-5-phosphate into the glycolytic intermediates fructose-6-phosphate and glyceraldehyde-3-phosphate (FIG. 1). The predicted stoichiometry for conversion of glucose and xylose into pyruvate in a yeast strain that combines these genetic modifications is summarized in Equation 1:

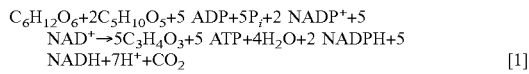

$$C_6H_{12}O_6+2C_5H_{10}O_5+5\ ADP+5P_i+2\ NADP^++5\ NAD^+ \rightarrow 5C_3H_4O_3+5\ ATP+4H_2O+2\ NADPH+5\ NADH+7H^++CO_2 \quad [1]$$

To prevent a potential excessive formation of NADPH (Boles et al. 1993), the strain design further included replacement of the native *S. cerevisiae* NADP$^+$-dependent 6-phosphogluconate dehydrogenases (Gnd1 and Gnd2) by the NAD$^+$-dependent bacterial enzyme GndA, leading to the stoichiometry shown in Equation 2:

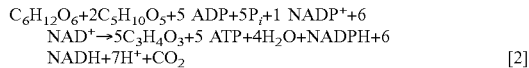

$$C_6H_{12}O_6+2C_5H_{10}O_5+5\ ADP+5P_i+1\ NADP^++6\ NAD^+ \rightarrow 5C_3H_4O_3+5\ ATP+4H_2O+NADPH+6\ NADH+7H^++CO_2 \quad [2]$$

As indicated by Equation 2, this strain design forces co-consumption of 2 mol xylose and 1 mol glucose for the production of 5 mol pyruvate, with a concomitant formation of 1 mol NADPH, 6 mol NADH and 5 mol ATP. NADPH generated in this process can be reoxidized in biosynthetic reactions or via an L-glutamate-2-oxoglutarate transhydrogenase cycle catalysed by Gdh1 and Gdh2 (Boles et al. 1993). Actual in vivo stoichiometries of mixed-sugar consumption will depend on the relative contribution of precursors derived from glucose and xylose to biomass synthesis and on the biomass yield (Verduyn et al. 1990). In aerobic cultures, the latter strongly depends on the mode of NADH reoxidation (mitochondrial respiration, alcoholic fermentation and/or glycerol production).

Construction, Laboratory Evolution and Growth Stoichiometry of Glucose-Xylose Co-Consuming *S. cerevisiae* Strains To implement the proposed strain design for forced co-consumption of xylose and glucose, multiple copies of a codon-optimized expression cassette for *Piromyces* xylA (Verhoeven et al. 2017) were integrated into the genome of *S. cerevisiae* IMX705 (gnd1Δ gnd2Δ gndA; Papapetridis et al. 2016), along with overexpression cassettes for *S. cerevisiae* XKS1 and for structural genes encoding PPP enzymes. Deletion of RPE1 and PGI1 in the resulting xylose-consuming strain IMX990, yielded strain IMX1046, which grew instantaneously in aerobic shake-flask cultures on SM with 1 g L$^{-1}$ glucose and 20 g L$^{-1}$ xylose as sole carbon sources. However, this strain did not grow at the same xylose concentration when the glucose concentration was increased to 10 g L$^{-1}$, indicating kinetic and/or regulatory constraints in glucose-xylose co-consumption at higher glucose concentrations.

To select for co-consumption of xylose at higher glucose concentrations, duplicate serial-transfer experiments were performed in aerobic shake-flask cultures on SM with 20 g L$^{-1}$ xylose. During serial transfer, the glucose concentration in the medium was gradually increased from 1 g L$^{-1}$ to 20 g L$^{-1}$ (FIG. 2). Samples of the evolving cultures were regularly inoculated in SM containing either 20 g L$^{-1}$ glucose or 20 g L$^{-1}$ xylose as sole carbon source. Absence of growth on these single sugars showed that laboratory evolution did not result in 'bypasses' of their forced co-consumption. When, after 13 transfers, vigorous growth was observed on a mixture of 20 g V glucose and 20 g xylose, three single-colony isolates were obtained from each laboratory evolution experiment by streaking on SM agar (10 g L$^{-1}$ glucose/20 g L$^{-1}$ xylose).

Growth studies with the six evolved isolates in shake-flask cultures on SM with 10 g L$^{-1}$ glucose and 20 g L$^{-1}$ xylose, Table 8 identified isolate IMS0629 (Evolution Line 1) as the fastest growing isolate ($\mu$=0.21 h$^{-1}$). The physiology of this strain was further characterized in aerobic bioreactor batch cultures on SM containing 10 g L$^{-1}$ glucose and 20 g L$^{-1}$ xylose. After a 10 h lag phase (FIG. 3, FIG. 5) exponential growth was observed at a specific growth rate of 0.18 h$^{-1}$. Biomass, ethanol and CO$_2$ were the main products, with additional minor formation of glycerol and acetate (Table 4, FIG. 3, FIG. 5). During the exponential growth phase, xylose and glucose were co-consumed at a fixed molar ratio of 1.64 mol mol$^{-1}$ (FIG. 3). Growth ceased after glucose depletion, at which point xylose consumption rates drastically decreased and corresponded to a simultaneous low rate of xylitol formation (FIG. 3, FIG. 5). No production of xylitol was observed during the exponential growth phase. The biomass and ethanol yields on total sugars consumed were 0.28 g biomass (g sugar)$^{-1}$ and 0.18 g ethanol (g sugar)$^{-1}$, respectively. Together with a respiratory quotient of 1.5, these observations indicated a respiro-fermentative sugar dissimilation. In line with the inability of pgi1Δ *S. cerevisiae* to generate glucose-6-phosphate from ethanol and acetate, reconsumption of these fermentation products after glucose depletion was not coupled to growth (FIG. 3, FIG. 5). However, their oxidation may have provided redox equivalents for the observed slow production of xylitol from xylose (FIG. 3).

Whole Genome Sequencing of Evolved Glucose-Xylose Co-Consuming *S. cerevisiae*

To identify causal mutations for the improved growth of the evolved glucose-xylose co-consuming *S. cerevisiae* strains at high glucose concentrations, the genomes of strains IMS0629 and IMS0634 (fastest growing isolates from evolution line 1 and 2, respectively, Table 8) were sequenced and compared to that of their common parental strain. No mutations were found in the coding region of any of the 18 genes encoding these transporters (HXT1-17 and GAL2), or in other known transporter genes. Both evolved strains harboured mutations in HXK2 (Table 5). This gene encodes the major *S. cerevisiae* hexokinase which, in addition to its catalytic role, is involved in glucose repression. The mutation in IMS0629 caused a premature stop codon at position 309 of Hxk2. Both strains also harboured mutations in RSP5, which encodes an E3-ubiquitin ligase linked to ubiquitination and endocytosis of membrane proteins. In strain IMS0629, a substitution at position 686 caused a glycine to aspartic acid change at position 229 of Rsp5 (Table 5). Strain IMS0634 carried a 41 bp internal deletion in RSP5, which included the location of the mutation in strain IMS0629 and probably caused loss of function.

Compared to strain IMS0634, strain IMS0629 harboured 4 additional nucleotide changes in protein-coding regions (Table 5). A G-A change at position 896 of the transcriptional regulator gene CYC8 introduced a stop codon at position 299 of the protein. Deletion of CYC8 was previously shown to enhance xylose uptake in the presence of glucose, albeit at the expense of growth rate. A G-T change at position 673 of the transcriptional regulator gene GAL83 caused an amino acid change from aspartic acid to tyrosine at position 225 of the protein. Gal83 plays a vital role in the function of the Snf1-kinase complex of S. cerevisiae, which is involved in activation of glucose-repressed genes in the absence of the sugar.

Analysis of chromosomal copy number variations showed no chromosomal rearrangements in strain IMS0629. In contrast, strain IMS0634 carried a duplication of the right arm of chromosome 3, a duplication of the middle part of chromosome 8 and a duplication of chromosome 9). The duplications in chromosomes 8 and 9 in IMS0634 spanned the GND1, GRE3 and SGA1 loci at which the expressing cassettes for heterologous genes were integrated (Table 2). In the evolved strains IMS0629 and IMS0634, xylA copy numbers had increased to ca. 27 and 20, respectively. The duplication in of a segment of chromosome 8 in strain IMS0634 also spanned the locations of the low-to-moderate affinity hexose transporter genes HXT1 and HXT5 and the high-affinity hexose transporter gene HXT4.

Mutations in HXK2, RSP5 and GAL83 Stimulate Co-Consumption of Xylose and Glucose in Aerobic Cultures of Xylose-Consuming S. cerevisiae To investigate the impact of mutations in HXK2, RSP5 and/or GAL83 on mixed-sugar utilization by an S. cerevisiae strain without forced glucose-xylose co-consumption, they were introduced into an engineered, non-evolved xylose-consuming S. cerevisiae strain background (Table 2). Over-expression of xylA was accomplished by transforming strains with the multi-copy xylA expression vector pAKX002 (Kuyper et al. 2003). In aerobic shake-flask cultures grown on 10 g $L^{-1}$ glucose and 10 g $L^{-1}$ xylose, the reference strain IMU079 (XKS1↑ PPP↑ pAKX002) displayed a pronounced biphasic growth profile and only a minor co-consumption of the two sugars (0.13 mol xylose (mol glucose)$^{-1}$; Table 6, FIG. 4, FIG. 6). Co-consumption was strongly enhanced in the congenic hxk2Δ strain IMX1485, which showed a 3-fold higher molar ratio of xylose and glucose consumption (0.41). However, its specific growth rate before glucose depletion (0.28 $h^{-1}$) was 13% lower than that of the reference strain (Table 6). Strain IMX1487 (rsp5Δ), which showed a 20% lower specific growth rate than the reference strain, showed a slight improvement in co-consumption (Table 6). Deletion of GAL83 (strain IMX1486) affected neither sugar co-consumption nor growth rate. In contrast, replacement of GAL83 by GAL83$^{G673T}$ (strain IMX1488) resulted in a 40% higher co-consumption of glucose and xylose than observed in the reference strain IMU079, without affecting growth rate (Table 6).

Since independently evolved glucose-xylose co-consuming strains both contained putative loss-of-function mutations in HXK2 and RSP5, both genes were deleted in strain IMX1515 (hxk2Δ rsp5Δ XKS1↑ PPP↑ pAKX002). Similarly, deletion of HXK2 and introduction of GAL83$^{G673T}$ were combined in strain IMX1583 (hxk2Δ gal83::GAL83$^{G673T}$ XKS1↑ PPP↑ pAKX002). Co-consumption ratios in the two strains (0.60 and 0.49 mol xylose (mol glucose)$^{-1}$, respectively) were 4- to 5-fold higher than in the reference strain IMU079 (Table 6, FIG. 4, FIG. 6). However, strain IMX1515 exhibited a 40% lower specific growth rate (0.19 $h^{-1}$) than the reference strain, resulting in a 9 h extension of the fermentation experiments (FIG. 4, FIG. 6). In contrast, strain IMX1583 combined a high co-consumption ratio with the same specific growth rate as that of the reference strain.

Combined Mutations in HXK2 and GAL83 Significantly Accelerate Conversion of Glucose-Xylose Mixtures by Anaerobic Cultures of Xylose-Consuming S. cerevisiae To investigate the impact of the identified mutations under more industrially relevant conditions, anaerobic growth of the reference xylose-fermenting strain IMU079 (XKS1↑ PPP↑ pAKX002) in bioreactor batch experiments was compared with that of the two congenic double mutants IMX1515 (hxk2Δ rsp5Δ) and IMX1583 (hxk2Δ gal83::GAL83$^{G673T}$), that showed the highest glucose-xylose co-consumption in the aerobic shake-flask experiments. The anaerobic cultures were grown on 20 g $L^{-1}$ glucose and 10 g $L^{-1}$ xylose to simulate the relative concentrations of these sugars typically found in lignocellulosic hydrolysates (van Maris et al. 2006).

In the anaerobic batch cultures, strains IMU079, IMX1515 and IMX1583 all produced $CO_2$, biomass, ethanol and glycerol as main products, with a minor production of acetate (Table 7, FIG. 5, Additional File 7). The strains did not produce xylitol during exponential growth and low concentrations of xylitol in cultures of strain IMU079 (2.2±0.1 mmol $L^{-1}$) were only observed at the end of fermentation. As observed in aerobic cultures (FIG. 4), strain IMU079 showed a clear biphasic growth profile in the anaerobic bioreactors (FIG. 5, FIG. 7), during which a fast glucose phase (ca. 16 h) was followed by a much slower and decelerating xylose consumption phase. During the glucose phase, this reference strain maintained a specific growth rate of 0.29 $h^{-1}$ and a glucose-xylose co-consumption ratio of 0.14 mol $mol^{-1}$ (Table 7). After a ca. 30 h lag phase (FIG. 5, FIG. 7), strain IMX1515 exhibited an exponential growth rate of 0.07±0.00 $h^{-1}$, with a high glucose-xylose co-consumption ratio (0.45±0.03 mol $mol^{-1}$). Mainly as a result of its lag phase, strain IMX1515 took longer to consume all sugars than the reference strain IMU079, but its xylose-consumption phase was ca. 65% shorter (ca. 14 h and 43 h, respectively; FIG. 5, FIG. 7).

In contrast to strain IMX1515, strain IMX1583 (hxk2Δ gal83::GAL83$^{G673T}$ XKS1↑ PPP↑ pAKX002) did not exhibit a lag phase but immediately started exponential growth at a specific growth rate of 0.21 $h^{-1}$ (FIG. 5). A comparison of biomass-specific uptake rates of xylose and glucose in the anaerobic batch experiments showed that strain IMX1583 maintained a 44% higher xylose uptake rate than strain IMU079 before glucose exhaustion (Table 7). Moreover, both strains IMX1515 and IMX1583 did not show the pronounced decline of xylose consumption after glucose exhaustion that was observed in the reference strain (FIG. 5, FIG. 7). As a result, the xylose consumption phase in anaerobic cultures of strain IMX1583 was 80% shorter than that strain IMU079 (ca. 9 h compared to 43 h), thereby reducing the time required for complete sugar conversion by over 24 h (FIG. 5).

TABLE 2

Strains.

| Strain name | Relevant Genotype | Origin |
|---|---|---|
| CEN.PK113-7D | MATa MAL2-8c SUC2 CAN1 | (Entian and Kotter 2007) |
| IMX581 | MATa ura3-52 MAL2-8c SUC2 can1::cas9-natN2 | (Mans et al. 2015) |
| IMX705 | MATa MAL2-8c SUC2 can1::cas9-natNT2 gnd2Δ gnd1::gndA | (Papapetridis et al. 2016) |
| IMX963 | MATa MAL2-8c SUC2 can1::cas9-natNT2 gnd2Δ gnd1::gndA gre3::ZWF1, SOL3, TKL1, TAL1, NQM1, RKI1,TKL2 | This disclosure |
| IMX990 | MATa MAL2-8c SUC2 can1::cas9-natNT2 gnd2Δ gnd1:: gndA gre3::ZWF1, SOL3, TKL1, TAL1, NQM1, RKI1,TKL2 sga1::9*xyIA,XKS1 | This disclosure |
| IMX1046 | MATa MAL2-8c SUC2 can1::cas9-natNT2 gnd2Δ gnd1::gndA gre3::ZWF1, SOL3, TKL1, TAL1, NQM1, RKI1,TKL2 sga1::9*xyIA, XKS1 rpe1Δ pgi1Δ | This disclosure |
| IMS0628 | MATa MAL2-8c SUC2 can1::cas9-natNT2 gnd2Δ gnd1::gndA gre3::ZWF1, SOL3, TKL1, TAL1, NQM1, RKI1,TKL2 sga1::9*xyIA, XKS1 rpe1Δ pgi1Δ Evolved isolate 1 | This disclosure |
| IMS0629 | MATa MAL2-8c SUC2 can1::cas9-natNT2 gnd2Δ gnd1::gndA gre3::ZWF1, SOL3, TKL1, TAL1, NQM1, RKI1,TKL2 sga1::9*xyIA, XKS1 rpe1Δ pgi1Δ Evolved isolate 2 | This disclosure |
| IMS0630 | MATa MAL2-8c SUC2 can1::cas9-natNT2 gnd2Δ gnd1::gndA gre3::ZWF1, SOL3, TKL1, TAL1, NQM1, RKI1,TKL2 sga1::9*xyIA, XKS1 rpe1Δ pgi1Δ Evolved isolate 3 | This disclosure |
| IMS0634 | MATa MAL2-8c SUC2 can1::cas9-natNT2 gnd2Δ gnd1::gndA gre3::ZWF1, SOL3, TKL1, TAL1, NQM1, RKI1,TKL2 sga1::9*xyIA, XKS1 rpe1Δ pgi1Δ Evolved isolate 4 | This disclosure |
| IMS0635 | MATa MAL2-8c SUC2 can1::cas9-natNT2 gnd2Δ gnd1::gndA gre3::ZWF1, SOL3, TKL1, TAL1, NQM1, RKI1,TKL2 sga1::9*xyIA, XKS1 rpe1Δ pgi1Δ Evolved isolate 5 | This disclosure |
| IMS0636 | MATa MAL2-8c SUC2 can1::cas9-natNT2 gnd2Δ gnd1::gndA gre3::ZWF1, SOL3, TKL1, TAL1, NQM1, RKI1,TKL2 sga1::9*xyIA, XKS1 rpe1Δ pgi1Δ Evolved isolate 6 | This disclosure |
| IMX994 | MATa ura3-52 MAL2-8c SUC2 can1::cas9-natN2, gre3::RPE1, TKL1, TAL1, RKI1, XKS1 | This disclosure |
| IMU079 | MATa ura3-52 MAL2-8c SUC2 can1::cas9-natN2, gre3::RPE1, TKL1, TAL1, RKI1, XKS1 pAKX002 | This disclosure |
| IMX1384 | MATa ura3-52 MAL2-8c SUC2 can1::cas9-natNT2 gre3::RPE1, TKL1, TAL1, RKI1, XKS1 hxk2Δ pUDE327 | This disclosure |
| IMX1385 | MATa ura3-52 MAL2-8c SUC2 can1::cas9-natNT2 gre3::RPE1, TKL1, TAL1, RKI1, XKS1 gal83ΔPMEL10.GAL83 | This disclosure |
| IMX1442 | MATa ura3-52 MAL2-8c SUC2 can1::cas9-natNT2 gre3::RPE1, TKL1, TAL1, RKI1, XKS1 rsp5Δ PMEL10.RSP5 | This disclosure |
| IMX1408 | MATa ura3-52 MAL2-8c SUC2 can1::cas9-natNT2 gre3::RPE1, TKL1, TAL1, RKI1, XKS1 hxk2Δ | This disclosure |
| IMX1409 | MATa ura3-52 MAL2-8c SUC2 can1::cas9-natNT2 gre3::RPE1, TKL1, TAL1, RKI1, XKS1 gal83Δ | This disclosure |
| IMX1451 | MATa ura3-52 MAL2-8c SUC2 can1::cas9-natNT2 gre3::RPE1, TKL1, TAL1, RKI1, XKS1 rsp5Δ | This disclosure |
| IMX1453 | MATa ura3-52 MAL2-8c SUC2 gre3::RPE1, TKL1, TAL1, RKI1, XKS1 gal83::GAL83$^{G673T}$ | This disclosure |
| IMX1484 | MATa ura3-52 MAL2-8c SUC2 gre3::RPE1, TKL1, TAL1, RKI1, XKS1 rsp5Δ hxk2Δ pUDE327 | This disclosure |
| IMX1485 | MATa ura3-52 MAL2-8c SUC2 gre3::RPE1, TKL1, TAL1, RRKI1, XKS1 hxk2Δ pAKX002 | This disclosure |
| IMX1486 | MATa ura3-52 MAL2-8c SUC2 gre3::RPE1, TKL1, TAL1, RKI1, XKS1 gal83Δ pAKX002 | This disclosure |
| IMX1487 | MATa ura3-52 MAL2-8c SUC2 gre3::RPE1, TKL1, TAL1, RKI1, XKS1 rsp5Δ pAKX002 | This disclosure |
| IMX1488 | MATa ura3-52 MAL2-8c SUC2 gre3::RPE1, TKL1, TAL1, RKI1, XKS1 gal83::GAL83$^{G673T}$ pAKX002 | This disclosure |
| IMX1510 | MATa ura3-52 MAL2-8c SUC2 gre3::RPE1, TKL1, TAL1, RKI1, XKS1 rsp5Δ hxk2Δ | This disclosure |
| IMX1515 | MATa ura3-52 MAL2-8c SUC2 gre3::RPE1, TKL1, TAL1, RKI1, XKS1 rsp5Δ hxk2Δ pAKX002 | This disclosure |
| IMX1563 | MATa ura3-52 MAL2-8c SUC2 gre3::RPE1, TKL1, TAL1, RKI1, XKS1 gal83::GAL83$^{G673T}$ hxk2Δ pUDE327 | This disclosure |
| IMX1571 | MATa ura3-52 MAL2-8c SUC2 gre3::RPE1, TKL1, TAL1, RKI1, XKS1 gal83::GAL83$^{G673T}$ hxk2Δ | This disclosure |
| IMX1583 | MATa ura3-52 MAL2-8c SUC2 gre3::RPE1, TKL1, TAL1, RKI1, XKS1 gal83::GAL83$^{G673T}$ hxk2Δ pAKX002 | This disclosure |

TABLE 3

Plasmids used in this study.

| Plasmid | Characteristics | Origin |
|---|---|---|
| PMEL10 | 2 Mm, KIURA3, pSNR52-gRNA.CAN1-tSUP4 | (Mans et al. 2015) |
| PMEL11 | 2 Mm, amdS, pSNR52-gRNA.CAN1-tSUP4 | (Mans et al. 2015) |
| PROS11 | amdS, gRNA.CAN1-2 Mm ori-gRNA.ADE2 | (Mans et al. 2015) |
| PUDE335 | 2 Mm, KIURA3, pSNR52-gRNA.GRE3-tSUP4 | (Verhoeven et al. 2017) |
| PUD344 | pPGI1-NQM1-tNQM1 PCR template vector | (Verhoeven et al. 2017) |
| PUD345 | pTPI1-RKI1-iRKI1 PCR template vector | (Verhoeven et al. 2017) |

TABLE 3-continued

Plasmids used in this study.

| Plasmid | Characteristics | Origin |
|---|---|---|
| PUD346 | PPYK1-TKL24TKL2 PCR template vector | (Verhoeven et al. 2017) |
| PUD347 | PTDH3-RPE1-tRPE1 PCR template vector | (Verhoeven et al. 2017) |
| PUD348 | pPGK1-TKL1-XTKL1 PCR template vector | (Verhoeven et al. 2017) |
| PUD349 | PTEF1-TAL1-tTAL1 PCR template vector | (Verhoeven et al. 2017) |
| PUD350 | pTPI1-xyIA-tCYC1 PCR template vector | (Verhoeven et al. 2017) |
| PUD353 | PTEF1-XKS1-XXKS1 PCR template vector | (Verhoeven et al. 2017) |
| PUD426 | pADH1-ZWF1-XZWF1 PCR template vector | This work |
| PUD427 | pENO1-SOL3-XSOL3 PCR template vector | This work |
| PUDR119 | 2 Mm ori, amdS, pSNR52-gRNA.SGA1-tSUP4 | Papapetridis et al 2018 |
| PUDR202 | amdS, gRNA.RPE1-2 Mm ori-gRNA.PGI7 | This work |
| PUDR204 | 2 Mm ori, amdS, pSNR52-gRNA.GRE3-tSUP4 | This work |
| PUDR105 | hphNT, gRNA.SynthSite-2 Mm ori-gRNA.SynthSite | (van Rossum et al. 2016) |
| PUDE327 | URA3, pSNR52-gRNA.HXK2-tSUP4 | (Kuijpers et al. 2016) |
| PAKX002 | 2 Mm ori, URA3, pTPI1-xyIA-tCYC1 | (Kuyper et al. 2003) |

TABLE 4

Product yields, biomass specific sugar uptake and production rates in aerobic bioreactor batch cultures of evolved strain *S. cerevisiae* IMS0629 (pgi1Δ rpe1Δ gnd1Δ gnd2Δ gndA XyIA XKS1↑ PPP↑) on SM supplemented with 10 g $L^{-1}$ glucose and 20 g $L^{-1}$ xylose (pH 5, 30° C.). Biomass-specific rates, yields and ratios were calculated from samples taken during the mid-exponential growth phase and represent averages ± mean deviation of independent duplicate cultures. Ethanol yields were corrected for evaporation.

| | |
|---|---|
| Growth rate ($h^{-1}$) | 0.18 ± 0.00 |
| Glucose-xylose consumption ratio mol $mol^{-1}$ | 1.65 ± 0.01 |
| Spec. xylose uptake rate mmol (g biomass)$^{-1}$ $h^{-1}$ | 2.52 ± 0.00 |
| Spec. glucose uptake rate mmol (g biomass)$^{-1}$ $h^{-1}$ | 1.54 ± 0.07 |
| Spec. glycerol production rate mmol (g biomass)$^{-1}$ $h^{-1}$ | 0.23 ± 0.01 |
| Spec. ethanol production rate mmol (g biomass)$^{-1}$ $h^{-1}$ | 2.25 ± 0.37 |
| Spec. $CO_2$ production rate mmol (g biomass)$^{-1}$ $h^{-1}$ | 10.43 ± 0.98 |
| Spec. $O_2$ uptake rate mmol (g biomass)$^{-1}$ $h^{-1}$ | 6.87 ± 0.56 |
| Respiratory quotient | 1.52 ± 0.03 |
| Biomass yield g biomass (g sugars)$^{-1}$ | 0.28 ± 0.00 |
| Ethanol yield g (g sugars)$^{-1}$ | 0.18 ± 0.00 |

TABLE 5

Mutations identified by whole-genome sequencing of glucose-xylose co-consuming *S. cerevisiae* strains evolved for fast growth at high glucose concentrations. Gene descriptions were taken from the Saccharomyces Genome Database (yeastqenome.org, Accessed 14-12-2017).

| Strain and gene | Nucleotide change | Amino acid change | Description |
|---|---|---|---|
| IMS0629 | | | |
| CYC8 | G896A | W299 →Stop | General transcriptional co-repressor; acts together with Tup1; also acts as part of a transcriptional co-activator complex that recruits the SWI/SNF and SAGA complexes to promoters; can form the prion [OCT+] |
| GAL83 | G673T | D225Y | One of three possible beta-subunits of the Snf1 kinase complex; allows nuclear localization of the Snf1 kinase complex in the presence of a non-fermentable carbon source |
| RSP5 | G686A | G229D | NEDD4 family E3 ubiquitin ligase; regulates processes including: MVB sorting, the heat shock response, transcription, endocytosis and ribosome stability; ubiquitinates Sec23, Sna3, Ste4, Nfi1, Rpo21 and Sem1; autoubiquitinates; deubiquitinated by Ubp2; regulated by SUMO ligase Siz1, in turn regulates Siz1 p SUMO ligase activity; required for efficient Golgi-to-ER trafficking in COPI mutants |
| HXK2 | C927G | Y309 →Stop | Hexokinase isoenzyme 2; phosphorylates glucose in cytosol; predominant hexokinase during growth on glucose; represses expression of HXK1, GLK1 |
| RBH1 | C190A | Q64K | Putative protein of unknown function; expression is cell-cycle regulated as shown by microarray analysis; potential regulatory target of Mbp1, which binds to the YJL181W promoter region; contains a PH-like domain |
| DCS1 | C636G | Y212→Stop | Non-essential hydrolase involved in mRNA decapping; activates Xrn1; may function in a feedback mechanism to regulate deadenylation, contains pyrophosphatase activity and a HIT (histidine triad) motif; acts as inhibitor of neutral trehalase Nth 1; required for growth on glycerol medium |
| IMS0634 | | | |
| RSP5 | Internal deletion (41 nucleotides) | Frameshift | NEDD4 family E3 ubiquitin ligase; regulates processes including: MVB sorting, the heat shock response, transcription, endocytosis and ribosome stability; ubiquitinates Sec23, Sna3, Ste4, Nfi1, Rpo21 and Sem1; autoubiquitinates; deubiquitinated by Ubp2; regulated by SUMO ligase Siz1, in turn regulates Siz1 p SUMO ligase activity; required for efficient Golgi-to-ER trafficking in COPI mutants |
| HXK2 | G1027C | D343H | Hexokinase isoenzyme 2; phosphorylates glucose in cytosol; predominant hexokinase during growth on glucose; represses expression of HXK1, GLK1 |

TABLE 6

Specific growth rates (M) and ratio of xylose and glucose consumption in aerobic shake-flask cultures of strains IMU079 (XKS1↑ PPP↑ pAKX002), IMX1485 (hkx2Δ XKS1↑ PPP↑ pAKX002), IMX1486 (gal83Δ XKS1↑ PPP↑ pAKX002), IMX1487 (rsp5Δ XKS1↑ PPP↑ pAKX002), IMX1488 (gal83::GAL83$^{G673T}$ XKS1↑ PPP↑ pAKX002), IMX1515 (hxk2Δ rsp5Δ XKS1↑ PPP↑ pAKX002) and IMX1583 (hxk2Δ gal83::GAL83$^{G673T}$ XKS1↑ PPP↑ pAKX002) grown on SM (urea as nitrogen source) with 10 g L$^{-1}$ glucose and 10 g L$^{-1}$ xylose (pH 6, 30° C.). Growth rates and ratios were calculated from samples taken during the mid-exponential growth phase and represent averages ± mean deviation of independent duplicate cultures.

| Strain | Relevant Genotype | M (h$^{-1}$) | Glucose-xylose consumption ratio (mol mol$^{-1}$) |
|---|---|---|---|
| IMU079 | HXK2 RSP5 GAL83 | 0.32 ± 0.01 | 0.13 ± 0.00 |
| IMX1485 | hxk2Δ | 0.28 ± 0.00* | 0.41 ± 0.01* |
| IMX1486 | gal83Δ | 0.31 ± 0.00 | 0.14 ± 0.01 |
| IMX1487 | rsp5Δ | 0.26 ± 0.00* | 0.15 ± 0.00* |
| IMX1488 | gal83::GAL83$^{G673T}$ | 0.31 ± 0.00 | 0.18 ± 0.01* |
| IMX1515 | hxk2Δ rsp5Δ | 0.19 ± 0.00* | 0.60 ± 0.00* |
| IMX1583 | hxk2Δ gal83::GAL83$^{G673T}$ | 0.31 ± 0.00 | 0.49 ± 0.00* |

*($p < 0.05$) denotes statistical significance of value differences between IMU079 and each engineered strain in Student's t-tests.

TABLE 7

Product yields, biomass specific rates and sugar uptake ratios in anaerobic bioreactor batch cultures of strains IMU079 (XKS1↑ PPP↑ pAKX002), IMX1515 (hxk2Δ rsp5ΔXKS1↑ PPP↑ pAKX002) and IMX1583 (hxk2Δ gal83::GAL83$^{G673T}$ XKS1↑ PPP↑ pAKX002) grown on SM supplemented with 20 g L$^{-1}$ glucose and 10 g L$^{-1}$ xylose (pH 5, 30° C.). Rates, yields and ratios were calculated from samples taken during the mid-exponential growth phase and represent averages ± mean deviation of independent duplicate cultures. Ethanol yields were corrected for evaporation.

| Strain | IMU079 | IMX1515 | IMX1583 |
|---|---|---|---|
| Relevant genotype | HXK2 RSP5 GAL83 | hxk2Δ rsp5Δ | hxk2Δ gal83::GAL83$^{G673T}$ |
| M (h$^{-1}$) | 0.29 ± 0.01 | 0.07 ± 0.00* | 0.21 ± 0.00* |
| Spec. xylose uptake rate mmol (g biomass)$^{-1}$ h$^{-1}$ | 2.22 ± 0.14 | 2.50 ± 0.12 | 3.19 ± 0.02* |
| Spec. glucose uptake rate mmol (g biomass)$^{-1}$ h$^{-1}$ | 15.65 ± 0.52 | 5.58 ± 0.08* | 10.09 ± 0.08* |
| Glucose-xylose consumption ratio (mol mol$^{-1}$) | 0.14 ± 0.00 | 0.45 ± 0.03* | 0.32 ± 0.01* |
| Biomass yield on sugars (g biomass g$^{-1}$) | 0.09 ± 0.01 | 0.05 ± 0.00* | 0.09 ± 0.00 |
| Ethanol yield on sugars (g g$^{-1}$) | 0.37 ± 0.00 | 0.43 ± 0.00* | 0.38 ± 0.01 |
| Glycerol yield on sugars (g g$^{-1}$) | 0.10 ± 0.00 | 0.06 ± 0.00* | 0.08 ± 0.00* |
| Ratio glycerol production on biomass production (mmol (g biomass)$^{-1}$) | 11.5 ± 0.60 | 12.0 ± 0.50 | 9.9 ± 0.10 |
| Xylitol production (mmol L$^{-1}$) | 2.22 ± 0.06 | 0.90 ± 0.04* | 0.35 ± 0.04* |

*($p < 0.05$) denotes statistical significance of value differences between IMU079 and each engineered strain in Student's t-tests.

TABLE 8

Specific growth rates (M) in aerobic shake-flask cultures of evolved strains grown on SM (parental IMX1046, pgi1Δ rpe1Δ gnd1Δ gnd2Δ gndA XyIA XKS↑ PPP↑) with 10 g $L^{-1}$ glucose and 20 g $L^{-1}$ xylose (pH 6, 30° C). Growth rates were calculated from samples taken during the mid-exponential growth phase and represent averages ± mean deviation of independent duplicate cultures.

| Strain | | M (h$^{-1}$) |
| --- | --- | --- |
| Evolution Line 1 | IMS0628 | 0.18 ± 0.00 |
| | IMS0629 | 0.21 ± 0.00 |
| | IMS0630 | 0.19 ± 0.01 |
| Evolution Line 2 | IMS0634 | 0.16 ± 0.00 |
| | IMS0635 | 0.14 ± 0.01 |
| | IMS0636 | 0.15 ± 0.01 |

CITATIONS

Entian K-D, Kötter P. 25 yeast genetic strain and plasmid collections. In: Stansfield I, Stark M J R (eds.) Methods in Microbiology, 36: Academic Press, 2007, 629-66.

Entian K-D. Genetic and biochemical evidence for hexokinase PII as a key enzyme involved in carbon catabolite repression in yeast. Molecular and General Genetics 1980; 178:633-7.

Verduyn C, Postma E, Scheffers W A et al. Physiology of Saccharomyces cerevisiae in anaerobic glucose-limited chemostat cultures. Microbiology 1990; 136:395-403.

Verduyn C, Postma E, Scheffers W A et al. Effect of benzoic acid on metabolic fluxes in yeasts: A continuous-culture study on the regulation of respiration and alcoholic fermentation. Yeast 1992; 8:501-17.

Boles E, Lehnert W, Zimmermann F K. The role of the NAD-dependent glutamate dehydrogenase in restoring growth on glucose of a Saccharomyces cerevisiae phosphoglucose isomerase mutant. European Journal of Biochemistry 1993; 217:469-77.

Raamsdonk L M, Diderich J A, Kuiper A et al. Co-consumption of sugars or ethanol and glucose in a Saccharomyces cerevisiae strain deleted in the HXK2 gene. Yeast 2001; 18:1023-33.

Gietz R D, Woods R A. Transformation of yeast by lithium acetate/single-stranded carrier DNA/polyethylene glycol method. In: Guthrie C, Fink G R (eds.) Methods in Enzymology, 350: Academic Press, 2002, 87-96.

Kuyper M, Harhangi H R, Stave A K et al. High-level functional expression of a fungal xylose isomerase: the key to efficient ethanolic fermentation of xylose by Saccharomyces cerevisiae? FEMS Yeast Research 2003; 4:69-78.

Hucka M, Finney A, Sauro H M et al. The systems biology markup language (SBML): a medium for representation and exchange of biochemical network models. Bioinformatics 2003; 19:524-31.

van Maris A J A, Abbott D A, Bellissimi E et al. Alcoholic fermentation of carbon sources in biomass hydrolysates by Saccharomyces cerevisiae: current status. Antonie van Leeuwenhoek 2006; 90:391-418.

Becker S A, Feist A M, Mo M L et al. Quantitative prediction of cellular metabolism with constraint-based models: the COBRA Toolbox. Nature Protocols 2007; 2:727.

Wisselink H W, Toirkens M J, Wu Q et al. Novel evolutionary engineering approach for accelerated utilization of glucose, xylose, and arabinose mixtures by engineered Saccharomyces cerevisiae strains. Applied and Environmental Microbiology 2009; 75:907-14.

Kim S R, Ha S-J, Wei N et al. Simultaneous co-fermentation of mixed sugars: a promising strategy for producing cellulosic ethanol. Trends in Biotechnology 2012; 30:274-82.

Nijkamp J F, van den Broek M, Datema E et al. De novo sequencing, assembly and analysis of the genome of the laboratory strain Saccharomyces cerevisiae CEN.PK113-7D, a model for modern industrial biotechnology. Microbial Cell Factories 2012; 11:36-.

DiCarlo J E, Norville J E, Mali P et al. Genome engineering in Saccharomyces cerevisiae using CRISPR-Cas systems. Nucleic Acids Research 2013; 41:4336-43.

Kuijpers N G, Solis-Escalante D, Bosman L et al. A versatile, efficient strategy for assembly of multi-fragment expression vectors in Saccharomyces cerevisiae using 60 bp synthetic recombination sequences. Microbial Cell Factories 2013; 12:47.

Aung H W, Henry S A, Walker L P. Revising the representation of fatty acid, glycerolipid, and glycerophospholipid metabolism in the consensus model of yeast metabolism. Industrial Biotechnology 2013; 9:215-28.

Solis-Escalante D, Kuijpers N G A, Bongaerts N et al. amdSYM, a new dominant recyclable marker cassette for Saccharomyces cerevisiae. FEMS Yeast Research 2013; 13:126-39.

Farwick A, Bruder S, Schadeweg V et al. Engineering of yeast hexose transporters to transport D-xylose without inhibition by D-glucose. Proceedings of the National Academy of Sciences of the United States of America 2014; 111:5159-64.

Nijland J G, Shin H Y, de Jong R M et al. Engineering of an endogenous hexose transporter into a specific D-xylose transporter facilitates glucose-xylose co-consumption in Saccharomyces cerevisiae. Biotechnology for Biofuels 2014; 7:168.

Mans R, van Rossum H M, Wijsman M et al. CRISPR/Cas9: a molecular Swiss army knife for simultaneous introduction of multiple genetic modifications in Saccharomyces cerevisiae. FEMS Yeast Research 2015; 15:fov004.

Papapetridis I, van Dijk M, Dobbe A P A et al. Improving ethanol yield in acetate-reducing Saccharomyces cerevisiae by cofactor engineering of 6-phosphogluconate dehydrogenase and deletion of ALD6. Microbial Cell Factories 2016; 15:67.

van Rossum H M, Kozak B U, Niemeijer M S et al. Requirements for carnitine shuttle-mediated translocation of mitochondrial acetyl moieties to the yeast cytosol. mBio 2016; 7.

Kuijpers N G A, Solis-Escalante D, Luttik M A H et al. Pathway swapping: toward modular engineering of essential cellular processes. Proceedings of the National Academy of Sciences 2016; 113:15060-5.

Verhoeven M D, Lee M, Kamoen L et al. Mutations in PMR1 stimulate xylose isomerase activity and anaerobic growth on xylose of engineered Saccharomyces cerevisiae by influencing manganese homeostasis. Scientific Reports 2017; 7:46155.

Papapetridis I, Goudriaan M, Vázquez Vitali M, de Keijzer N A, van den Broek M, van Maris A J A and Pronk J T. Optimizing anaerobic growth rate and fermentation kinetics in Saccharomyces cerevisiae strains expressing Calvin-cycle enzymes for improved ethanol yield, Biotechnology for Biofuels 2018, 11:17.

The invention claimed is:

1. A *Saccharomyces cerevisiae* yeast comprising a mutant GAL83 gene encoding a beta-subunit of the yeast Snf1 kinase complex comprising an amino acid change D225Y when aligned with SEQ ID NO:6.

2. The *Saccharomyces cerevisiae* yeast according to claim 1, wherein the *Saccharomyces cerevisiae* yeast comprises wherein the amino acid change D225Y is the result of a nucleotide change G673T.

3. The *Saccharomyces cerevisiae* yeast according to claim 1, wherein the *Saccharomyces cerevisiae* yeast is a recombinant yeast.

4. The *Saccharomyces cerevisiae* yeast according to claim 1, wherein the *Saccharomyces cerevisiae* yeast comprises one or more overexpressed heterologous genes encoding a xylulokinase enzyme.

5. The *Saccharomyces cerevisiae* yeast according to claim 1, wherein the *Saccharomyces cerevisiae* yeast comprises one or more overexpressed endogenous genes encoding an enzyme of the pentose phosphate pathway.

6. The *Saccharomyces cerevisiae* yeast according to claim 1, wherein the *Saccharomyces cerevisiae* yeast comprises a disruption or deletion of the endogenous HXK2 gene.

7. The *Saccharomyces cerevisiae* yeast according to claim 1, wherein the *Saccharomyces cerevisiae* yeast is a hexose-pentose co-consuming *Saccharomyces cerevisiae* yeast.

8. The *Saccharomyces cerevisiae* yeast according to claim 1, wherein the *Saccharomyces cerevisiae* yeast is a glucose-xylose co-consuming *Saccharomyces cerevisiae* yeast.

9. The *Saccharomyces cerevisiae* yeast according to claim 8, wherein the *Saccharomyces cerevisiae* yeast is a *Saccharomyces cerevisiae* yeast with a glucose-xylose consumption ratio of equal to or more than 0.14 mol/mol$^{-1}$.

10. The *Saccharomyces cerevisiae* yeast according to claim 1, having the same specific growth rate as a reference strain not comprising the mutant GAL83 gene.

11. A process for the co-consumption of glucose and xylose, comprising culturing the *Saccharomyces cerevisiae* yeast according to claim 1 in a batch culture.

12. The process according to claim 11, wherein the process is an anaerobic fermentation process.

13. The process according to claim 11, wherein the process yields ethanol.

14. The process according to claim 11, wherein the glucose to xylose consumption ratio is equal to or more than 0.14 mol/mol$^{-1}$.

15. The process according claim 11, wherein the process comprises the fermenting of a composition comprising a lignocellulosic biomass hydrolysate.

16. The *Saccharomyces cerevisiae* yeast according to claim 1, wherein the *Saccharomyces cerevisiae* yeast comprises: one or more overexpressed heterologous genes encoding a xylulokinase enzyme; one or more overexpressed endogenous genes encoding an enzyme of the pentose phosphate pathway; a disruption or deletion of the endogenous HXK2 gene; and a disruption or deletion of the endogenous RSP5 gene.

* * * * *

SEQUENCE LISTING

<160> NUMBER OF SEQ ID NOS: 130

<210> SEQ ID NO 1
<211> LENGTH: 238
<212> TYPE: PRT
<213> ORGANISM: Saccharomyces cerevisiae
<220> FEATURE:
<221> NAME/KEY: MISC_FEATURE
<222> LOCATION: (1)..(238)
<223> OTHER INFORMATION: Ribulose-phosphate 3-epimerase (Sc_RPE1)

<400> SEQUENCE: 1

```
Met Val Lys Pro Ile Ile Ala Pro Ser Ile Leu Ala Ser Asp Phe Ala
1               5                   10                  15

Asn Leu Gly Cys Glu Cys His Lys Val Ile Asn Ala Gly Ala Asp Trp
            20                  25                  30

Leu His Ile Asp Val Met Asp Gly His Phe Val Pro Asn Ile Thr Leu
        35                  40                  45

Gly Gln Pro Ile Val Thr Ser Leu Arg Arg Ser Val Pro Arg Pro Gly
    50                  55                  60

Asp Ala Ser Asn Thr Glu Lys Lys Pro Thr Ala Phe Phe Asp Cys His
65                  70                  75                  80

Met Met Val Glu Asn Pro Glu Lys Trp Val Asp Asp Phe Ala Lys Cys
                85                  90                  95

Gly Ala Asp Gln Phe Thr Phe His Tyr Glu Ala Thr Gln Asp Pro Leu
            100                 105                 110

His Leu Val Lys Leu Ile Lys Ser Lys Gly Ile Lys Ala Ala Cys Ala
        115                 120                 125

Ile Lys Pro Gly Thr Ser Val Asp Val Leu Phe Glu Leu Ala Pro His
    130                 135                 140

Leu Asp Met Ala Leu Val Met Thr Val Glu Pro Gly Phe Gly Gly Gln
145                 150                 155                 160

Lys Phe Met Glu Asp Met Met Pro Lys Val Glu Thr Leu Arg Ala Lys
                165                 170                 175

Phe Pro His Leu Asn Ile Gln Val Asp Gly Gly Leu Gly Lys Glu Thr
            180                 185                 190

Ile Pro Lys Ala Ala Lys Ala Gly Ala Asn Val Ile Val Ala Gly Thr
        195                 200                 205

Ser Val Phe Thr Ala Ala Asp Pro His Asp Val Ile Ser Phe Met Lys
    210                 215                 220

Glu Glu Val Ser Lys Glu Leu Arg Ser Arg Asp Leu Leu Asp
225                 230                 235
```

<210> SEQ ID NO 2
<211> LENGTH: 554
<212> TYPE: PRT
<213> ORGANISM: Saccharomyces cerevisiae
<220> FEATURE:
<221> NAME/KEY: MISC_FEATURE
<222> LOCATION: (1)..(554)
<223> OTHER INFORMATION: glucose-6-phosphate isomerase (pgi1)

<400> SEQUENCE: 2

```
Met Ser Asn Asn Ser Phe Thr Asn Phe Lys Leu Ala Thr Glu Leu Pro
1               5                   10                  15

Ala Trp Ser Lys Leu Gln Lys Ile Tyr Glu Ser Gln Gly Lys Thr Leu
            20                  25                  30

Ser Val Lys Gln Glu Phe Gln Lys Asp Ala Lys Arg Phe Glu Lys Leu
        35                  40                  45
```

```
Asn Lys Thr Phe Thr Asn Tyr Asp Gly Ser Lys Ile Leu Phe Asp Tyr
     50                  55                  60
Ser Lys Asn Leu Val Asn Asp Glu Ile Ile Ala Ala Leu Ile Glu Leu
 65                  70                  75                  80
Ala Lys Glu Ala Asn Val Thr Gly Leu Arg Asp Ala Met Phe Lys Gly
                 85                  90                  95
Glu His Ile Asn Ser Thr Glu Asp Arg Ala Val Tyr His Val Ala Leu
                100                 105                 110
Arg Asn Arg Ala Asn Lys Pro Met Tyr Val Asp Gly Val Asn Val Ala
             115                 120                 125
Pro Glu Val Asp Ser Val Leu Lys His Met Lys Glu Phe Ser Glu Gln
    130                 135                 140
Val Arg Ser Gly Glu Trp Lys Gly Tyr Thr Gly Lys Lys Ile Thr Asp
145                 150                 155                 160
Val Val Asn Ile Gly Ile Gly Gly Ser Asp Leu Gly Pro Val Met Val
                165                 170                 175
Thr Glu Ala Leu Lys His Tyr Ala Gly Val Leu Asp Val His Phe Val
                180                 185                 190
Ser Asn Ile Asp Gly Thr His Ile Ala Glu Thr Leu Lys Val Val Asp
            195                 200                 205
Pro Glu Thr Thr Leu Phe Leu Ile Ala Ser Lys Thr Phe Thr Thr Ala
    210                 215                 220
Glu Thr Ile Thr Asn Ala Asn Thr Ala Lys Asn Trp Phe Leu Ser Lys
225                 230                 235                 240
Thr Gly Asn Asp Pro Ser His Ile Ala Lys His Phe Ala Ala Leu Ser
                245                 250                 255
Thr Asn Glu Thr Glu Val Ala Lys Phe Gly Ile Asp Thr Lys Asn Met
            260                 265                 270
Phe Gly Phe Glu Ser Trp Val Gly Gly Arg Tyr Ser Val Trp Ser Ala
    275                 280                 285
Ile Gly Leu Ser Val Ala Leu Tyr Ile Gly Tyr Asp Asn Phe Glu Ala
290                 295                 300
Phe Leu Lys Gly Ala Glu Ala Val Asp Asn His Phe Thr Gln Thr Pro
305                 310                 315                 320
Leu Glu Asp Asn Ile Pro Leu Leu Gly Gly Leu Leu Ser Val Trp Tyr
                325                 330                 335
Asn Asn Phe Phe Gly Ala Gln Thr His Leu Val Ala Pro Phe Asp Gln
            340                 345                 350
Tyr Leu His Arg Phe Pro Ala Tyr Leu Gln Gln Leu Ser Met Glu Ser
    355                 360                 365
Asn Gly Lys Ser Val Thr Arg Gly Asn Val Phe Thr Asp Tyr Ser Thr
370                 375                 380
Gly Ser Ile Leu Phe Gly Glu Pro Ala Thr Asn Ala Gln His Ser Phe
385                 390                 395                 400
Phe Gln Leu Val His Gln Gly Thr Lys Leu Ile Pro Ser Asp Phe Ile
                405                 410                 415
Leu Ala Ala Gln Ser His Asn Pro Ile Glu Asn Lys Leu His Gln Lys
            420                 425                 430
Met Leu Ala Ser Asn Phe Phe Ala Gln Ala Glu Ala Leu Met Val Gly
    435                 440                 445
Lys Asp Glu Glu Gln Val Lys Ala Glu Gly Ala Thr Gly Gly Leu Val
    450                 455                 460
```

```
Pro His Lys Val Phe Ser Gly Asn Arg Pro Thr Thr Ser Ile Leu Ala
465                 470                 475                 480

Gln Lys Ile Thr Pro Ala Thr Leu Gly Ala Leu Ile Ala Tyr Tyr Glu
            485                 490                 495

His Val Thr Phe Thr Glu Gly Ala Ile Trp Asn Ile Asn Ser Phe Asp
                500                 505                 510

Gln Trp Gly Val Glu Leu Gly Lys Val Leu Ala Lys Val Ile Gly Lys
        515                 520                 525

Glu Leu Asp Asn Ser Ser Thr Ile Ser Thr His Asp Ala Ser Thr Asn
    530                 535                 540

Gly Leu Ile Asn Gln Phe Lys Glu Trp Met
545                 550
```

<210> SEQ ID NO 3
<211> LENGTH: 489
<212> TYPE: PRT
<213> ORGANISM: Saccharomyces cerevisiae
<220> FEATURE:
<221> NAME/KEY: MISC_FEATURE
<222> LOCATION: (1)..(489)
<223> OTHER INFORMATION: NADPH dependent 6-phosphogluconate
      dehydrogenase gnd1

<400> SEQUENCE: 3

```
Met Ser Ala Asp Phe Gly Leu Ile Gly Leu Ala Val Met Gly Gln Asn
1               5                   10                  15

Leu Ile Leu Asn Ala Ala Asp His Gly Phe Thr Val Cys Ala Tyr Asn
            20                  25                  30

Arg Thr Gln Ser Lys Val Asp His Phe Leu Ala Asn Glu Ala Lys Gly
        35                  40                  45

Lys Ser Ile Ile Gly Ala Thr Ser Ile Glu Asp Phe Ile Ser Lys Leu
50                  55                  60

Lys Arg Pro Arg Lys Val Met Leu Leu Val Lys Ala Gly Ala Pro Val
65                  70                  75                  80

Asp Ala Leu Ile Asn Gln Ile Val Pro Leu Leu Glu Lys Gly Asp Ile
                85                  90                  95

Ile Ile Asp Gly Gly Asn Ser His Phe Pro Asp Ser Asn Arg Arg Tyr
            100                 105                 110

Glu Glu Leu Lys Lys Lys Gly Ile Leu Phe Val Gly Ser Gly Val Ser
        115                 120                 125

Gly Gly Glu Glu Gly Ala Arg Tyr Gly Pro Ser Leu Met Pro Gly Gly
130                 135                 140

Ser Glu Glu Ala Trp Pro His Ile Lys Asn Ile Phe Gln Ser Ile Ser
145                 150                 155                 160

Ala Lys Ser Asp Gly Glu Pro Cys Cys Glu Trp Val Gly Pro Ala Gly
                165                 170                 175

Ala Gly His Tyr Val Lys Met Val His Asn Gly Ile Glu Tyr Gly Asp
            180                 185                 190

Met Gln Leu Ile Cys Glu Ala Tyr Asp Ile Met Lys Arg Leu Gly Gly
        195                 200                 205

Phe Thr Asp Lys Glu Ile Ser Asp Val Phe Ala Lys Trp Asn Asn Gly
210                 215                 220

Val Leu Asp Ser Phe Leu Val Glu Ile Thr Arg Asp Ile Leu Lys Phe
225                 230                 235                 240

Asp Asp Val Asp Gly Lys Pro Leu Val Glu Lys Ile Met Asp Thr Ala
                245                 250                 255
```

-continued

```
Gly Gln Lys Gly Thr Gly Lys Trp Thr Ala Ile Asn Ala Leu Asp Leu
            260                 265                 270

Gly Met Pro Val Thr Leu Ile Gly Glu Ala Val Phe Ala Arg Cys Leu
        275                 280                 285

Ser Ala Leu Lys Asn Glu Arg Ile Arg Ala Ser Lys Val Leu Pro Gly
    290                 295                 300

Pro Glu Val Pro Lys Asp Ala Val Lys Asp Arg Glu Gln Phe Val Asp
305                 310                 315                 320

Asp Leu Glu Gln Ala Leu Tyr Ala Ser Lys Ile Ile Ser Tyr Ala Gln
                325                 330                 335

Gly Phe Met Leu Ile Arg Glu Ala Ala Ala Thr Tyr Gly Trp Lys Leu
            340                 345                 350

Asn Asn Pro Ala Ile Ala Leu Met Trp Arg Gly Gly Cys Ile Ile Arg
        355                 360                 365

Ser Val Phe Leu Gly Gln Ile Thr Lys Ala Tyr Arg Glu Glu Pro Asp
    370                 375                 380

Leu Glu Asn Leu Leu Phe Asn Lys Phe Ala Asp Ala Val Thr Lys
385                 390                 395                 400

Ala Gln Ser Gly Trp Arg Lys Ser Ile Ala Leu Ala Thr Thr Tyr Gly
                405                 410                 415

Ile Pro Thr Pro Ala Phe Ser Thr Ala Leu Ser Phe Tyr Asp Gly Tyr
            420                 425                 430

Arg Ser Glu Arg Leu Pro Ala Asn Leu Leu Gln Ala Gln Arg Asp Tyr
        435                 440                 445

Phe Gly Ala His Thr Phe Arg Val Leu Pro Glu Cys Ala Ser Asp Asn
    450                 455                 460

Leu Pro Val Asp Lys Asp Ile His Ile Asn Trp Thr Gly His Gly Gly
465                 470                 475                 480

Asn Val Ser Ser Ser Thr Tyr Gln Ala
                485

<210> SEQ ID NO 4
<211> LENGTH: 492
<212> TYPE: PRT
<213> ORGANISM: Saccharomyces cerevisiae
<220> FEATURE:
<221> NAME/KEY: MISC_FEATURE
<222> LOCATION: (1)..(492)
<223> OTHER INFORMATION: NADPH dependent 6-phosphogluconate
      dehydrogenase gnd2

<400> SEQUENCE: 4

Met Ser Lys Ala Val Gly Asp Leu Gly Leu Val Gly Leu Ala Val Met
1               5                   10                  15

Gly Gln Asn Leu Ile Leu Asn Ala Ala Asp His Gly Phe Thr Val Val
            20                  25                  30

Ala Tyr Asn Arg Thr Gln Ser Lys Val Asp Arg Phe Leu Ala Asn Glu
        35                  40                  45

Ala Lys Gly Lys Ser Ile Ile Gly Ala Thr Ser Ile Glu Asp Leu Val
    50                  55                  60

Ala Lys Leu Lys Lys Pro Arg Lys Ile Met Leu Leu Ile Lys Ala Gly
65                  70                  75                  80

Ala Pro Val Asp Thr Leu Ile Lys Glu Leu Val Pro His Leu Asp Lys
                85                  90                  95

Gly Asp Ile Ile Ile Asp Gly Gly Asn Ser His Phe Pro Asp Thr Asn
            100                 105                 110
```

Arg Arg Tyr Glu Glu Leu Thr Lys Gln Gly Ile Leu Phe Val Gly Ser
            115                 120                 125

Gly Val Ser Gly Gly Glu Asp Gly Ala Arg Phe Gly Pro Ser Leu Met
130                 135                 140

Pro Gly Gly Ser Ala Glu Ala Trp Pro His Ile Lys Asn Ile Phe Gln
145                 150                 155                 160

Ser Ile Ala Ala Lys Ser Asn Gly Glu Pro Cys Cys Glu Trp Val Gly
                165                 170                 175

Pro Ala Gly Ser Gly His Tyr Val Lys Met Val His Asn Gly Ile Glu
            180                 185                 190

Tyr Gly Asp Met Gln Leu Ile Cys Glu Ala Tyr Asp Ile Met Lys Arg
            195                 200                 205

Ile Gly Arg Phe Thr Asp Lys Glu Ile Ser Glu Val Phe Asp Lys Trp
210                 215                 220

Asn Thr Gly Val Leu Asp Ser Phe Leu Ile Glu Ile Thr Arg Asp Ile
225                 230                 235                 240

Leu Lys Phe Asp Asp Val Asp Gly Lys Pro Leu Val Glu Lys Ile Met
                245                 250                 255

Asp Thr Ala Gly Gln Lys Gly Thr Gly Lys Trp Thr Ala Ile Asn Ala
            260                 265                 270

Leu Asp Leu Gly Met Pro Val Thr Leu Ile Gly Glu Ala Val Phe Ala
            275                 280                 285

Arg Cys Leu Ser Ala Ile Lys Asp Glu Arg Lys Ala Ser Lys Leu
290                 295                 300

Leu Ala Gly Pro Thr Val Pro Lys Asp Ala Ile His Asp Arg Glu Gln
305                 310                 315                 320

Phe Val Tyr Asp Leu Glu Gln Ala Leu Tyr Ala Ser Lys Ile Ile Ser
                325                 330                 335

Tyr Ala Gln Gly Phe Met Leu Ile Arg Glu Ala Ala Arg Ser Tyr Gly
            340                 345                 350

Trp Lys Leu Asn Asn Pro Ala Ile Ala Leu Met Trp Arg Gly Gly Cys
            355                 360                 365

Ile Ile Arg Ser Val Phe Leu Ala Glu Ile Thr Lys Ala Tyr Arg Asp
370                 375                 380

Asp Pro Asp Leu Glu Asn Leu Leu Phe Asn Glu Phe Phe Ala Ser Ala
385                 390                 395                 400

Val Thr Lys Ala Gln Ser Gly Trp Arg Arg Thr Ile Ala Leu Ala Ala
                405                 410                 415

Thr Tyr Gly Ile Pro Thr Pro Ala Phe Ser Thr Ala Leu Ala Phe Tyr
            420                 425                 430

Asp Gly Tyr Arg Ser Glu Arg Leu Pro Ala Asn Leu Leu Gln Ala Gln
            435                 440                 445

Arg Asp Tyr Phe Gly Ala His Thr Phe Arg Ile Leu Pro Glu Cys Ala
450                 455                 460

Ser Ala His Leu Pro Val Asp Lys Asp Ile His Ile Asn Trp Thr Gly
465                 470                 475                 480

His Gly Gly Asn Ile Ser Ser Ser Thr Tyr Gln Ala
                485                 490

<210> SEQ ID NO 5
<211> LENGTH: 303
<212> TYPE: PRT
<213> ORGANISM: Methylobacillus flagellatus
<220> FEATURE:
<221> NAME/KEY: MISC_FEATURE

```
<222> LOCATION: (1)..(303)
<223> OTHER INFORMATION: NADH-dependent 6-phosphogluconate dehydrogenase
      gndA

<400> SEQUENCE: 5

Met Lys Leu Ala Ile Ile Gly Leu Gly Lys Met Gly Gly Asn Met Ala
1               5                   10                  15

Arg Arg Leu Leu Lys His Gly Ile Glu Val Val Gly Phe Asp Phe Asn
            20                  25                  30

Gln Asp Ala Val Asn Gln Ile Ser Leu Thr Asn Gly Met Ile Pro Ala
        35                  40                  45

Ser Ser Val Glu Asp Ala Val Ser Lys Leu Ser Gly Glu Pro Arg Lys
50                  55                  60

Ile Val Trp Ile Met Leu Pro Ser Gly Asp Ile Thr Glu Asn Gln Ile
65                  70                  75                  80

Lys Asp Leu Val Pro Leu Leu Ser Lys Gly Asp Ile Val Asp Gly
                85                  90                  95

Gly Asn Ser Asn Tyr Lys His Ser Gln Arg Gly Ala Trp Leu Ala
            100                 105                 110

Glu His Gly Ile Glu Phe Ile Asp Cys Gly Thr Ser Gly Gly Ile Trp
        115                 120                 125

Gly Leu Asp Asn Gly Tyr Cys Leu Met Tyr Gly Gly Ser Lys Asp Ala
130                 135                 140

Ala Asp Ala Val Val Pro Ile Met Gln Ala Leu Ala His Ala Asp Arg
145                 150                 155                 160

Gly Trp Ala His Val Gly Pro Val Gly Ser Gly His Phe Thr Lys Met
                165                 170                 175

Ile His Asn Gly Ile Glu Tyr Gly Met Met Gln Ala Phe Ala Glu Gly
            180                 185                 190

Leu Asp Leu Leu Lys Gly Lys Glu Glu Phe Asn Leu Asp Leu Ala Gln
        195                 200                 205

Ile Thr Glu Leu Trp Arg His Gly Ser Val Val Arg Ser Trp Leu Leu
210                 215                 220

Asp Leu Thr Ala Glu Ala Leu His Asp Gln Glu Leu Ser Ala Ile
225                 230                 235                 240

Ala Pro Tyr Val Ala Asp Ser Gly Glu Gly Arg Trp Thr Val Val Glu
                245                 250                 255

Ala Val Asp Gln Gly Val Ala Ala Pro Val Leu Thr Leu Ala Leu Gln
            260                 265                 270

Met Arg Phe Ala Ser Gln Glu Asp Thr Gly Tyr Ser Tyr Lys Leu Leu
        275                 280                 285

Ser Met Met Arg Asn Ala Phe Gly Gly His Ala Val Lys Thr Lys
290                 295                 300

<210> SEQ ID NO 6
<211> LENGTH: 417
<212> TYPE: PRT
<213> ORGANISM: Saccharomyces cerevisiae
<220> FEATURE:
<221> NAME/KEY: MISC_FEATURE
<222> LOCATION: (1)..(600)
<223> OTHER INFORMATION: GAL83

<400> SEQUENCE: 6

Met Ala Gly Asp Asn Pro Glu Asn Lys Asp Ala Ser Met Leu Asp Val
1               5                   10                  15

Ser Asp Ala Ala Ser Asn Thr Thr Ile Asn Gly Lys His Ser Ala Asp
```

```
                 20                  25                  30
        Ser Thr Asn Glu Ala Ser Leu Ala Tyr Thr Phe Ser Gln Met Asn Val
                     35                  40                  45

Asp Asn Pro Asn Glu Leu Glu Pro Gln His Pro Leu Arg His Lys Ser
         50                  55                  60

Ser Leu Ile Phe Asn Asp Asp Asp Asp Glu Ile Pro Pro Tyr Ser
         65                  70                  75                  80

Asn His Ala Glu Asn Gly Ser Gly Glu Thr Phe Asp Ser Asp Asp Asp
                         85                  90                  95

Ile Asp Ala Ser Ser Ser Ser Ile Asp Ser Asn Glu Gly Asp Ile
                    100                 105                 110

His Asp Ala Asp Met Thr Gly Asn Thr Leu Gln Lys Met Asp Tyr Gln
                    115                 120                 125

Pro Ser Gln Gln Pro Asp Ser Leu Gln Asn Gln Gly Phe Gln Gln Gln
                    130                 135                 140

Gln Glu Gln Gln Gln Gly Thr Val Glu Gly Lys Lys Gly Arg Ala Met
        145                 150                 155                 160

Met Phe Pro Val Asp Ile Thr Trp Gln Gln Gly Gly Asn Lys Val Tyr
                            165                 170                 175

Val Thr Gly Ser Phe Thr Gly Trp Arg Lys Met Ile Gly Leu Val Pro
                        180                 185                 190

Val Pro Gly Gln Pro Gly Leu Met His Val Lys Leu Gln Leu Pro Pro
                    195                 200                 205

Gly Thr His Arg Phe Arg Phe Ile Val Asp Asn Glu Leu Arg Phe Ser
                    210                 215                 220

Asp Tyr Leu Pro Thr Ala Thr Asp Gln Met Gly Asn Phe Val Asn Tyr
        225                 230                 235                 240

Met Glu Val Ser Ala Pro Pro Asp Trp Gly Asn Glu Pro Gln Gln His
                            245                 250                 255

Leu Ala Glu Lys Lys Ala Asn His Val Asp Asp Ser Lys Leu Ser Lys
                    260                 265                 270

Arg Pro Met Ser Ala Arg Ser Arg Ile Ala Leu Glu Ile Glu Lys Glu
                    275                 280                 285

Pro Asp Asp Met Gly Asp Gly Tyr Thr Arg Phe His Asp Glu Thr Pro
                    290                 295                 300

Ala Lys Pro Asn Leu Glu Tyr Thr Gln Asp Ile Pro Ala Val Phe Thr
        305                 310                 315                 320

Asp Pro Asn Val Met Glu Gln Tyr Tyr Leu Thr Leu Asp Gln Gln
                            325                 330                 335

Asn Asn His Gln Asn Met Ala Trp Leu Thr Pro Gln Leu Pro Pro
                        340                 345                 350

His Leu Glu Asn Val Ile Leu Asn Ser Tyr Ser Asn Ala Gln Thr Asp
                    355                 360                 365

Asn Thr Ser Gly Ala Leu Pro Ile Pro Asn His Val Ile Leu Asn His
                    370                 375                 380

Leu Ala Thr Ser Ser Ile Lys His Asn Thr Leu Cys Val Ala Ser Ile
        385                 390                 395                 400

Val Arg Tyr Lys Gln Lys Tyr Val Thr Gln Ile Leu Tyr Thr Pro Leu
                            405                 410                 415

Gln

<210> SEQ ID NO 7
<211> LENGTH: 258
```

<212> TYPE: PRT
<213> ORGANISM: Saccharomyces cerevisiae
<220> FEATURE:
<221> NAME/KEY: MISC_FEATURE
<222> LOCATION: (1)..(258)
<223> OTHER INFORMATION: S cerevisiae 6-phosphogluconolactonase (SOL3)

<400> SEQUENCE: 7

Met Ala Ala Gly Val Pro Lys Ile Asp Ala Leu Glu Ser Leu Gly Asn
1               5                   10                  15

Pro Leu Glu Asp Ala Lys Arg Ala Ala Tyr Arg Ala Val Asp Glu
            20                  25                  30

Asn Leu Lys Phe Asp Asp His Lys Ile Ile Gly Ile Gly Ser Gly Ser
            35                  40                  45

Thr Val Val Tyr Val Ala Glu Arg Ile Gly Gln Tyr Leu His Asp Pro
    50                  55                  60

Lys Phe Tyr Glu Val Ala Ser Lys Phe Ile Cys Ile Pro Thr Gly Phe
65                  70                  75                  80

Gln Ser Arg Asn Leu Ile Leu Asp Asn Lys Leu Gln Leu Gly Ser Ile
                85                  90                  95

Glu Gln Tyr Pro Arg Ile Asp Ile Ala Phe Asp Gly Ala Asp Glu Val
            100                 105                 110

Asp Glu Asn Leu Gln Leu Ile Lys Gly Gly Gly Ala Cys Leu Phe Gln
        115                 120                 125

Glu Lys Leu Val Ser Thr Ser Ala Lys Thr Phe Ile Val Val Ala Asp
    130                 135                 140

Ser Arg Lys Lys Ser Pro Lys His Leu Gly Lys Asn Trp Arg Gln Gly
145                 150                 155                 160

Val Pro Ile Glu Ile Val Pro Ser Ser Tyr Val Arg Val Lys Asn Asp
                165                 170                 175

Leu Leu Glu Gln Leu His Ala Glu Lys Val Asp Ile Arg Gln Gly Gly
            180                 185                 190

Ser Ala Lys Ala Gly Pro Val Val Thr Asp Asn Asn Phe Ile Ile
        195                 200                 205

Asp Ala Asp Phe Gly Glu Ile Ser Asp Pro Arg Lys Leu His Arg Glu
    210                 215                 220

Ile Lys Leu Leu Val Gly Val Glu Thr Gly Leu Phe Ile Asp Asn
225                 230                 235                 240

Ala Ser Lys Ala Tyr Phe Gly Asn Ser Asp Gly Ser Val Glu Val Thr
                245                 250                 255

Glu Lys

<210> SEQ ID NO 8
<211> LENGTH: 238
<212> TYPE: PRT
<213> ORGANISM: Saccharomyces cerevisiae
<220> FEATURE:
<221> NAME/KEY: MISC_FEATURE
<222> LOCATION: (1)..(238)
<223> OTHER INFORMATION: S cerevisiae Glucose-6-phosphate
      1-dehydrogenase (ZWF1)

<400> SEQUENCE: 8

Met Val Lys Pro Ile Ile Ala Pro Ser Ile Leu Ala Ser Asp Phe Ala
1               5                   10                  15

Asn Leu Gly Cys Glu Cys His Lys Val Ile Asn Ala Gly Ala Asp Trp
            20                  25                  30

Leu His Ile Asp Val Met Asp Gly His Phe Val Pro Asn Ile Thr Leu

```
                35                  40                  45
Gly Gln Pro Ile Val Thr Ser Leu Arg Arg Ser Val Pro Arg Pro Gly
 50                  55                  60

Asp Ala Ser Asn Thr Glu Lys Lys Pro Thr Ala Phe Phe Asp Cys His
 65                  70                  75                  80

Met Met Val Glu Asn Pro Glu Lys Trp Val Asp Phe Ala Lys Cys
                 85                  90                  95

Gly Ala Asp Gln Phe Thr Phe His Tyr Glu Ala Thr Gln Asp Pro Leu
                100                 105                 110

His Leu Val Lys Leu Ile Lys Ser Lys Gly Ile Lys Ala Ala Cys Ala
                115                 120                 125

Ile Lys Pro Gly Thr Ser Val Asp Val Leu Phe Glu Leu Ala Pro His
130                 135                 140

Leu Asp Met Ala Leu Val Met Thr Val Glu Pro Gly Phe Gly Gly Gln
145                 150                 155                 160

Lys Phe Met Glu Asp Met Met Pro Lys Val Glu Thr Leu Arg Ala Lys
                165                 170                 175

Phe Pro His Leu Asn Ile Gln Val Asp Gly Gly Leu Gly Lys Glu Thr
                180                 185                 190

Ile Pro Lys Ala Ala Lys Ala Gly Ala Asn Val Ile Val Ala Gly Thr
                195                 200                 205

Ser Val Phe Thr Ala Ala Asp Pro His Asp Val Ile Ser Phe Met Lys
210                 215                 220

Glu Glu Val Ser Lys Glu Leu Arg Ser Arg Asp Leu Leu Asp
225                 230                 235

<210> SEQ ID NO 9
<211> LENGTH: 437
<212> TYPE: PRT
<213> ORGANISM: Piromyces sp. E2
<220> FEATURE:
<221> NAME/KEY: MISC_FEATURE
<222> LOCATION: (1)..(437)
<223> OTHER INFORMATION: Xylose isomerase (XI)

<400> SEQUENCE: 9

Met Ala Lys Glu Tyr Phe Pro Gln Ile Gln Lys Ile Lys Phe Glu Gly
 1               5                  10                  15

Lys Asp Ser Lys Asn Pro Leu Ala Phe His Tyr Tyr Asp Ala Glu Lys
                20                  25                  30

Glu Val Met Gly Lys Lys Met Lys Asp Trp Leu Arg Phe Ala Met Ala
                35                  40                  45

Trp Trp His Thr Leu Cys Ala Glu Gly Ala Asp Gln Phe Gly Gly Gly
 50                  55                  60

Thr Lys Ser Phe Pro Trp Asn Glu Gly Thr Asp Ala Ile Glu Ile Ala
 65                  70                  75                  80

Lys Gln Lys Val Asp Ala Gly Phe Glu Ile Met Gln Lys Leu Gly Ile
                 85                  90                  95

Pro Tyr Tyr Cys Phe His Asp Val Asp Leu Val Ser Glu Gly Asn Ser
                100                 105                 110

Ile Glu Glu Tyr Glu Ser Asn Leu Lys Ala Val Val Ala Tyr Leu Lys
                115                 120                 125

Glu Lys Gln Lys Glu Thr Gly Ile Lys Leu Leu Trp Ser Thr Ala Asn
130                 135                 140

Val Phe Gly His Lys Arg Tyr Met Asn Gly Ala Ser Thr Asn Pro Asp
145                 150                 155                 160
```

```
Phe Asp Val Val Ala Arg Ala Ile Val Gln Ile Lys Asn Ala Ile Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Ala Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Phe Val Thr Gly Gly Gly
                325                 330                 335

Thr Asn Phe Asp Ala Lys Thr Arg Arg Asn Ser Thr Asp Leu Glu Asp
            340                 345                 350

Ile Ile Ile Ala His Val Ser Gly Met Asp Ala Met Ala Arg Ala Leu
        355                 360                 365

Glu Asn Ala Ala Lys Leu Leu Gln Glu Ser Pro Tyr Thr Lys Met Lys
    370                 375                 380

Lys Glu Arg Tyr Ala Ser Phe Asp Ser Gly Ile Gly Lys Asp Phe Glu
385                 390                 395                 400

Asp Gly Lys Leu Thr Leu Glu Gln Val Tyr Glu Tyr Gly Lys Lys Asn
                405                 410                 415

Gly Glu Pro Lys Gln Thr Ser Gly Lys Gln Glu Leu Tyr Glu Ala Ile
            420                 425                 430

Val Ala Met Tyr Gln
        435

<210> SEQ ID NO 10
<211> LENGTH: 600
<212> TYPE: PRT
<213> ORGANISM: Saccharomyces cerevisiae
<220> FEATURE:
<221> NAME/KEY: MISC_FEATURE
<222> LOCATION: (1)..(600)
<223> OTHER INFORMATION: Xylulokinase (Xks1p)

<400> SEQUENCE: 10

Met Leu Cys Ser Val Ile Gln Arg Gln Thr Arg Glu Val Ser Asn Thr
1               5                   10                  15

Met Ser Leu Asp Ser Tyr Tyr Leu Gly Phe Asp Leu Ser Thr Gln Gln
            20                  25                  30

Leu Lys Cys Leu Ala Ile Asn Gln Asp Leu Lys Ile Val His Ser Glu
        35                  40                  45

Thr Val Glu Phe Glu Lys Asp Leu Pro His Tyr His Thr Lys Lys Gly
    50                  55                  60
```

```
Val Tyr Ile His Gly Asp Thr Ile Glu Cys Pro Val Ala Met Trp Leu
 65                  70                  75                  80

Glu Ala Leu Asp Leu Val Leu Ser Lys Tyr Arg Glu Ala Lys Phe Pro
                 85                  90                  95

Leu Asn Lys Val Met Ala Val Ser Gly Ser Cys Gln Gln His Gly Ser
                100                 105                 110

Val Tyr Trp Ser Ser Gln Ala Glu Ser Leu Leu Gln Leu Asn Lys
            115                 120                 125

Lys Pro Glu Lys Asp Leu Leu His Tyr Val Ser Ser Val Ala Phe Ala
130                 135                 140

Arg Gln Thr Ala Pro Asn Trp Gln Asp His Ser Thr Ala Lys Gln Cys
145                 150                 155                 160

Gln Glu Phe Glu Glu Cys Ile Gly Gly Pro Glu Lys Met Ala Gln Leu
                165                 170                 175

Thr Gly Ser Arg Ala His Phe Arg Phe Thr Gly Pro Gln Ile Leu Lys
                180                 185                 190

Ile Ala Gln Leu Glu Pro Glu Ala Tyr Glu Lys Thr Lys Thr Ile Ser
                195                 200                 205

Leu Val Ser Asn Phe Leu Thr Ser Ile Leu Val Gly His Leu Val Glu
210                 215                 220

Leu Glu Glu Ala Asp Ala Cys Gly Met Asn Leu Tyr Asp Ile Arg Glu
225                 230                 235                 240

Arg Lys Phe Ser Asp Glu Leu Leu His Leu Ile Asp Ser Ser Ser Lys
                245                 250                 255

Asp Lys Thr Ile Arg Gln Lys Leu Met Arg Ala Pro Met Lys Asn Leu
                260                 265                 270

Ile Ala Gly Thr Ile Cys Lys Tyr Phe Ile Glu Lys Tyr Gly Phe Asn
                275                 280                 285

Thr Asn Cys Lys Val Ser Pro Met Thr Gly Asp Asn Leu Ala Thr Ile
                290                 295                 300

Cys Ser Leu Pro Leu Arg Lys Asn Asp Val Leu Val Ser Leu Gly Thr
305                 310                 315                 320

Ser Thr Thr Val Leu Leu Val Thr Asp Lys Tyr His Pro Ser Pro Asn
                325                 330                 335

Tyr His Leu Phe Ile His Pro Thr Leu Pro Asn His Tyr Met Gly Met
                340                 345                 350

Ile Cys Tyr Cys Asn Gly Ser Leu Ala Arg Glu Arg Ile Arg Asp Glu
                355                 360                 365

Leu Asn Lys Glu Arg Glu Asn Asn Tyr Glu Lys Thr Asn Asp Trp Thr
                370                 375                 380

Leu Phe Asn Gln Ala Val Leu Asp Asp Ser Glu Ser Ser Glu Asn Glu
385                 390                 395                 400

Leu Gly Val Tyr Phe Pro Leu Gly Glu Ile Val Pro Ser Val Lys Ala
                405                 410                 415

Ile Asn Lys Arg Val Ile Phe Asn Pro Lys Thr Gly Met Ile Glu Arg
                420                 425                 430

Glu Val Ala Lys Phe Lys Asp Lys Arg His Asp Ala Lys Asn Ile Val
                435                 440                 445

Glu Ser Gln Ala Leu Ser Cys Arg Val Arg Ile Ser Pro Leu Leu Ser
                450                 455                 460

Asp Ser Asn Ala Ser Ser Gln Gln Arg Leu Asn Glu Asp Thr Ile Val
465                 470                 475                 480

Lys Phe Asp Tyr Asp Glu Ser Pro Leu Arg Asp Tyr Leu Asn Lys Arg
```

```
                    485                 490                 495
Pro Glu Arg Thr Phe Phe Val Gly Gly Ala Ser Lys Asn Asp Ala Ile
                500                 505                 510

Val Lys Lys Phe Ala Gln Val Ile Gly Ala Thr Lys Gly Asn Phe Arg
            515                 520                 525

Leu Glu Thr Pro Asn Ser Cys Ala Leu Gly Gly Cys Tyr Lys Ala Met
        530                 535                 540

Trp Ser Leu Leu Tyr Asp Ser Asn Lys Ile Ala Val Pro Phe Asp Lys
545                 550                 555                 560

Phe Leu Asn Asp Asn Phe Pro Trp His Val Met Glu Ser Ile Ser Asp
                565                 570                 575

Val Asp Asn Glu Asn Trp Asp Arg Tyr Asn Ser Lys Ile Val Pro Leu
            580                 585                 590

Ser Glu Leu Glu Lys Thr Leu Ile
        595                 600

<210> SEQ ID NO 11
<211> LENGTH: 318
<212> TYPE: PRT
<213> ORGANISM: Scheffersomyces stipitis
<220> FEATURE:
<221> NAME/KEY: MISC_FEATURE
<222> LOCATION: (1)..(318)
<223> OTHER INFORMATION: Xylose reductase

<400> SEQUENCE: 11

Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Ile Tyr
            20                  25                  30

Arg Ala Ile Lys Thr Gly Tyr Arg Leu Phe Asp Gly Ala Glu Asp Tyr
        35                  40                  45

Ala Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240
```

```
Ile Lys Ala Ile Ala Ala Lys His Gly Lys Ser Pro Ala Gln Val Leu
                245                 250                 255

Leu Arg Trp Ser Ser Gln Arg Gly Ile Ala Ile Ile Pro Lys Ser Asn
            260                 265                 270

Thr Val Pro Arg Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315

<210> SEQ ID NO 12
<211> LENGTH: 363
<212> TYPE: PRT
<213> ORGANISM: Scheffersomyces stipitis
<220> FEATURE:
<221> NAME/KEY: MISC_FEATURE
<222> LOCATION: (1)..(363)
<223> OTHER INFORMATION: Xylitol dehydrogenase

<400> SEQUENCE: 12

Met Thr Ala Asn Pro Ser Leu Val Leu Asn Lys Ile Asp Asp Ile Ser
1               5                   10                  15

Phe Glu Thr Tyr Asp Ala Pro Glu Ile Ser Glu Pro Thr Asp Val Leu
            20                  25                  30

Val Gln Val Lys Lys Thr Gly Ile Cys Gly Ser Asp Ile His Phe Tyr
        35                  40                  45

Ala His Gly Arg Ile Gly Asn Phe Val Leu Thr Lys Pro Met Val Leu
    50                  55                  60

Gly His Glu Ser Ala Gly Thr Val Val Gln Val Gly Lys Gly Val Thr
65                  70                  75                  80

Ser Leu Lys Val Gly Asp Asn Val Ala Ile Glu Pro Gly Ile Pro Ser
                85                  90                  95

Arg Phe Ser Asp Glu Tyr Lys Ser Gly His Tyr Asn Leu Cys Pro His
            100                 105                 110

Met Ala Phe Ala Ala Thr Pro Asn Ser Lys Glu Gly Glu Pro Asn Pro
        115                 120                 125

Pro Gly Thr Leu Cys Lys Tyr Phe Lys Ser Pro Glu Asp Phe Leu Val
    130                 135                 140

Lys Leu Pro Asp His Val Ser Leu Glu Leu Gly Ala Leu Val Glu Pro
145                 150                 155                 160

Leu Ser Val Gly Val His Ala Ser Lys Leu Gly Ser Val Ala Phe Gly
                165                 170                 175

Asp Tyr Val Ala Val Phe Gly Ala Gly Pro Val Gly Leu Leu Ala Ala
            180                 185                 190

Ala Val Ala Lys Thr Phe Gly Ala Lys Gly Val Ile Val Val Asp Ile
        195                 200                 205

Phe Asp Asn Lys Leu Lys Met Ala Lys Asp Ile Gly Ala Ala Thr His
    210                 215                 220

Thr Phe Asn Ser Lys Thr Gly Gly Ser Glu Glu Leu Ile Lys Ala Phe
225                 230                 235                 240

Gly Gly Asn Val Pro Asn Val Val Leu Glu Cys Thr Gly Ala Glu Pro
                245                 250                 255

Cys Ile Lys Leu Gly Val Asp Ala Ile Ala Pro Gly Gly Arg Phe Val
            260                 265                 270
```

```
Gln Val Gly Asn Ala Ala Gly Pro Val Ser Phe Pro Ile Thr Val Phe
            275                 280                 285

Ala Met Lys Glu Leu Thr Leu Phe Gly Ser Phe Arg Tyr Gly Phe Asn
    290                 295                 300

Asp Tyr Lys Thr Ala Val Gly Ile Phe Asp Thr Asn Tyr Gln Asn Gly
305                 310                 315                 320

Arg Glu Asn Ala Pro Ile Asp Phe Glu Gln Leu Ile Thr His Arg Tyr
                325                 330                 335

Lys Phe Lys Asp Ala Ile Glu Ala Tyr Asp Leu Val Arg Ala Gly Lys
                340                 345                 350

Gly Ala Val Lys Cys Leu Ile Asp Gly Pro Glu
            355                 360
```

<210> SEQ ID NO 13
<211> LENGTH: 474
<212> TYPE: PRT
<213> ORGANISM: Lactobacillus plantarum
<220> FEATURE:
<221> NAME/KEY: MISC_FEATURE
<222> LOCATION: (1)..(474)
<223> OTHER INFORMATION: L-arabinose isomerase (araA)

<400> SEQUENCE: 13

```
Met Leu Ser Val Pro Asp Tyr Glu Phe Trp Phe Val Thr Gly Ser Gln
1               5                   10                  15

His Leu Tyr Gly Glu Glu Gln Leu Lys Ser Val Ala Lys Asp Ala Gln
            20                  25                  30

Asp Ile Ala Asp Lys Leu Asn Ala Ser Gly Lys Leu Pro Tyr Lys Val
        35                  40                  45

Val Phe Lys Asp Val Met Thr Thr Ala Glu Ser Ile Thr Asn Phe Met
    50                  55                  60

Lys Glu Val Asn Tyr Asn Asp Lys Val Ala Gly Val Ile Thr Trp Met
65                  70                  75                  80

His Thr Phe Ser Pro Ala Lys Asn Trp Ile Arg Gly Thr Glu Leu Leu
                85                  90                  95

Gln Lys Pro Leu Leu His Leu Ala Thr Gln Tyr Leu Asn Asn Ile Pro
            100                 105                 110

Tyr Ala Asp Ile Asp Phe Asp Tyr Met Asn Leu Asn Gln Ser Ala His
        115                 120                 125

Gly Asp Arg Glu Tyr Ala Tyr Ile Asn Ala Arg Leu Gln Lys His Asn
    130                 135                 140

Lys Ile Val Tyr Gly Tyr Trp Gly Asp Glu Asp Val Gln Glu Gln Ile
145                 150                 155                 160

Ala Arg Trp Glu Asp Val Ala Val Ala Tyr Asn Glu Ser Phe Lys Val
                165                 170                 175

Lys Val Ala Arg Phe Gly Asp Thr Met Arg Asn Val Ala Val Thr Glu
            180                 185                 190

Gly Asp Lys Val Glu Ala Gln Ile Lys Met Gly Trp Thr Val Asp Tyr
        195                 200                 205

Tyr Gly Ile Gly Asp Leu Val Glu Glu Ile Asn Lys Val Ser Asp Ala
    210                 215                 220

Asp Val Asp Lys Glu Tyr Ala Asp Leu Glu Ser Arg Tyr Glu Met Val
225                 230                 235                 240

Gln Gly Asp Asn Asp Ala Asp Thr Tyr Lys His Ser Val Arg Val Gln
                245                 250                 255

Leu Ala Gln Tyr Leu Gly Ile Lys Arg Phe Leu Glu Arg Gly Gly Tyr
```

```
              260                 265                 270
Thr Ala Phe Thr Thr Asn Phe Glu Asp Leu Trp Gly Met Glu Gln Leu
            275                 280                 285

Pro Gly Leu Ala Ser Gln Leu Leu Ile Arg Asp Gly Tyr Gly Phe Gly
            290                 295                 300

Ala Glu Gly Asp Trp Lys Thr Ala Ala Leu Gly Arg Val Met Lys Ile
305                 310                 315                 320

Met Ser His Asn Lys Gln Thr Ala Phe Met Glu Asp Tyr Thr Leu Asp
                325                 330                 335

Leu Arg His Gly His Glu Ala Ile Leu Gly Ser His Met Leu Glu Val
            340                 345                 350

Asp Pro Ser Ile Ala Ser Asp Lys Pro Arg Val Glu Val His Pro Leu
            355                 360                 365

Asp Ile Gly Gly Lys Asp Pro Ala Arg Leu Val Phe Thr Gly Ser
            370                 375                 380

Glu Gly Glu Ala Ile Asp Val Thr Val Ala Asp Phe Arg Asp Gly Phe
385                 390                 395                 400

Lys Met Ile Ser Tyr Ala Val Asp Ala Asn Lys Pro Glu Ala Glu Thr
                405                 410                 415

Pro Asn Leu Pro Val Ala Lys Gln Leu Trp Thr Pro Lys Met Gly Leu
            420                 425                 430

Lys Lys Gly Ala Leu Glu Trp Met Gln Ala Gly Gly His His Thr
            435                 440                 445

Met Leu Ser Phe Ser Leu Thr Glu Gln Met Glu Asp Tyr Ala Thr
450                 455                 460

Met Val Gly Met Thr Lys Ala Phe Leu Lys
465                 470

<210> SEQ ID NO 14
<211> LENGTH: 533
<212> TYPE: PRT
<213> ORGANISM: Lactobacillus plantarum
<220> FEATURE:
<221> NAME/KEY: MISC_FEATURE
<222> LOCATION: (1)..(533)
<223> OTHER INFORMATION: L-ribulokinase (araB)

<400> SEQUENCE: 14

Met Asn Leu Val Glu Thr Ala Gln Ala Ile Lys Thr Gly Lys Val Ser
1               5                   10                  15

Leu Gly Ile Glu Leu Gly Ser Thr Arg Ile Lys Ala Val Leu Ile Thr
            20                  25                  30

Asp Asp Phe Asn Thr Ile Ala Ser Gly Ser Tyr Val Trp Glu Asn Gln
        35                  40                  45

Phe Val Asp Gly Thr Trp Thr Tyr Ala Leu Glu Asp Val Trp Thr Gly
    50                  55                  60

Ile Gln Gln Ser Tyr Thr Gln Leu Ala Ala Asp Val Arg Ser Lys Tyr
65                  70                  75                  80

His Met Ser Leu Lys His Ile Asn Ala Ile Gly Ile Ser Ala Met Met
                85                  90                  95

His Gly Tyr Leu Ala Phe Asp Gln Gln Ala Lys Leu Leu Val Pro Phe
            100                 105                 110

Arg Thr Trp Arg Asn Asn Ile Thr Gly Gln Ala Ala Asp Glu Leu Thr
        115                 120                 125

Glu Leu Phe Asp Phe Asn Ile Pro Gln Arg Trp Ser Ile Ala His Leu
    130                 135                 140
```

```
Tyr Gln Ala Ile Leu Asn Asn Glu Ala His Val Lys Gln Val Asp Phe
145                 150                 155                 160

Ile Thr Thr Leu Ala Gly Tyr Val Thr Trp Lys Leu Ser Gly Glu Lys
                165                 170                 175

Val Leu Gly Ile Gly Asp Ala Ser Gly Val Phe Pro Ile Asp Glu Thr
            180                 185                 190

Thr Asp Thr Tyr Asn Gln Thr Met Leu Thr Lys Phe Ser Gln Leu Asp
                195                 200                 205

Lys Val Lys Pro Tyr Ser Trp Asp Ile Arg His Ile Leu Pro Arg Val
            210                 215                 220

Leu Pro Ala Gly Ala Ile Ala Gly Lys Leu Thr Ala Ala Gly Ala Ser
225                 230                 235                 240

Leu Leu Asp Gln Ser Gly Thr Leu Asp Ala Gly Ser Val Ile Ala Pro
                245                 250                 255

Pro Glu Gly Asp Ala Gly Thr Gly Met Val Gly Thr Asn Ser Val Arg
                260                 265                 270

Lys Arg Thr Gly Asn Ile Ser Val Gly Thr Ser Ala Phe Ser Met Asn
            275                 280                 285

Val Leu Asp Lys Pro Leu Ser Lys Val Tyr Arg Asp Ile Asp Ile Val
290                 295                 300

Met Thr Pro Asp Gly Ser Pro Val Ala Met Val His Val Asn Asn Cys
305                 310                 315                 320

Ser Ser Asp Ile Asn Ala Trp Ala Thr Ile Phe His Glu Phe Ala Ala
                325                 330                 335

Arg Leu Gly Met Glu Leu Lys Pro Asp Arg Leu Tyr Glu Thr Leu Phe
                340                 345                 350

Leu Glu Ser Thr Arg Ala Asp Ala Asp Ala Gly Gly Leu Ala Asn Tyr
            355                 360                 365

Ser Tyr Gln Ser Gly Glu Asn Ile Thr Lys Ile Gln Ala Gly Arg Pro
    370                 375                 380

Leu Phe Val Arg Thr Pro Asn Ser Lys Phe Ser Leu Pro Asn Phe Met
385                 390                 395                 400

Leu Thr Gln Leu Tyr Ala Ala Phe Ala Pro Leu Gln Leu Gly Met Asp
                405                 410                 415

Ile Leu Val Asn Glu Glu His Val Gln Thr Asp Val Met Ile Ala Gln
                420                 425                 430

Gly Gly Leu Phe Arg Thr Pro Val Ile Gly Gln Gln Val Leu Ala Asn
            435                 440                 445

Ala Leu Asn Ile Pro Ile Thr Val Met Ser Thr Ala Gly Glu Gly Gly
            450                 455                 460

Pro Trp Gly Met Ala Val Leu Ala Asn Phe Ala Cys Arg Gln Thr Ala
465                 470                 475                 480

Met Asn Leu Glu Asp Phe Leu Asp Gln Glu Val Phe Lys Glu Pro Glu
                485                 490                 495

Ser Met Thr Leu Ser Pro Glu Pro Glu Arg Val Ala Gly Tyr Arg Glu
                500                 505                 510

Phe Ile Gln Arg Tyr Gln Ala Gly Leu Pro Val Glu Ala Ala Ala Gly
                515                 520                 525

Gln Ala Ile Lys Tyr
            530

<210> SEQ ID NO 15
<211> LENGTH: 242
```

```
<212> TYPE: PRT
<213> ORGANISM: Lactobacillus plantarum
<220> FEATURE:
<221> NAME/KEY: MISC_FEATURE
<222> LOCATION: (1)..(242)
<223> OTHER INFORMATION: L-ribulose-5P-4-epimerase (araD)

<400> SEQUENCE: 15
```

Met Leu Glu Ala Leu Lys Gln Glu Val Tyr Glu Ala Asn Met Gln Leu
1               5                   10                  15

Pro Lys Leu Gly Leu Val Thr Phe Thr Trp Gly Asn Val Ser Gly Ile
            20                  25                  30

Asp Arg Glu Lys Gly Leu Phe Val Ile Lys Pro Ser Gly Val Asp Tyr
        35                  40                  45

Gly Glu Leu Lys Pro Ser Asp Leu Val Val Asn Leu Gln Gly Glu
    50                  55                  60

Val Val Glu Gly Lys Leu Asn Pro Ser Ser Asp Thr Pro Thr His Thr
65                  70                  75                  80

Val Leu Tyr Asn Ala Phe Pro Asn Ile Gly Gly Ile Val His Thr His
                85                  90                  95

Ser Pro Trp Ala Val Ala Tyr Ala Ala Ala Gln Met Asp Val Pro Ala
            100                 105                 110

Met Asn Thr Thr His Ala Asp Thr Phe Tyr Gly Asp Val Pro Ala Ala
        115                 120                 125

Asp Ala Leu Thr Lys Glu Glu Ile Glu Ala Asp Tyr Glu Gly Asn Thr
    130                 135                 140

Gly Lys Thr Ile Val Lys Thr Phe Gln Glu Arg Gly Leu Asp Tyr Glu
145                 150                 155                 160

Ala Val Pro Ala Ser Leu Val Ser Gln His Gly Pro Phe Ala Trp Gly
                165                 170                 175

Pro Thr Pro Ala Lys Ala Val Tyr Asn Ala Lys Val Leu Glu Val Val
            180                 185                 190

Ala Glu Glu Asp Tyr His Thr Ala Gln Leu Thr Arg Ala Ser Ser Glu
        195                 200                 205

Leu Pro Gln Tyr Leu Leu Asp Lys His Tyr Leu Arg Lys His Gly Ala
    210                 215                 220

Ser Ala Tyr Tyr Gly Gln Asn Asn Ala His Ser Lys Asp His Ala Val
225                 230                 235                 240

Arg Lys

```
<210> SEQ ID NO 16
<211> LENGTH: 17
<212> TYPE: DNA
<213> ORGANISM: Artificial Sequence
<220> FEATURE:
<223> OTHER INFORMATION: primer no. 5980

<400> SEQUENCE: 16
cgaccgagtt gctcttg                                                   17

<210> SEQ ID NO 17
<211> LENGTH: 33
<212> TYPE: DNA
<213> ORGANISM: Artificial Sequence
<220> FEATURE:
<223> OTHER INFORMATION: primer no. 5792

<400> SEQUENCE: 17
gttttagagc tagaaatagc aagttaaaat aag                                 33
```

<210> SEQ ID NO 18
<211> LENGTH: 20
<212> TYPE: DNA
<213> ORGANISM: Artificial Sequence
<220> FEATURE:
<223> OTHER INFORMATION: primer no. 5979

<400> SEQUENCE: 18
tattgacgcc gggcaagagc                                                 20

<210> SEQ ID NO 19
<211> LENGTH: 72
<212> TYPE: DNA
<213> ORGANISM: Artificial Sequence
<220> FEATURE:
<223> OTHER INFORMATION: primer no. 5978

<400> SEQUENCE: 19
attttaactt gctatttcta gctctaaaac tttatgacgt atacgtttac gatcatttat     60
ctttcactgc gg                                                         72

<210> SEQ ID NO 20
<211> LENGTH: 20
<212> TYPE: DNA
<213> ORGANISM: Artificial Sequence
<220> FEATURE:
<223> OTHER INFORMATION: primer no. 5941

<400> SEQUENCE: 20
gctggccttt tgctcacatg                                                 20

<210> SEQ ID NO 21
<211> LENGTH: 27
<212> TYPE: DNA
<213> ORGANISM: Artificial Sequence
<220> FEATURE:
<223> OTHER INFORMATION: primer no. 6005

<400> SEQUENCE: 21
gatcatttat ctttcactgc ggagaag                                         27

<210> SEQ ID NO 22
<211> LENGTH: 103
<212> TYPE: DNA
<213> ORGANISM: Artificial Sequence
<220> FEATURE:
<223> OTHER INFORMATION: primer no. 9269

<400> SEQUENCE: 22
tgcgcatgtt tcggcgttcg aaacttctcc gcagtgaaag ataaatgatc attgacacca    60
aaaacatgtt gttttagagc tagaaatagc aagttaaaat aag                      103

<210> SEQ ID NO 23
<211> LENGTH: 120
<212> TYPE: DNA
<213> ORGANISM: Artificial Sequence
<220> FEATURE:
<223> OTHER INFORMATION: primer no. 9401

<400> SEQUENCE: 23
tgcgcatgtt tcggcgttcg aaacttctcc gcagtgaaag ataaatgatc ttttgttcca    60
aacattactc gttttagagc tagaaatagc aagttaaaat aaggctagtc cgttatcaac   120

<210> SEQ ID NO 24
<211> LENGTH: 120
<212> TYPE: DNA
<213> ORGANISM: Artificial Sequence
<220> FEATURE:
<223> OTHER INFORMATION: primer no. 11270

<400> SEQUENCE: 24
gttgataacg gactagcctt attttaactt gctatttcta gctctaaaac agtaacgtac    60
actttattac gatcatttat ctttcactgc ggagaagttt cgaacgccga aacatgcgca   120

<210> SEQ ID NO 25
<211> LENGTH: 120
<212> TYPE: DNA
<213> ORGANISM: Artificial Sequence
<220> FEATURE:
<223> OTHER INFORMATION: primer no. 11373

<400> SEQUENCE: 25
gttgataacg gactagcctt attttaactt gctatttcta gctctaaaac cttatataat    60
gactctgcag gatcatttat ctttcactgc ggagaagttt cgaacgccga aacatgcgca   120

<210> SEQ ID NO 26
<211> LENGTH: 80
<212> TYPE: DNA
<213> ORGANISM: Artificial Sequence
<220> FEATURE:
<223> OTHER INFORMATION: primer no. 8956

<400> SEQUENCE: 26
gccagaggta tagacatagc cagacctacc taattggtgc atcaggtggt catggccctt    60
gacgcgcata accgctagag                                                80

<210> SEQ ID NO 27
<211> LENGTH: 20
<212> TYPE: DNA
<213> ORGANISM: Artificial Sequence
<220> FEATURE:
<223> OTHER INFORMATION: primer no. 8960

<400> SEQUENCE: 27
tgtatatgag atagttgatt                                                20

<210> SEQ ID NO 28
<211> LENGTH: 80
<212> TYPE: DNA
<213> ORGANISM: Artificial Sequence
<220> FEATURE:
<223> OTHER INFORMATION: primer no. 8958

<400> SEQUENCE: 28
tgagctacac tgtccgcaag attgcgacct cgtcatggct atacggtctc gcagatcgct    60
ccactagtca gatgccgcgg                                                80

<210> SEQ ID NO 29
<211> LENGTH: 20
<212> TYPE: DNA
<213> ORGANISM: Artificial Sequence
<220> FEATURE:
<223> OTHER INFORMATION: primer no. 8961

<400> SEQUENCE: 29
tttgatttag tgtttgtgtg                                                20

<210> SEQ ID NO 30
<211> LENGTH: 50
<212> TYPE: DNA
<213> ORGANISM: Artificial Sequence
<220> FEATURE:
<223> OTHER INFORMATION: primer no. 8953

<400> SEQUENCE: 30
ccaagcatac aatcaactat ctcatataca atgagtgaag gccccgtcaa          50

<210> SEQ ID NO 31
<211> LENGTH: 80
<212> TYPE: DNA
<213> ORGANISM: Artificial Sequence
<220> FEATURE:
<223> OTHER INFORMATION: primer no. 8964

<400> SEQUENCE: 31
agcgatctgc gagaccgtat agccatgacg aggtcgcaat cttgcggaca gtgtagctca          60
gggcaaaggg acagatgaag          80

<210> SEQ ID NO 32
<211> LENGTH: 50
<212> TYPE: DNA
<213> ORGANISM: Artificial Sequence
<220> FEATURE:
<223> OTHER INFORMATION: primer no. 8984

<400> SEQUENCE: 32
tgcttatcaa cacacaaaca ctaaatcaaa atggtgacag tcggtgtgtt          50

<210> SEQ ID NO 33
<211> LENGTH: 80
<212> TYPE: DNA
<213> ORGANISM: Artificial Sequence
<220> FEATURE:
<223> OTHER INFORMATION: primer no. 8986

<400> SEQUENCE: 33
gtcacgggtt ctcagcaatt cgagctatta ccgatgatgg ctgaggcgtt agagtaatct          60
cgggctagag atcttgactg          80

<210> SEQ ID NO 34
<211> LENGTH: 21
<212> TYPE: DNA
<213> ORGANISM: Artificial Sequence
<220> FEATURE:
<223> OTHER INFORMATION: primer no. 4870

<400> SEQUENCE: 34
gccagaggta tagacatagc c          21

<210> SEQ ID NO 35
<211> LENGTH: 22
<212> TYPE: DNA
<213> ORGANISM: Artificial Sequence
<220> FEATURE:
<223> OTHER INFORMATION: primer no. 7369

<400> SEQUENCE: 35
agcgatctgc gagaccgtat ag          22

<210> SEQ ID NO 36

-continued

<210> SEQ ID NO 36
<211> LENGTH: 22
<212> TYPE: DNA
<213> ORGANISM: Artificial Sequence
<220> FEATURE:
<223> OTHER INFORMATION: primer no. 3290

<400> SEQUENCE: 36
gtcacgggtt ctcagcaatt cg                                              22

<210> SEQ ID NO 37
<211> LENGTH: 23
<212> TYPE: DNA
<213> ORGANISM: Artificial Sequence
<220> FEATURE:
<223> OTHER INFORMATION: primer no. 3291

<400> SEQUENCE: 37
ctctaacgcc tcagccatca tcg                                             23

<210> SEQ ID NO 38
<211> LENGTH: 22
<212> TYPE: DNA
<213> ORGANISM: Artificial Sequence
<220> FEATURE:
<223> OTHER INFORMATION: primer no. 4068

<400> SEQUENCE: 38
gcctacggtt cccgaagtat gc                                              22

<210> SEQ ID NO 39
<211> LENGTH: 26
<212> TYPE: DNA
<213> ORGANISM: Artificial Sequence
<220> FEATURE:
<223> OTHER INFORMATION: primer no. 3274

<400> SEQUENCE: 39
tattcacgta gacggatagg tatagc                                          26

<210> SEQ ID NO 40
<211> LENGTH: 26
<212> TYPE: DNA
<213> ORGANISM: Artificial Sequence
<220> FEATURE:
<223> OTHER INFORMATION: primer no. 3275

<400> SEQUENCE: 40
gtgcctattg atgatctggc ggaatg                                          26

<210> SEQ ID NO 41
<211> LENGTH: 25
<212> TYPE: DNA
<213> ORGANISM: Artificial Sequence
<220> FEATURE:
<223> OTHER INFORMATION: primer no. 3847

<400> SEQUENCE: 41
actatatgtg aaggcatggc tatgg                                           25

<210> SEQ ID NO 42
<211> LENGTH: 27
<212> TYPE: DNA
<213> ORGANISM: Artificial Sequence
<220> FEATURE:
<223> OTHER INFORMATION: primer no. 3276

<400> SEQUENCE: 42

```
gttgaacatt cttaggctgg tcgaatc                                              27
```

<210> SEQ ID NO 43
<211> LENGTH: 20
<212> TYPE: DNA
<213> ORGANISM: Artificial Sequence
<220> FEATURE:
<223> OTHER INFORMATION: primer no. 4691

<400> SEQUENCE: 43

```
cacctttcga gaggacgatg                                                     20
```

<210> SEQ ID NO 44
<211> LENGTH: 30
<212> TYPE: DNA
<213> ORGANISM: Artificial Sequence
<220> FEATURE:
<223> OTHER INFORMATION: primer no. 3277

<400> SEQUENCE: 44

```
ctagcgtgtc ctcgcatagt tcttagattg                                          30
```

<210> SEQ ID NO 45
<211> LENGTH: 22
<212> TYPE: DNA
<213> ORGANISM: Artificial Sequence
<220> FEATURE:
<223> OTHER INFORMATION: primer no. 3283

<400> SEQUENCE: 45

```
acgtctcacg gatcgtatat gc                                                  22
```

<210> SEQ ID NO 46
<211> LENGTH: 24
<212> TYPE: DNA
<213> ORGANISM: Artificial Sequence
<220> FEATURE:
<223> OTHER INFORMATION: primer no. 3288

<400> SEQUENCE: 46

```
tgccgaactt tccctgtatg aagc                                                24
```

<210> SEQ ID NO 47
<211> LENGTH: 80
<212> TYPE: DNA
<213> ORGANISM: Artificial Sequence
<220> FEATURE:
<223> OTHER INFORMATION: primer no. 7133

<400> SEQUENCE: 47

```
tataatattt cattatcgga actctagatt ctatacttgt ttcccaattg ttgctggtag         60
ggcccttccg ggagtttatc                                                     80
```

<210> SEQ ID NO 48
<211> LENGTH: 80
<212> TYPE: DNA
<213> ORGANISM: Artificial Sequence
<220> FEATURE:
<223> OTHER INFORMATION: primer no. 10460

<400> SEQUENCE: 48

```
actatatgtg aaggcatggc tatggcacgg cagacattcc gccagatcat caataggcac         60
cggccgtgtt taaagattac                                                     80
```

<210> SEQ ID NO 49
<211> LENGTH: 90
<212> TYPE: DNA
<213> ORGANISM: Artificial Sequence
<220> FEATURE:
<223> OTHER INFORMATION: primer no. 10461

<400> SEQUENCE: 49
gccgtagctt ccgcaagtat gccgtagttg aagagcattt gccgtcggtt caggtcatat    60
tcataggtga gaaagagatg gagaatgtag    90

<210> SEQ ID NO 50
<211> LENGTH: 79
<212> TYPE: DNA
<213> ORGANISM: Artificial Sequence
<220> FEATURE:
<223> OTHER INFORMATION: primer no. 6285

<400> SEQUENCE: 50
aagggccatg accacctgat gcaccaatta ggtaggtctg gctatgtcta tacctctggc    60
gcgataccct gcgatcttc    79

<210> SEQ ID NO 51
<211> LENGTH: 88
<212> TYPE: DNA
<213> ORGANISM: Artificial Sequence
<220> FEATURE:
<223> OTHER INFORMATION: primer no. 7548

<400> SEQUENCE: 51
gcatagaaca ttatccgcgg aaacgggtat taggggtgag ggtgaataag gaaagtcagg    60
gaaatcgggc cgcgcagatt agcgaagc    88

<210> SEQ ID NO 52
<211> LENGTH: 79
<212> TYPE: DNA
<213> ORGANISM: Artificial Sequence
<220> FEATURE:
<223> OTHER INFORMATION: primer no. 6280

<400> SEQUENCE: 52
gtgcctattg atgatctggc ggaatgtctg ccgtgccata gccatgcctt cacatatagt    60
gcgataccct gcgatcttc    79

<210> SEQ ID NO 53
<211> LENGTH: 78
<212> TYPE: DNA
<213> ORGANISM: Artificial Sequence
<220> FEATURE:
<223> OTHER INFORMATION: primer no. 6273

<400> SEQUENCE: 53
gccagaggta tagacatagc cagacctacc taattggtgc atcaggtggt catggccctt    60
cgcgcagatt agcgaagc    78

<210> SEQ ID NO 54
<211> LENGTH: 79
<212> TYPE: DNA
<213> ORGANISM: Artificial Sequence
<220> FEATURE:
<223> OTHER INFORMATION: primer no. 6281

<400> SEQUENCE: 54

```
gttgaacatt cttaggctgg tcgaatcatt tagacacggg catcgtcctc tcgaaaggtg    60
gcgataccct gcgatcttc                                                 79
```

<210> SEQ ID NO 55
<211> LENGTH: 78
<212> TYPE: DNA
<213> ORGANISM: Artificial Sequence
<220> FEATURE:
<223> OTHER INFORMATION: primer no. 6270

<400> SEQUENCE: 55

```
actatatgtg aaggcatggc tatggcacgg cagacattcc gccagatcat caataggcac    60
cgcgcagatt agcgaagc                                                  78
```

<210> SEQ ID NO 56
<211> LENGTH: 79
<212> TYPE: DNA
<213> ORGANISM: Artificial Sequence
<220> FEATURE:
<223> OTHER INFORMATION: primer no. 6282

<400> SEQUENCE: 56

```
ctagcgtgtc ctcgcatagt tcttagattg tcgctacggc atatacgatc cgtgagacgt    60
gcgataccct gcgatcttc                                                 79
```

<210> SEQ ID NO 57
<211> LENGTH: 78
<212> TYPE: DNA
<213> ORGANISM: Artificial Sequence
<220> FEATURE:
<223> OTHER INFORMATION: primer no. 6271

<400> SEQUENCE: 57

```
cacctttcga gaggacgatg cccgtgtcta aatgattcga ccagcctaag aatgttcaac    60
cgcgcagatt agcgaagc                                                  78
```

<210> SEQ ID NO 58
<211> LENGTH: 79
<212> TYPE: DNA
<213> ORGANISM: Artificial Sequence
<220> FEATURE:
<223> OTHER INFORMATION: primer no. 6284

<400> SEQUENCE: 58

```
aatcactctc catacagggt ttcatacatt tctccacggg acccacagtc gtagatgcgt    60
gcgataccct gcgatcttc                                                 79
```

<210> SEQ ID NO 59
<211> LENGTH: 78
<212> TYPE: DNA
<213> ORGANISM: Artificial Sequence
<220> FEATURE:
<223> OTHER INFORMATION: primer no. 6272

<400> SEQUENCE: 59

```
acgtctcacg gatcgtatat gccgtagcga caatctaaga actatgcgag gacacgctag    60
cgcgcagatt agcgaagc                                                  78
```

<210> SEQ ID NO 60
<211> LENGTH: 79
<212> TYPE: DNA

<213> ORGANISM: Artificial Sequence
<220> FEATURE:
<223> OTHER INFORMATION: primer no. 6283

<400> SEQUENCE: 60
acgcatctac gactgtgggt cccgtggaga aatgtatgaa accctgtatg gagagtgatt    60
gcgataccct gcgatcttc    79

<210> SEQ ID NO 61
<211> LENGTH: 78
<212> TYPE: DNA
<213> ORGANISM: Artificial Sequence
<220> FEATURE:
<223> OTHER INFORMATION: primer no. 6275

<400> SEQUENCE: 61
acgagagatg aaggctcacc gatggactta gtatgatgcc atgctggaag ctccggtcat    60
cgcgcagatt agcgaagc    78

<210> SEQ ID NO 62
<211> LENGTH: 79
<212> TYPE: DNA
<213> ORGANISM: Artificial Sequence
<220> FEATURE:
<223> OTHER INFORMATION: primer no. 6287

<400> SEQUENCE: 62
atgaccggag cttccagcat ggcatcatac taagtccatc ggtgagcctt catctctcgt    60
gcgataccct gcgatcttc    79

<210> SEQ ID NO 63
<211> LENGTH: 78
<212> TYPE: DNA
<213> ORGANISM: Artificial Sequence
<220> FEATURE:
<223> OTHER INFORMATION: primer no. 6276

<400> SEQUENCE: 63
ttctaggctt tgatgcaagg tccacatatc ttcgttagga ctcaatcgtg gctgctgatc    60
cgcgcagatt agcgaagc    78

<210> SEQ ID NO 64
<211> LENGTH: 79
<212> TYPE: DNA
<213> ORGANISM: Artificial Sequence
<220> FEATURE:
<223> OTHER INFORMATION: primer no. 6288

<400> SEQUENCE: 64
gatcagcagc cacgattgag tcctaacgaa gatatgtgga ccttgcatca aagcctagaa    60
gcgataccct gcgatcttc    79

<210> SEQ ID NO 65
<211> LENGTH: 78
<212> TYPE: DNA
<213> ORGANISM: Artificial Sequence
<220> FEATURE:
<223> OTHER INFORMATION: primer no. 6277

<400> SEQUENCE: 65
atactccctg cacagatgag tcaagctatt gaacaccgag aacgcgctga acgatcattc    60
cgcgcagatt agcgaagc    78

<210> SEQ ID NO 66
<211> LENGTH: 79
<212> TYPE: DNA
<213> ORGANISM: Artificial Sequence
<220> FEATURE:
<223> OTHER INFORMATION: primer no. 6289

<400> SEQUENCE: 66
gaatgatcgt tcagcgcgtt ctcggtgttc aatagcttga ctcatctgtg cagggagtat    60
gcgataccct gcgatcttc                                                 79

<210> SEQ ID NO 67
<211> LENGTH: 78
<212> TYPE: DNA
<213> ORGANISM: Artificial Sequence
<220> FEATURE:
<223> OTHER INFORMATION: primer no. 6274

<400> SEQUENCE: 67
gcctacggtt cccgaagtat gctgctgatg tctggctata cctatccgtc tacgtgaata    60
cgcgcagatt agcgaagc                                                  78

<210> SEQ ID NO 68
<211> LENGTH: 89
<212> TYPE: DNA
<213> ORGANISM: Artificial Sequence
<220> FEATURE:
<223> OTHER INFORMATION: primer no. 5920

<400> SEQUENCE: 68
tattcacgta gacggatagg tatagccaga catcagcagc atacttcggg aaccgtaggc    60
agctcatagc ttcaaaatgt ttctactcc                                      89

<210> SEQ ID NO 69
<211> LENGTH: 78
<212> TYPE: DNA
<213> ORGANISM: Artificial Sequence
<220> FEATURE:
<223> OTHER INFORMATION: primer no. 9029

<400> SEQUENCE: 69
tatatttgat gtaaatatct aggaaataca cttgtgtata cttctcgctt ttctttttatt   60 gtccagtgct tccacatc                                                  78

<210> SEQ ID NO 70
<211> LENGTH: 85
<212> TYPE: DNA
<213> ORGANISM: Artificial Sequence
<220> FEATURE:
<223> OTHER INFORMATION: primer no. 7135

<400> SEQUENCE: 70
atatgacctg aaccgacggc aaatgctctt caactacggc atacttgcgg aagctacggc    60
catagcttca aaatgtttct actcc                                          85

<210> SEQ ID NO 71
<211> LENGTH: 78
<212> TYPE: DNA
<213> ORGANISM: Artificial Sequence
<220> FEATURE:
<223> OTHER INFORMATION: primer no. 7222

<400> SEQUENCE: 71
cagacagcaa actttgttcc atggtcgcca ttgactatgg tgcaatcgct gacatgagcc    60
gtccagtgct tccacatc    78

<210> SEQ ID NO 72
<211> LENGTH: 20
<212> TYPE: DNA
<213> ORGANISM: Artificial Sequence
<220> FEATURE:
<223> OTHER INFORMATION: primer no. 11273

<400> SEQUENCE: 72
ccgttaaaac acaggccacg    20

<210> SEQ ID NO 73
<211> LENGTH: 20
<212> TYPE: DNA
<213> ORGANISM: Artificial Sequence
<220> FEATURE:
<223> OTHER INFORMATION: primer no. 11274

<400> SEQUENCE: 73
tgccgtgtga acgttcaaag    20

<210> SEQ ID NO 74
<211> LENGTH: 26
<212> TYPE: DNA
<213> ORGANISM: Artificial Sequence
<220> FEATURE:
<223> OTHER INFORMATION: primer no. 3275

<400> SEQUENCE: 74
gtgcctattg atgatctggc ggaatg    26

<210> SEQ ID NO 75
<211> LENGTH: 27
<212> TYPE: DNA
<213> ORGANISM: Artificial Sequence
<220> FEATURE:
<223> OTHER INFORMATION: primer no. 3276

<400> SEQUENCE: 75
gttgaacatt cttaggctgg tcgaatc    27

<210> SEQ ID NO 76
<211> LENGTH: 20
<212> TYPE: DNA
<213> ORGANISM: Artificial Sequence
<220> FEATURE:
<223> OTHER INFORMATION: primer no. 5971

<400> SEQUENCE: 76
agagccggca tgcaaggaac    20

<210> SEQ ID NO 77
<211> LENGTH: 20
<212> TYPE: DNA
<213> ORGANISM: Artificial Sequence
<220> FEATURE:
<223> OTHER INFORMATION: primer no. 6637

<400> SEQUENCE: 77
ggctgctgtt aaggatgatg    20

```
<210> SEQ ID NO 78
<211> LENGTH: 20
<212> TYPE: DNA
<213> ORGANISM: Artificial Sequence
<220> FEATURE:
<223> OTHER INFORMATION: primer no. 6640

<400> SEQUENCE: 78
ctagatgtgg tcagccattc                                            20

<210> SEQ ID NO 79
<211> LENGTH: 20
<212> TYPE: DNA
<213> ORGANISM: Artificial Sequence
<220> FEATURE:
<223> OTHER INFORMATION: primer no. 7869

<400> SEQUENCE: 79
ctttgggcaa tcctttggag                                            20

<210> SEQ ID NO 80
<211> LENGTH: 20
<212> TYPE: DNA
<213> ORGANISM: Artificial Sequence
<220> FEATURE:
<223> OTHER INFORMATION: primer no. 7870

<400> SEQUENCE: 80
cttcatcagc accgtcaaac                                            20

<210> SEQ ID NO 81
<211> LENGTH: 20
<212> TYPE: DNA
<213> ORGANISM: Artificial Sequence
<220> FEATURE:
<223> OTHER INFORMATION: primer no. 7871

<400> SEQUENCE: 81
ggtgatttcg gctctattgc                                            20

<210> SEQ ID NO 82
<211> LENGTH: 20
<212> TYPE: DNA
<213> ORGANISM: Artificial Sequence
<220> FEATURE:
<223> OTHER INFORMATION: primer no. 7872

<400> SEQUENCE: 82
tcggcttcac ccttgtaatc                                            20

<210> SEQ ID NO 83
<211> LENGTH: 20
<212> TYPE: DNA
<213> ORGANISM: Artificial Sequence
<220> FEATURE:
<223> OTHER INFORMATION: primer no. 7873

<400> SEQUENCE: 83
acccatgtgg ttgctgattc                                            20

<210> SEQ ID NO 84
<211> LENGTH: 20
<212> TYPE: DNA
<213> ORGANISM: Artificial Sequence
<220> FEATURE:
<223> OTHER INFORMATION: primer no. 7874
```

```
<400> SEQUENCE: 84
aaatctgggt gccgaattcc                                              20

<210> SEQ ID NO 85
<211> LENGTH: 20
<212> TYPE: DNA
<213> ORGANISM: Artificial Sequence
<220> FEATURE:
<223> OTHER INFORMATION: primer no. 7875

<400> SEQUENCE: 85
ttgataagct agccgtctcc                                              20

<210> SEQ ID NO 86
<211> LENGTH: 20
<212> TYPE: DNA
<213> ORGANISM: Artificial Sequence
<220> FEATURE:
<223> OTHER INFORMATION: primer no. 7877

<400> SEQUENCE: 86
caaccatatg cctcgtatcg                                              20

<210> SEQ ID NO 87
<211> LENGTH: 20
<212> TYPE: DNA
<213> ORGANISM: Artificial Sequence
<220> FEATURE:
<223> OTHER INFORMATION: primer no. 7923

<400> SEQUENCE: 87
gaagcagcgt attgcaaagc                                              20

<210> SEQ ID NO 88
<211> LENGTH: 20
<212> TYPE: DNA
<213> ORGANISM: Artificial Sequence
<220> FEATURE:
<223> OTHER INFORMATION: primer no. 8969

<400> SEQUENCE: 88
tcagagacgt gatgcagaac                                              20

<210> SEQ ID NO 89
<211> LENGTH: 20
<212> TYPE: DNA
<213> ORGANISM: Artificial Sequence
<220> FEATURE:
<223> OTHER INFORMATION: primer no. 8987

<400> SEQUENCE: 89
atcgtggcac caagcaactc                                              20

<210> SEQ ID NO 90
<211> LENGTH: 20
<212> TYPE: DNA
<213> ORGANISM: Artificial Sequence
<220> FEATURE:
<223> OTHER INFORMATION: primer no. 8988

<400> SEQUENCE: 90
ttgggctgtg gtcctgatgg                                              20

<210> SEQ ID NO 91
<211> LENGTH: 21
```

```
<212> TYPE: DNA
<213> ORGANISM: Artificial Sequence
<220> FEATURE:
<223> OTHER INFORMATION: primer no. 533

<400> SEQUENCE: 91
catggcatgt aatggaaagc a                                              21

<210> SEQ ID NO 92
<211> LENGTH: 21
<212> TYPE: DNA
<213> ORGANISM: Artificial Sequence
<220> FEATURE:
<223> OTHER INFORMATION: primer no. 3354

<400> SEQUENCE: 92
acgcatctac gactgtgggt c                                              21

<210> SEQ ID NO 93
<211> LENGTH: 18
<212> TYPE: DNA
<213> ORGANISM: Artificial Sequence
<220> FEATURE:
<223> OTHER INFORMATION: primer no. 3837

<400> SEQUENCE: 93
gaatgatcgt tcagcgcg                                                  18

<210> SEQ ID NO 94
<211> LENGTH: 18
<212> TYPE: DNA
<213> ORGANISM: Artificial Sequence
<220> FEATURE:
<223> OTHER INFORMATION: primer no. 3843

<400> SEQUENCE: 94
gatcagcagc cacgattg                                                  18

<210> SEQ ID NO 95
<211> LENGTH: 20
<212> TYPE: DNA
<213> ORGANISM: Artificial Sequence
<220> FEATURE:
<223> OTHER INFORMATION: primer no. 4173

<400> SEQUENCE: 95
gttgaacatt cttaggctgg                                                20

<210> SEQ ID NO 96
<211> LENGTH: 21
<212> TYPE: DNA
<213> ORGANISM: Artificial Sequence
<220> FEATURE:
<223> OTHER INFORMATION: primer no. 4184

<400> SEQUENCE: 96
atgaccggag cttccagcat g                                              21

<210> SEQ ID NO 97
<211> LENGTH: 18
<212> TYPE: DNA
<213> ORGANISM: Artificial Sequence
<220> FEATURE:
<223> OTHER INFORMATION: primer no. 4692

<400> SEQUENCE: 97
```
aagggccatg accacctg                                        18

<210> SEQ ID NO 98
<211> LENGTH: 19
<212> TYPE: DNA
<213> ORGANISM: Artificial Sequence
<220> FEATURE:
<223> OTHER INFORMATION: primer no. 5231

<400> SEQUENCE: 98
aatcactctc catacaggg                                       19

<210> SEQ ID NO 99
<211> LENGTH: 21
<212> TYPE: DNA
<213> ORGANISM: Artificial Sequence
<220> FEATURE:
<223> OTHER INFORMATION: primer no. 6632

<400> SEQUENCE: 99
agcgtcgtag tagtggaaag c                                    21

<210> SEQ ID NO 100
<211> LENGTH: 25
<212> TYPE: DNA
<213> ORGANISM: Artificial Sequence
<220> FEATURE:
<223> OTHER INFORMATION: primer no. 6633

<400> SEQUENCE: 100
atggacgcta tggctagagc tttgg                                25

<210> SEQ ID NO 101
<211> LENGTH: 20
<212> TYPE: DNA
<213> ORGANISM: Artificial Sequence
<220> FEATURE:
<223> OTHER INFORMATION: primer no. 7056

<400> SEQUENCE: 101
agaggtggtg gtttcgttac                                      20

<210> SEQ ID NO 102
<211> LENGTH: 20
<212> TYPE: DNA
<213> ORGANISM: Artificial Sequence
<220> FEATURE:
<223> OTHER INFORMATION: primer no. 7298

<400> SEQUENCE: 102
ttgttcaatg gatgcggttc                                      20

<210> SEQ ID NO 103
<211> LENGTH: 20
<212> TYPE: DNA
<213> ORGANISM: Artificial Sequence
<220> FEATURE:
<223> OTHER INFORMATION: primer no. 7479

<400> SEQUENCE: 103
ggacgttccg acatagtatc                                      20

<210> SEQ ID NO 104
<211> LENGTH: 21
<212> TYPE: DNA
<213> ORGANISM: Artificial Sequence

```
<220> FEATURE:
<223> OTHER INFORMATION: primer no. 9010

<400> SEQUENCE: 104
cctctcccTt gccaaagaac c                                          21

<210> SEQ ID NO 105
<211> LENGTH: 20
<212> TYPE: DNA
<213> ORGANISM: Artificial Sequence
<220> FEATURE:
<223> OTHER INFORMATION: primer no. 1814

<400> SEQUENCE: 105
caaactggcc actgaattgc                                            20

<210> SEQ ID NO 106
<211> LENGTH: 20
<212> TYPE: DNA
<213> ORGANISM: Artificial Sequence
<220> FEATURE:
<223> OTHER INFORMATION: primer no. 1815

<400> SEQUENCE: 106
tccaattcct tgccgatgac                                            20

<210> SEQ ID NO 107
<211> LENGTH: 24
<212> TYPE: DNA
<213> ORGANISM: Artificial Sequence
<220> FEATURE:
<223> OTHER INFORMATION: primer no. 5004

<400> SEQUENCE: 107
gtagattgca ccatctgaag aggc                                       24

<210> SEQ ID NO 108
<211> LENGTH: 21
<212> TYPE: DNA
<213> ORGANISM: Artificial Sequence
<220> FEATURE:
<223> OTHER INFORMATION: primer no. 5007

<400> SEQUENCE: 108
gaggatgcta aaagtcccgt c                                          21

<210> SEQ ID NO 109
<211> LENGTH: 20
<212> TYPE: DNA
<213> ORGANISM: Artificial Sequence
<220> FEATURE:
<223> OTHER INFORMATION: primer no. 7868

<400> SEQUENCE: 109
caacttgggt tgcgaatgtc                                            20

<210> SEQ ID NO 110
<211> LENGTH: 20
<212> TYPE: DNA
<213> ORGANISM: Artificial Sequence
<220> FEATURE:
<223> OTHER INFORMATION: primer no. 7922

<400> SEQUENCE: 110
cgcaattcct tcgagacttc                                            20
```

<210> SEQ ID NO 111
<211> LENGTH: 20
<212> TYPE: DNA
<213> ORGANISM: Artificial Sequence
<220> FEATURE:
<223> OTHER INFORMATION: primer no. 9271

<400> SEQUENCE: 111
atgaggcaag aaccgggatg                                               20

<210> SEQ ID NO 112
<211> LENGTH: 20
<212> TYPE: DNA
<213> ORGANISM: Artificial Sequence
<220> FEATURE:
<223> OTHER INFORMATION: primer no. 9272

<400> SEQUENCE: 112
ccttcgcgca ctgattcatc                                               20

<210> SEQ ID NO 113
<211> LENGTH: 20
<212> TYPE: DNA
<213> ORGANISM: Artificial Sequence
<220> FEATURE:
<223> OTHER INFORMATION: primer no. 9275

<400> SEQUENCE: 113
agttgcactc tgatgggctc                                               20

<210> SEQ ID NO 114
<211> LENGTH: 20
<212> TYPE: DNA
<213> ORGANISM: Artificial Sequence
<220> FEATURE:
<223> OTHER INFORMATION: primer no. 9276

<400> SEQUENCE: 114
gacgatactg catcccaggg                                               20

<210> SEQ ID NO 115
<211> LENGTH: 22
<212> TYPE: DNA
<213> ORGANISM: Artificial Sequence
<220> FEATURE:
<223> OTHER INFORMATION: primer no. 4930

<400> SEQUENCE: 115
ggcaagagta tagcgtgata cc                                            22

<210> SEQ ID NO 116
<211> LENGTH: 22
<212> TYPE: DNA
<213> ORGANISM: Artificial Sequence
<220> FEATURE:
<223> OTHER INFORMATION: primer no. 4931

<400> SEQUENCE: 116
cgcaagctat ctagaggaag tg                                            22

<210> SEQ ID NO 117
<211> LENGTH: 20
<212> TYPE: DNA
<213> ORGANISM: Artificial Sequence
<220> FEATURE:
<223> OTHER INFORMATION: primer no. 11273

```
<400> SEQUENCE: 117
ccgttaaaac acaggccacg                                                20

<210> SEQ ID NO 118
<211> LENGTH: 20
<212> TYPE: DNA
<213> ORGANISM: Artificial Sequence
<220> FEATURE:
<223> OTHER INFORMATION: primer no. 11274

<400> SEQUENCE: 118
tgccgtgtga acgttcaaag                                                20

<210> SEQ ID NO 119
<211> LENGTH: 20
<212> TYPE: DNA
<213> ORGANISM: Artificial Sequence
<220> FEATURE:
<223> OTHER INFORMATION: primer no. 11376

<400> SEQUENCE: 119
agcacccacc cagctatgtc                                                20

<210> SEQ ID NO 120
<211> LENGTH: 20
<212> TYPE: DNA
<213> ORGANISM: Artificial Sequence
<220> FEATURE:
<223> OTHER INFORMATION: primer no. 11377

<400> SEQUENCE: 120
gtacgctcgt ttcaggtatg                                                20

<210> SEQ ID NO 121
<211> LENGTH: 120
<212> TYPE: DNA
<213> ORGANISM: Artificial Sequence
<220> FEATURE:
<223> OTHER INFORMATION: primer no. 9279

<400> SEQUENCE: 121
tttaatacat attcctctag tcttgcaaaa tcgatttaga atcaagatac cagcctaaaa    60
acaaatcgct cttaaatata tacctaaaga acattaaagc tatattataa gcaaagatac   120

<210> SEQ ID NO 122
<211> LENGTH: 120
<212> TYPE: DNA
<213> ORGANISM: Artificial Sequence
<220> FEATURE:
<223> OTHER INFORMATION: primer no. 9280

<400> SEQUENCE: 122
gtatctttgc ttataatata gctttaatgt tctttaggta tatatttaag agcgatttgt    60
ttttaggctg gtatcttgat tctaaatcga ttttgcaaga ctagaggaat atgtattaaa   120

<210> SEQ ID NO 123
<211> LENGTH: 120
<212> TYPE: DNA
<213> ORGANISM: Artificial Sequence
<220> FEATURE:
<223> OTHER INFORMATION: primer no. 9281

<400> SEQUENCE: 123
```

```
caatttcatg caagaaggcc atttgctaat tccaagagcg aggtaaacac acaagaaaaa    60
ttgtacatat gcggcatttc ttatatttat actctctata ctatacgata tggtattttt   120
```

<210> SEQ ID NO 124
<211> LENGTH: 120
<212> TYPE: DNA
<213> ORGANISM: Artificial Sequence
<220> FEATURE:
<223> OTHER INFORMATION: primer no. 9282

<400> SEQUENCE: 124

```
aaaaatacca tatcgtatag tatagagagt ataaatataa gaaatgccgc atatgtacaa    60
tttttcttgt gtgtttacct cgctcttgga attagcaaat ggccttcttg catgaaattg   120
```

<210> SEQ ID NO 125
<211> LENGTH: 120
<212> TYPE: DNA
<213> ORGANISM: Artificial Sequence
<220> FEATURE:
<223> OTHER INFORMATION: primer no. 5888

<400> SEQUENCE: 125

```
tttctaatgc cttttccatc atgttactac gagttttctg aacctcctcg cacattggta    60
gcttaatttt aaattttttt ggtagtaaaa gatgcttata taaggatttc gtatttattg   120
```

<210> SEQ ID NO 126
<211> LENGTH: 120
<212> TYPE: DNA
<213> ORGANISM: Artificial Sequence
<220> FEATURE:
<223> OTHER INFORMATION: primer no. 5889

<400> SEQUENCE: 126

```
caataaatac gaaatcctta tataagcatc ttttactacc aaaaaaattt aaaattaagc    60
taccaatgtg cgaggaggtt cagaaaactc gtagtaacat gatggaaaag gcattagaaa   120
```

<210> SEQ ID NO 127
<211> LENGTH: 103
<212> TYPE: DNA
<213> ORGANISM: Artificial Sequence
<220> FEATURE:
<223> OTHER INFORMATION: primer no. 11271

<400> SEQUENCE: 127

```
ggtcgttttcc tgcacaataa taaattatct acactgaaat tgtagaattt cacctagacg    60
tggatatgat tatagagctt atagctacat cttttttagat aaa                     103
```

<210> SEQ ID NO 128
<211> LENGTH: 103
<212> TYPE: DNA
<213> ORGANISM: Artificial Sequence
<220> FEATURE:
<223> OTHER INFORMATION: primer no. 11272

<400> SEQUENCE: 128

```
tttatctaaa aagatgtagc tataagctct ataatcatat ccacgtctag gtgaaattct    60
acaatttcag tgtagataat ttattattgt gcaggaaacg acc                     103
```

<210> SEQ ID NO 129
<211> LENGTH: 120
<212> TYPE: DNA
<213> ORGANISM: Artificial Sequence

```
<220> FEATURE:
<223> OTHER INFORMATION: primer no. 11374

<400> SEQUENCE: 129
tttctttgtt agcttgggta ttatatttaa agtaacagaa aggaaagaaa aaagaaaaaa      60
ttattccgca ccaatttttt tttttattta tggtgtccgt tttcccaaca ttctttctgc     120

<210> SEQ ID NO 130
<211> LENGTH: 120
<212> TYPE: DNA
<213> ORGANISM: Artificial Sequence
<220> FEATURE:
<223> OTHER INFORMATION: primer no. 11375

<400> SEQUENCE: 130
gcagaaagaa tgttgggaaa acggacacca taaataaaaa aaaaaattgg tgcggaataa      60
ttttttcttt tttctttcct ttctgttact ttaaatataa tacccaagct aacaaagaaa     120
```